United States Patent
Park et al.

(10) Patent No.: US 12,377,130 B2
(45) Date of Patent: Aug. 5, 2025

(54) PHARMACEUTICAL COMPOSITION COMPRISING CCN5 AS ACTIVE INGREDIENT, FOR PREVENTING OR TREATING RETINAL DISEASES

(71) Applicant: OLIVES BIOTHERAPEUTICS INC., Gwangju (KR)

(72) Inventors: Woo Jin Park, Gwangju (KR); Aeri Yoon, Gwangju (KR)

(73) Assignee: OLIVES BIOTHERAPEUTICS INC., Gwangju (KR)

( * ) Notice: Subject to any disclaimer, the term of this patent is extended or adjusted under 35 U.S.C. 154(b) by 774 days.

(21) Appl. No.: 17/054,606

(22) PCT Filed: May 16, 2019

(86) PCT No.: PCT/KR2019/006011
§ 371 (c)(1),
(2) Date: Nov. 11, 2020

(87) PCT Pub. No.: WO2019/221576
PCT Pub. Date: Nov. 21, 2019

(65) Prior Publication Data
US 2021/0113660 A1    Apr. 22, 2021

(30) Foreign Application Priority Data
May 17, 2018 (KR) .................. 10-2018-0056499

(51) Int. Cl.
*A61K 38/18* (2006.01)
*A61K 9/00* (2006.01)
(Continued)

(52) U.S. Cl.
CPC ............ *A61K 38/18* (2013.01); *A61K 9/0048* (2013.01); *A61K 35/28* (2013.01); *A61K 35/30* (2013.01);
(Continued)

(58) Field of Classification Search
None
See application file for complete search history.

(56) References Cited

U.S. PATENT DOCUMENTS

| 4,797,368 A | 1/1989 | Carter et al. |
| 5,139,941 A | 8/1992 | Muzyczka et al. |

(Continued)

FOREIGN PATENT DOCUMENTS

| JP | 2009-512423 A | 3/2009 |
| KR | 10-2014-0014405 A | 2/2014 |

(Continued)

OTHER PUBLICATIONS

R Scott McIvor, Therapeutic Delivery of mRNA: The Medium Is the Message, Molecular Therapy, vol. 19, Issue 5, 2011, pp. 822-823, ISSN 1525-0016, https://doi.org/10.1038/mt.2011.67 (Year: 2011).*

(Continued)

*Primary Examiner* — Amy E Juedes
*Assistant Examiner* — Hilary Ann Petrash
(74) *Attorney, Agent, or Firm* — Sughrue Mion, PLLC

(57) ABSTRACT

A pharmaceutical composition containing a CCN5 or a fragment thereof, a nucleic acid encoding the CCN5, a vector containing the nucleic acid, or a recombinant cell containing the nucleic acid or the vector, as an active ingredient and its use in preventing or treating retinal diseases are disclosed. The CCN5 prevents fibrotic changes, caused by TGF-β, EEF, or anti-VEGF drugs, in retinal pigment epithelial cells. In addition, CCN5 recuperates the morphological or functional damage, caused by fibrotic changes, of retinal pigment epithelial cells to the level of normal cells. Therefore, the composition containing CCN5 as an active ingredient can be advantageously utilized for preventing or treating retinal diseases.

8 Claims, 41 Drawing Sheets
Specification includes a Sequence Listing.

(51) Int. Cl.
A61K 35/28 (2015.01)
A61K 35/30 (2015.01)
A61K 38/17 (2006.01)
A61K 39/395 (2006.01)
A61K 48/00 (2006.01)
A61P 27/02 (2006.01)
C07K 14/475 (2006.01)
C12N 15/86 (2006.01)

(52) U.S. Cl.
CPC ........ *A61K 38/179* (2013.01); *A61K 39/3955* (2013.01); *A61P 27/02* (2018.01); *C07K 14/475* (2013.01); *C12N 15/86* (2013.01); *A61K 48/00* (2013.01); *C12N 2750/14143* (2013.01)

(56) References Cited

U.S. PATENT DOCUMENTS

| | | | | |
|---|---|---|---|---|
| 2008/0020990 | A1* | 1/2008 | Yano | A61P 7/00 536/23.1 |
| 2013/0108548 | A1* | 5/2013 | Vlieghe | C07K 7/06 530/323 |
| 2014/0031410 | A1 | 1/2014 | Mendell et al. | |

FOREIGN PATENT DOCUMENTS

| | | |
|---|---|---|
| KR | 10-2015-0065891 A | 6/2015 |
| WO | 2007/033215 A2 | 3/2007 |
| WO | 2017/082701 A1 | 5/2017 |

OTHER PUBLICATIONS

Hossein Salehi, Noushin Amirpour, Shahnaz Razavi, Ebrahim Esfandiari, Reihaneh Zavar. Overview of retinal differentiation potential of mesenchymal stem cells: A promising approach for retinal cell therapy, Annals of Anatomy—Anatomischer Anzeiger, vol. 210, 2017, pp. 52-63, ISSN 0940-9602 (Year: 2017).*
Bradley, J., Ju, M. & Robinson, G.S. Combination therapy for the treatment of ocular neovascularization. Angiogenesis 10, 141-148 (2007). https://doi.org/10.1007/s10456-007-9069-x (Year: 2007).*
Inherited Retinal Disorders. Boston Children Hospital. Inherited Retinal Disorders | Boston Children's Hospital (childrenshospital. org). http://www.childrenshosptial.org/conditions/inherited-retinal-disorders (Year: 2023).*
Birdshot Chorioretinophathy. Cleveland Clinic. Birdshot Chorioretinophathy: What It Is, Symptoms & Treatment (clevelandclinic. org). http://www.my.clevelandclinic.org/health/diseases/24310-retinoschisis (Year: 2023).*
Retinoschosis. Cleveland Clinic. Retinoschisis: What It Is, Causes & Symptoms (clevelandclinic.org). http://www.my.clevelandclinic. org/health/diseases/23024-birdshot-chorioretinopathy (Year: 2023).*
Supplemental Methods: Dongtak Jeong, et al. Matricellular Protein CCN5 Reverses Established Cardiac Fibrosis, Journal of the American College of Cardiology, vol. 67, Issue 13, 2016, pp. 1556-1568, ISSN 0735-1097 (Year: 2016).*
Retinal Diseases: Overview and Types (clevelandclinic.org), Diabetic retinopathy—Prevention—NHS (www.nhs.uk ). https://my.clevelandclinic.org/health/diseases/24853-retinal-diseases (Year: 2023).*
Merriam-Webster, "Prevent", available online at Preventing Definition & Meaning—Merriam-Webster, (accessed on Sep. 26, 2023). https://www.merriam-webster.com/dictionary/preventing. (Year: 2023).*
Merriam Webster, "fragment", available online at Fragment Definition & Meaning—Merriam-Webster (accessed on Sep. 26, 2023)). https://www.merriam-webster.com/dictionary/fragment (Year: 2023).*
*Homo sapiens* connective tissue growth fator related protein WISP-2 (WISP-2) mRNA, coplete cds. 2023. GenBank. Sequence Id: AF100780.2. Query is Seq ID No. 5. (Year: 2023).*
CCN5 family member 5 isoform 1 precursor [*Homo sapiens*]. 2023. PeptBank. Sequence ID: NP_001310299.1. Query is Seq ID No. 6. (Year: 2023).*
Mendoza et al. Arch. Anti-tumor chemotherapy utilizing peptide based approaches-apoptotic pathways, kinases and proteasome as targets. Immunol. Ther. Exp., vol. 53, p. 47-60, 2005 (Year: 2005).*
Eck and Wilson, Goodman & Gilman's The Pharmacological basis of Therapeutics, 1996, McGraw-Hill, New York, NY. p. 77-101 (Year: 1996).*
Niidome et al. Gene Therapy Progress and Prospects: Nonviral vectors. Gene Therapy, 2002, 9:1647-1652 (Year: 2002).*
Zhang et al. In vivo gene delivery by nonviral vectors: overcoming hurdles. Molecular Therapy, 2012, 20:1298-1304 (Year: 2012).*
Gao et al. Nonviral Gene Delivery: What we know and what is next. The AAPS Journal, 2007, 9:E92-E104 (Year: 2007).*
Parker et al. Nonviral gene delivery: techniques and implications for molecular medicine. Expert Reviews in Molecular Medicine, 2003, 5:1-15 (Year: 2003).*
Verma et al. Sustained expression of genes delivered directly into liver and muscle by lentiviral vectors. Nature, 1997, 389:239-242 (Year: 1997).*
Lundstrom. Viral vectors in gene therapy. Diseases 2018, 6, 42; doi:10.3390/diseases6020042 (Year: 2018).*
Ramamoorth and Narvekar. Nonviral vectors in gene therapy-an overview. Jour. Of Clin. And Diag. Research. Jan. 2015, vol. 9(1):GE01-GE06 (Year: 2015).*
Friedlander. 2007. Fibrosis and diseases of the eye. J Clin Invest. 2007;117(3):576-586. https://doi.org/10.1172/JCI31030. (Year: 2007).*
Natarajan S. Retinitis pigmentosa: a brief overview. Indian J Ophthalmol. Sep.-Oct. 2011;59(5):343-6. doi: 10.4103/0301-4738.83608 . PMID: 21836337; PMCID: PMC3159313 (Year: 2011).*
Pennock et al. Ranibizumab Is a Potential Prophylaxis for Proliferative Vitreoretinopathy, a Nonangiogenic Blinding Disease. The American Journal of Pathology, vol. 182, No. 5, May 2013 (Year: 2013).*
Gray et al. CCN5 expression in mamals. II. adult rodent tissues. J. Cell Commun. Signal. 2007. 1:145-158. DOI 10.1007/s12079-007-0013-z (Year: 2007).*
Jong et al. Fibrosis and Cardiac Arrythmias. J Cardiovasc Pharmacol vol. 57, No. 6, Jun. 2011 (Year: 2001).*
Shareef et al. (2014). Cardiac SERCA2A/B: therapeutic targets for heart failure. European journal of pharmacology, 724, 1-8 (Year: 2014).*
Bagheri et al., "Simultaneous application of bevacizumab and anti-CTGF antibody effectively suppresses proangiogenic and profibrotic factors in human RPE cells", Molecular Vision, vol. 21, pp. 378-390, 2015 (14 pages total).
Leask, "Yin and Yang Part Deux: CCN5 inhibits the pro-fibrotic effects of CCN2", Journal of Cell Communication and Signaling, vol. 4, No. 3, pp. 155-156, 2010 (3 pages total).
Saika, "Fibrotic disorders in the eye: targets of gene therapy", J. Wakayama, Med. Soc., vol. 58, No. 4, pp. 156-165, 2007 (12 pages total).
Igarashi et al., "New innovations for ocular gene therapy", The Medical Association of Nippon Medical School, vol. 13, No. 2, pp. 88-96, 2017 (9 pages total).
Li et al., "Chapter 73 Personalized Medicine: Cell and Gene Therapy Based on Patient-Specific iPSC-Derived Retinal Pigment Epithelium Cells", Advances in Experimental Medicine and Biology, vol. 854, pp. 549-555, 2016 (8 pages total).
Seung Hoon Yoo, Md, et al., Unilateral Retinitis Pigmentosa: A Case Series and Literature Review, The Korean Ophthalmological Society, 2015, pp. 559-566, vol. 56, No. 4.
Pyoung Oh Yoon, et al., "The opposing effects of CCN2 and CCN5 on the development of cardiac hypertrophy and fibrosis", Journal of Molecular and Cellular Cardiology, 2010, pp. 294-303, vol. 49.
Yang Liu, et al., "Induction by Latanoprost of Collagen Gel Contraction Mediated by Human Tenon Fibroblasts: Role of Intracellular Signaling Molecules", IOVS, Apr. 2008, pp. 1429-1436, vol. 49, No. 4.
S.K. Parapuram, et al., "Effects of Transforming Growth Factor Beta on Human Retinal Pigment Epithelial Cells", ARVO Annual Meeting Abstract, May 2004.

(56) References Cited

OTHER PUBLICATIONS

Michele Sabbah, et al., "CCN5, a Novel Transcriptional Repressor of the Transforming Growth Factor B Signaling Pathway", Molecular and Cellular Biology, Apr. 2011, pp. 1459-1469, vol. 31, No. 7.
NCBI, "Mus musculus WNT1 inducible signaling pathway protein 2 (Wisp2), mRNA", NCBI Reference Sequence No. 016873.2, Jan. 21, 2018.
Aeri Yoon, et al., "The matricellular protein CCN5 inhibits fibrotic deformation of retinal pigment epithelium", PLOS ONE, Dec. 20, 2018, pp. 1-15.
Korea Intellectual Property Office, Office Action issued from Korean Patent Application No. 10-2019-0057624 issued on Jan. 6, 2020.
International Search Report for PCT/KR2019/006011 dated Aug. 19, 2019 (PCT/ISA/210).
Shizuya Saika, "TGFβ pathology in the eye", Laboratory Investigation, 2006, vol. 86, No. 2, pp. 106-115 (10 pages total).
Database EMBL [Online], XP002805797, retrieved from EBI accession No. EM_STD:BC032877 Database accession No. BC032877, Sep. 24, 2002, 3 pages total.
Dongtak Jeong et al., "Matricellular Protein CCN5 Reverses Established Cardiac Fibrosis", Journal of the American College of Cardiology, 2016, vol. 67, No. 13, pp. 1556-1568 (13 pages total).

\* cited by examiner

Control     AdLacZ +EEF     AdCCN5 +EEF

Control  AdLacZ +Beva  AdCCN5 +Beva

SEQUENCE LISTING

```
<160> NUMBER OF SEQ ID NOS: 6

<210> SEQ ID NO 1
<211> LENGTH: 251
<212> TYPE: PRT
<213> ORGANISM: Artificial Sequence
<220> FEATURE:
<223> OTHER INFORMATION: CCN5(mouse)

<400> SEQUENCE: 1

Met Arg Gly Asn Pro Leu Ile His Leu Leu Ala Ile Ser Phe Leu Cys
1               5                   10                  15

Ile Leu Ser Met Val Tyr Ser Gln Leu Cys Pro Ala Pro Cys Ala Cys
```

```
            20                  25                  30
Pro Trp Thr Pro Pro Gln Cys Pro Pro Gly Val Pro Leu Val Leu Asp
            35                  40                  45

Gly Cys Gly Cys Cys Arg Val Cys Ala Arg Arg Leu Gly Glu Ser Cys
        50                  55                  60

Asp His Leu His Val Cys Asp Pro Ser Gln Gly Leu Val Cys Gln Pro
65                  70                  75                  80

Gly Ala Gly Pro Ser Gly Arg Gly Ala Val Cys Leu Phe Glu Glu Asp
                85                  90                  95

Asp Gly Ser Cys Glu Val Asn Gly Arg Arg Tyr Leu Asp Gly Glu Thr
            100                 105                 110

Phe Lys Pro Asn Cys Arg Val Leu Cys Arg Cys Asp Asp Gly Gly Phe
        115                 120                 125

Thr Cys Leu Pro Leu Cys Ser Glu Asp Val Arg Leu Pro Ser Trp Asp
        130                 135                 140

Cys Pro Arg Pro Arg Arg Ile Gln Val Pro Gly Arg Cys Cys Pro Glu
145                 150                 155                 160

Trp Val Cys Asp Gln Ala Val Met Gln Pro Ala Ile Gln Pro Ser Ser
                165                 170                 175

Ala Gln Gly His Gln Leu Ser Ala Leu Val Thr Pro Ala Ser Ala Asp
            180                 185                 190

Gly Pro Cys Pro Asn Trp Ser Thr Ala Trp Gly Pro Cys Ser Thr Thr
        195                 200                 205

Cys Gly Leu Gly Ile Ala Thr Arg Val Ser Asn Gln Asn Arg Phe Cys
        210                 215                 220

Gln Leu Glu Ile Gln Arg Arg Leu Cys Leu Ser Arg Pro Cys Leu Ala
225                 230                 235                 240

Ser Arg Ser His Gly Ser Trp Asn Ser Ala Phe
                245                 250

<210> SEQ ID NO 2
<211> LENGTH: 756
<212> TYPE: DNA
<213> ORGANISM: Artificial Sequence
<220> FEATURE:
<223> OTHER INFORMATION: CCN5(mouse)

<400> SEQUENCE: 2
atgaggggca acccactgat ccatcttctg gccatttcct tcctctgcat tctctcaatg    60
gtgtatgccc agctgtgccc agcaccctgt gcctgtcctt ggacaccacc ccagtgccca   120
ccgggggtac ccctggtgct ggatggctgt ggctgctgtc gagtgtgtgc acggaggctg   180
ggggagtcct gcgaccacct gcatgtctgc aaccccagcc agggcctggt ttgtcagcct   240
ggggcaggcc ccagtggccg tggtgttgtg tgcctcttcg aagaggatga cgggagctgt   300
gaggtgaacg gccgcaggta cctggatggg gagaccttta aacccaattg cagggttttg   360
tgccgctgtg atgacggtgg tttcacctgc ctgccgctgt gcagtgagga tgtgcggctg   420
cccagctggg actgcccacg ccccaggaga atacaggtgc caggaaggtg ctgccccgag   480
tgggtgtgtg accaggcagt gatgcagccg gcaatccagc cctcctcagc caaggacac    540 caactttctg cccttgtcac tcctgcatct gccgatggcc cctgtccaaa ctggagcaca   600
gcctggggcc cctgctcaac cacctgtggg ttgggcatag ccaccgagt atccaaccag    660 aaccgattct gccaactgga gatccagcgt cgcctgtgtc tgtccagacc ctgcctggca   720
tccaggagcc acggctcatg gaacagtgcc ttctag                              756
```

<210> SEQ ID NO 3
<211> LENGTH: 228
<212> TYPE: PRT
<213> ORGANISM: Artificial Sequence
<220> FEATURE:
<223> OTHER INFORMATION: CCN5(except signal peptide, mouse)

<400> SEQUENCE: 3

Gln Leu Cys Pro Ala Pro Cys Ala Cys Pro Trp Thr Pro Pro Gln Cys
1               5                   10                  15

Pro Pro Gly Val Pro Leu Val Leu Asp Gly Cys Gly Cys Cys Arg Val
                20                  25                  30

Cys Ala Arg Arg Leu Gly Glu Ser Cys Asp His Leu His Val Cys Asp
            35                  40                  45

Pro Ser Gln Gly Leu Val Cys Gln Pro Gly Ala Gly Pro Ser Gly Arg
        50                  55                  60

Gly Ala Val Cys Leu Phe Glu Glu Asp Gly Ser Cys Glu Val Asn
65                  70                  75                  80

Gly Arg Arg Tyr Leu Asp Gly Glu Thr Phe Lys Pro Asn Cys Arg Val
                85                  90                  95

Leu Cys Arg Cys Asp Asp Gly Gly Phe Thr Cys Leu Pro Leu Cys Ser
            100                 105                 110

Glu Asp Val Arg Leu Pro Ser Trp Asp Cys Pro Arg Pro Arg Arg Ile
        115                 120                 125

Gln Val Pro Gly Arg Cys Cys Pro Glu Trp Val Cys Asp Gln Ala Val
    130                 135                 140

Met Gln Pro Ala Ile Gln Pro Ser Ser Ala Gln Gly His Gln Leu Ser
145                 150                 155                 160

Ala Leu Val Thr Pro Ala Ser Ala Asp Gly Pro Cys Pro Asn Trp Ser
                165                 170                 175

Thr Ala Trp Gly Pro Cys Ser Thr Thr Cys Gly Leu Gly Ile Ala Thr
            180                 185                 190

Arg Val Ser Asn Gln Asn Arg Phe Cys Gln Leu Glu Ile Gln Arg Arg
        195                 200                 205

Leu Cys Leu Ser Arg Pro Cys Leu Ala Ser Arg Ser His Gly Ser Trp
    210                 215                 220

Asn Ser Ala Phe
225

<210> SEQ ID NO 4
<211> LENGTH: 250
<212> TYPE: PRT
<213> ORGANISM: Artificial Sequence
<220> FEATURE:
<223> OTHER INFORMATION: CCN5(human)

<400> SEQUENCE: 4

Met Arg Gly Thr Pro Lys Thr His Leu Leu Ala Phe Ser Leu Leu Cys
1               5                   10                  15

Leu Leu Ser Lys Val Arg Thr Gln Leu Cys Pro Thr Pro Cys Thr Cys
                20                  25                  30

Pro Trp Pro Pro Pro Arg Cys Pro Leu Gly Val Pro Leu Val Leu Asp
            35                  40                  45

Gly Cys Gly Cys Cys Arg Val Cys Ala Arg Arg Leu Gly Glu Pro Cys
        50                  55                  60

Asp Gln Leu His Val Cys Asp Ala Ser Gln Gly Leu Val Cys Gln Pro

```
              65                  70                  75                  80
     Gly Ala Gly Pro Gly Gly Arg Gly Ala Leu Cys Leu Leu Ala Glu Asp
                      85                  90                  95

Asp Ser Ser Cys Glu Val Asn Gly Arg Leu Tyr Arg Glu Gly Glu Thr
                 100                 105                 110

Phe Gln Pro His Cys Ser Ile Arg Cys Arg Cys Glu Asp Gly Gly Phe
             115                 120                 125

Thr Cys Val Pro Leu Cys Ser Glu Asp Val Arg Leu Pro Ser Trp Asp
         130                 135                 140

Cys Pro His Pro Arg Arg Val Glu Val Leu Gly Lys Cys Cys Pro Glu
     145                 150                 155                 160

Trp Val Cys Gly Gln Gly Gly Leu Gly Thr Gln Pro Leu Pro Ala
                     165                 170                 175

Gln Gly Pro Gln Phe Ser Gly Leu Val Ser Ser Leu Pro Gly Val
                 180                 185                 190

Pro Cys Pro Glu Trp Ser Thr Ala Trp Gly Pro Cys Ser Thr Thr Cys
             195                 200                 205

Gly Leu Gly Met Ala Thr Arg Val Ser Asn Gln Asn Arg Phe Cys Arg
         210                 215                 220

Leu Glu Thr Gln Arg Arg Leu Cys Leu Ser Arg Pro Cys Pro Pro Ser
     225                 230                 235                 240

Arg Gly Arg Ser Pro Gln Asn Ser Ala Phe
                     245                 250

<210> SEQ ID NO 5
<211> LENGTH: 753
<212> TYPE: DNA
<213> ORGANISM: Artificial Sequence
<220> FEATURE:
<223> OTHER INFORMATION: CCN5(human)

<400> SEQUENCE: 5
atgagaggca caccgaagac ccacctcctg gccttctccc tcctctgcct cctctcaaag      60
gtgcgtaccc agctgtgccc gacaccatgt acctgcccct ggccacctcc ccgatgcccg     120
ctgggagtac ccctggtgct ggatggctgt ggctgctgcc gggtatgtgc acggcggctg     180
ggggagccct gcgaccaact ccacgtctgc gacgccagcc agggcctggt ctgccagccc     240
ggggcaggac ccggtggccg gggggccctg tgcctcttgg cagaggacga cagcagctgt     300
gaggtgaacg gccgcctgta tcgggaaggg agaccttcc agccccactg cagcatccgc      360
tgccgctgcg aggacggcgg cttcacctgc gtgccgctgt gcagcgagga tgtgcggctg     420
cccagctggg actgccccca ccccaggagg gtcgaggtcc tgggcaagtg ctgccctgag     480
tgggtgtgcg gccaaggagg gggactgggg acccagcccc ttccagccca aggaccccag     540
ttttctggcc ttgtctcttc cctgcccct ggtgtcccct gcccagaatg gagcacggcc      600
tggggaccct gctcgaccac ctgtgggctg gcatggcca cccgggtgtc aaccagaac      660 cgcttctgcc gactggagac ccagcgccgc ctgtgcctgt ccaggccctg ccaccctcc     720 aggggtcgca gtccacaaaa cagtgccttc tag                                  753

<210> SEQ ID NO 6
<211> LENGTH: 227
<212> TYPE: PRT
<213> ORGANISM: Artificial Sequence
<220> FEATURE:
<223> OTHER INFORMATION: CCN5(except signal peptide, human)
```

```
<400> SEQUENCE: 6

Gln Leu Cys Pro Thr Pro Cys Thr Cys Pro Trp Pro Pro Arg Cys
1               5                   10                  15

Pro Leu Gly Val Pro Leu Val Leu Asp Gly Cys Gly Cys Cys Arg Val
                20              25              30

Cys Ala Arg Arg Leu Gly Glu Pro Cys Asp Gln Leu His Val Cys Asp
            35              40              45

Ala Ser Gln Gly Leu Val Cys Gln Pro Gly Ala Gly Pro Gly Gly Arg
        50              55              60

Gly Ala Leu Cys Leu Leu Ala Glu Asp Asp Ser Ser Cys Glu Val Asn
65                  70              75                      80

Gly Arg Leu Tyr Arg Glu Gly Glu Thr Phe Gln Pro His Cys Ser Ile
                85              90              95

Arg Cys Arg Cys Glu Asp Gly Gly Phe Thr Cys Val Pro Leu Cys Ser
            100             105             110

Glu Asp Val Arg Leu Pro Ser Trp Asp Cys Pro His Pro Arg Arg Val
            115             120             125

Glu Val Leu Gly Lys Cys Cys Pro Glu Trp Val Cys Gly Gln Gly Gly
        130             135             140

Gly Leu Gly Thr Gln Pro Leu Pro Ala Gln Gly Pro Gln Phe Ser Gly
145             150             155                         160

Leu Val Ser Ser Leu Pro Pro Gly Val Pro Cys Pro Glu Trp Ser Thr
                165             170             175

Ala Trp Gly Pro Cys Ser Thr Thr Cys Gly Leu Gly Met Ala Thr Arg
            180             185             190

Val Ser Asn Gln Asn Arg Phe Cys Arg Leu Glu Thr Gln Arg Arg Leu
        195             200             205

Cys Leu Ser Arg Pro Cys Pro Pro Ser Arg Gly Arg Ser Pro Gln Asn
        210             215             220

Ser Ala Phe
225
```

PHARMACEUTICAL COMPOSITION COMPRISING CCN5 AS ACTIVE INGREDIENT, FOR PREVENTING OR TREATING RETINAL DISEASES

CROSS REFERENCE TO RELATED APPLICATIONS

This application is a National Stage of International Application No. PCT/KR2019/006011 filed May 16, 2019, claiming priority based on Korean Patent Application No. 10-2018-0056499 filed May 17, 2018.

TECHNICAL FIELD

The present disclosure relates to a pharmaceutical composition comprising a CCN5 protein, a CCN5-encoding nucleic acid molecule, or a vector containing the nucleic acid molecule as an active ingredient as well as its use in preventing or treating a retinal disease.

BACKGROUND ART

The retina is a thin transparent membrane that lines the innermost wall of the eye and is in contact with the vitreous body in the eye. The retina serves as a primary organ for visual information processing which converts optical information of an object into electrical signals and transmits images through the optic nerve to the visual cortex of the brain. The retina is a sophisticated tissue composed of more than 100 million photoreceptor cells, more than 1 million ganglion cells, which are retinal output neurons, and numerous neurons that serve as cables connecting these cells. The macular lutea, a central part of the retina which distinguishes colors and objects and provides vision, is composed of a photoreceptor cell layer consisting of cone cells and a ganglion cell layer. In the macular lutea, the electrical signals of images are converted into chemical signals, which are in turn transmitted to the brain through the optic nerve formed of the axons of ganglion cells. The part of the retina, other than the macula lutea, is responsible for recognizing the periphery and playing a major role in the dark.

Once an abnormality occurs in the retina due to aging or external factors, this abnormality causes problems with vision and visual field, and leads to blindness in severe cases. Retinal diseases include retinal detachment, in which the retina lifts away from the back of the eye as the neural retina is detached from the retinal pigment epithelium (RPE) cell layer, thereby causing vision impairment; peripheral retinal degeneration that causes abnormalities in the tissue around the retina; and macular degeneration that causes abnormalities in the macula lutea. Once the retina is detached from the retinal pigment epithelium, it is not possible to receive optical information about the image. In addition, the nutrient supply from the choroid is not achieved, and thus neurons do not function properly. If this condition persists, permanent retinal atrophy occurs, leading to blindness (Yoo, 2015).

The retinal pigment epithelium is located between the neural retina and the choroid, and is a cubic polarized monolayer that plays a pivotal role in maintaining retinal function. Normal retinal pigment epithelium has a morphologically and functionally asymmetric structure. Deformation of retinal pigment epithelial cells may lead to fibrotic eye diseases such as proliferative vitreoretinopathy (PVR), diabetic retinopathy (DR), and age-related macular degeneration (AMD). Under pathological conditions, the retinal pigment epithelial cells are deformed, so that these cells do not have their native morphology and also lose the exocytotic and phagocytotic functions.

On the other hand, in a case where visual impairment begins due to fibrotic deformation of retinal pigment epithelial cells, recovery to the previous vision cannot be achieved. Thus, it is important to detect and treat such deformation at an early stage. Regarding the fibrotic deformation of retinal pigment epithelial cells, early detection and treatment thereof can minimize vision loss; however, there are currently no reliable treatments.

DISCLOSURE OF INVENTION

Technical Problem

While studying therapeutic agents for diseases caused by fibrotic deformation of retinal pigment epithelial cells, the present inventors have found that CCN5 restores the morphological or functional damage of retinal pigment epithelial cells, caused by transforming growth factor-β (TGF-β), to the level of normal cells, and thus has an excellent effect on prevention or treatment of retinal diseases. Based on this finding, the present inventors have completed the present invention.

An object of the present invention is to provide a pharmaceutical composition for preventing or treating a retinal disease, comprising CCN5 as an active ingredient.

Solution to Problem

In order to achieve the above object, an aspect of the present invention provides a pharmaceutical composition for preventing or treating a retinal disease, comprising, as an active ingredient, CCN5 or a fragment thereof.

In addition, an aspect of the present invention provides a pharmaceutical composition for preventing or treating a retinal disease, comprising, as an active ingredient, a polynucleotide that encodes CCN5.

In addition, another aspect of the present invention provides a pharmaceutical composition for preventing or treating a retinal disease, comprising, as an active ingredient, a recombinant virus containing a polynucleotide that encodes CCN5.

In addition, an aspect of the present invention provides a method for preventing or treating a retinal disease, comprising a step of administering the pharmaceutical composition to an individual.

In addition, an aspect of the present invention provides a pharmaceutical composition for preventing or treating a retinal disease, comprising, as active ingredients, CCN5 or a fragment thereof; and an anti-VEGF (vascular endothelial growth factor) drug.

In addition, another aspect of the present invention provides a pharmaceutical composition for preventing or treating a retinal disease, comprising, as active ingredients, a polynucleotide that encodes CCN5 or a recombinant virus containing a polynucleotide that encodes CCN5; and an anti-VEGF drug.

In addition, still another aspect of the present invention provides a kit for preventing or treating a retinal disease, comprising, as active ingredients, a polynucleotide that encodes CCN5 or a recombinant virus containing a polynucleotide that encodes CCN5; and an anti-VEGF drug.

In addition, an aspect of the present invention provides a composition for preventing or treating a retinal disease, comprising, as an active ingredient, a cell into which a polynucleotide that encodes CCN5 is introduced.

Advantageous Effects of Invention

The CCN5 according to the present invention, a polynucleotide encoding the same, or a virus containing the polynucleotide prevents fibrotic deformation of retinal pigment epithelial cells, induced by TGF-β, EEF (EGTA (ethylene glycol-bi (β-aminoethylether)-N,N,N;N;-tetraacetic acid)+EGF (epidermal growth factor)+FGF2 (fibroblast growth factor 2)), or an anti-VEGF drug. In addition, the CCN5, the polynucleotide encoding the same, or the virus containing the polynucleotide can restore the morphological or functional damage of retinal pigment epithelial cells, caused by fibrotic deformation, to the level of normal cells. Accordingly, a composition comprising, as an active ingredient, the CCN5, the polynucleotide encoding the same, or the virus containing the polynucleotide can be effectively used for preventing or treating a retinal disease.

BEST MODE FOR CARRYING OUT THE INVENTION

Figure 1A:
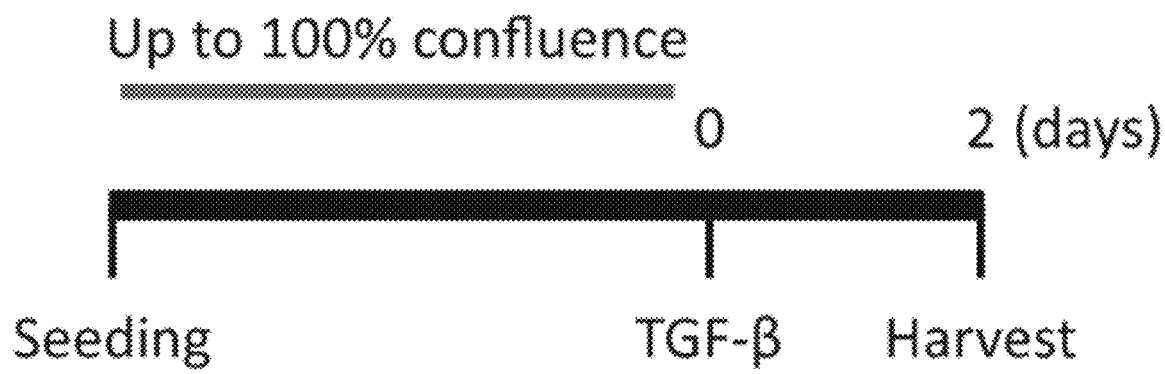
FIG. 1a schematically illustrates an experimental process for studying fibrotic deformation of ARPE-19 cells induced by TGF-β.

In an aspect of the present invention, there is provided a pharmaceutical composition for preventing or treating a retinal disease, comprising, as an active ingredient, CCN5 or a fragment thereof, and its use in preventing or treating a retinal disease.

As used herein, the term "CCN5" refers to an extracellular matrix (ECM)-related protein belonging to the CCN family (CCN1 to 6) that plays various roles in vascular diseases, angiogenesis, oncogenesis, induction of fibrosis diseases, and regulation of cellular functions such as cell differentiation and survival. CCN5 protein, unlike other CCN family proteins, has no C-terminal domain, and is also called WISP-2, HICP, Cop1, CTGF-L, or the like. In addition, the CCN5 protein consists of a single polypeptide chain of 250 amino acid residues.

The pharmaceutical composition for preventing or treating a retinal disease of the present invention can prevent or treat fibrotic deformation of retinal pigment epithelial cells. The fibrotic deformation may be induced by any one selected from the group consisting of TGF-β, EGTA, EGF, FGF-2, and anti-VEGF drugs. In an embodiment of the present invention, it was identified that CCN5 prevents fibrotic deformation of RPE cells, induced by TGF-β that is known as a trigger for deformation of retinal pigment epithelium (RPE) cells. In addition, in another embodiment, it was identified that CCN5 restores RPE cells, in which fibrotic deformation has already occurred, to normal cells.

The CCN5 as used herein may be human- or animal-derived CCN5. In an embodiment of the present invention, it was identified that mouse- or human-derived CCN5 has an inhibitory effect on fibrotic deformation of RPE cells.

The mouse-derived CCN5 may be a polypeptide including the amino acid sequence of SEQ ID NO: 1. In addition, the polynucleotide encoding the mouse-derived CCN5 may include the nucleotide sequence of SEQ ID NO: 2. In addition, in the present invention, the mouse-derived CCN5 may be in a mature form. Specifically, the mouse-derived CCN5 may be the amino acid sequence of positions 24 to 251 of SEQ ID NO: 1 (SEQ ID NO: 3) obtained by exclusion of the amino acids of positions 1 to 23, which correspond to a signal peptide, from the amino acid sequence of SEQ ID NO: 1.

The human-derived CCN5 may be a polypeptide including the amino acid sequence of SEQ ID NO: 4. In addition, the polynucleotide encoding the human-derived CCN5 may include the nucleotide sequence of SEQ ID NO: 5. In addition, in the present invention, the human-derived CCN5 may be in a mature form. Specifically, the human-derived CCN5 may be the amino acid sequence of positions 24 to 250 of SEQ ID NO: 4 (SEQ ID NO: 6) obtained by exclusion of the amino acids of positions 1 to 23, which correspond to a signal peptide, from the amino acid sequence of SEQ ID NO: 4.

As used herein, the term "retinal disease" refers to a disease caused by deformation or loss of function of retinal pigment epithelial cells. Specifically, the retinal disease may be any one selected from the group consisting of proliferative vitreoretinopathy, diabetic retinopathy, macular degeneration, choroidal neovascularization, and retinal edema. Here, the retinal pigment epithelium (RPE) is located between the neural retina and the choroid, and is a cubic polarized monolayer that plays an important role in maintaining the function of the retina.

The proliferative vitreoretinopathy is a disease in which in a case of exacerbation of diabetic retinopathy or in a case where a fissure is incompletely closed in retinal detachment surgery, fibrotic cells multiply on the retinal surface or in the vitreous body to form a membrane and the membrane contracts so that retinal detachment is caused. In a case where retinal detachment occurs, retinal pigment epithelial cells are released and transformed into fibrotic cells; and the fibrotic cells are combined with glial cells, which have multiplied on the retinal surface, to form a thin film or traction band. When this film or traction band contracts, fixed wrinkles are formed as the entire retina condenses. Here, in severe cases, the entire retina except for the optic disc may be detached in a funnel shape.

The diabetic retinopathy is a complication that occurs in the retina of the eye due to peripheral circulatory disorder caused by diabetes. The disease may initially have no symptoms and may exhibit symptoms of decreased vision as its invasion into the macular lutea occurs. The diabetic retinopathy may be divided into simple retinopathy, preproliferative retinopathy, and proliferative retinopathy, depending on the progression stage.

The macular degeneration is a disease in which the macular function decreases as aging progresses, so that vision decreases or is lost. In a case where vision starts to decrease due to this disease, recovery to the previous vision cannot be achieved. The disease is called age-related macular degeneration and is a leading cause of vision loss in old age. The macular degeneration is divided into two types: dry macular degeneration and wet macular degeneration. About 90% of patients suffering from macular degeneration have dry macular degeneration, and this dry macular degeneration occurs in a case where age-related deposits accumulate under the retina or lesions such as retinal pigment epithelial atrophy develop. As visual cells in the macula are slowly destroyed, the macular function decreases and the central vision decreases over time. For the wet macular degeneration, symptoms occur due to abnormal formation of many new blood vessels in the choroid that make up the lower layer of the macular lutea. The wet macular degeneration progresses faster than the dry macular degeneration, which may lead to a sharp drop in vision and lead to blindness within 2 months to 3 years.

The choroidal neovascularization is a disease in which the choroid is damaged due to formation of abnormal blood vessels, so that visual impairment occurs. The choroidal neovascularization is one of the leading causes of irreversible vision loss worldwide. For the choroidal neovascularization, despite various therapeutic attempts, prognosis of vision is poor for most patients.

The retinal edema means that the retina is swollen. As a degeneration or abnormality occurs in fine blood vessels such as capillaries in the retina or macula for various reasons, bleeding may occur, resulting in retinal edema. In a case where edema occurs in the retina, various symptoms may occur, including decreased vision.

In the pharmaceutical composition for preventing or treating a retinal disease, comprising CCN5 as an active ingredient, CCN5 protein as the active ingredient may be contained in 10% to 95% by weight with respect to the total weight of the pharmaceutical composition. Also, in addition to the active ingredient, the pharmaceutical composition of the present invention may further comprise one or more active ingredients that exhibit the same or similar function. In addition to the above-described active ingredients, the pharmaceutical composition according to the present invention may further comprise one or more pharmaceutically acceptable carriers for administration.

In another aspect of the present invention, there is provided a pharmaceutical composition for preventing or treating a retinal disease, comprising, as an active ingredient, a polynucleotide that encodes CCN5 as well as its use in preventing or treating a retinal disease.

The polynucleotide may be mRNA encoding CCN5. The mRNA encoding CCN5 may be a sequence complementary to SEQ ID NO: 2 or SEQ ID NO: 5 which is a polynucleotide that encodes CCN5. In an embodiment of the present invention, it was identified that modified mRNA encoding CCN5 restores fibrotic deformation of RPE cells induced by TGF-β or EEF (EGTA, EGF, and FGF-2), which is known as a trigger for deforming RPE cells, to the level of normal cells. Modified mRNA refers to mRNA that has been modified in various forms. Such modifications include capping of the 5' end of mRNA, poly-A tail binding to (polyadenylation of) the 3' end of mRNA, and addition of a modified nucleotide such as 5-methylcytidine and 2-thiouridine.

In yet another aspect of the present invention, there is provided a pharmaceutical composition for preventing or treating a retinal disease, comprising, as an active ingredient, a recombinant virus containing a polynucleotide that encodes CCN5.

The polynucleotide may be a nucleotide sequence encoding the amino acid sequence of SEQ ID NO: 1 or SEQ ID NO: 4 which represents CCN5, and the nucleotide sequence may be SEQ ID NO: 2 or SEQ ID NO: 5. In addition, the polynucleotide may further include a promoter operatively linked thereto so that CCN5 is expressed.

As used herein, the term "operatively linked" refers to functional binding between a nucleotide expression regulatory sequence (for example, promoter, signal sequence, or array of transcription factor binding sites) and another nucleotide sequence. The regulatory sequence may regulate transcription and/or translation of the other nucleic acid sequence.

Specifically, the promoter bound to the polynucleotide that encodes CCN5 may operate preferably in animal cells and more preferably in mammalian cells, to regulate transcription of the CCN5 protein gene. The promoter includes a promoter derived from a mammalian virus and a promoter derived from the genome of a mammalian cell.

The promoter may be any one selected from the group consisting of cytomegalovirus (CMV) promoter, adenovirus late promoter, vaccinia virus 7.5K promoter, SV40 promoter, herpes simplex virus (HSV) tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter. However, the promoter is not limited thereto. Specifically, the promoter may be CMV promoter.

The virus may be any one selected from the group consisting of adenovirus, adeno-associated virus (AAV), retrovirus, lentivirus, herpes simplex virus, and vaccinia virus. The adeno-associated virus is not limited to a specific serotype, and may preferably be any one of AAV1, AAV2, AAV3, AAV4, AAV5, AAV6, AAV7, AAV8, and AAV9.

The adeno-associated virus (AAV) is suitable as a gene delivery system of the present invention because it is capable of infecting non-dividing cells and has an ability to infect various types of cells. Details on construction and use of AAV vectors are specifically disclosed in U.S. Pat. Nos. 5,139,941 and 4,797,368.

Typically, the AAV virus may be produced by co-transfection of a plasmid comprising a gene sequence of interest flanked by two AAV terminal repeats and an expression plasmid comprising a wild-type AAV coding sequence without terminal repeats.

The retinal disease is as described above, and may be any one selected from the group consisting of proliferative vitreoretinopathy, diabetic retinopathy, macular degeneration, choroidal neovascularization, and retinal edema.

In addition, a dose of the pharmaceutical composition for preventing or treating a retinal disease, comprising, as an active ingredient, a recombinant virus containing a polynucleotide that encodes CCN5, may vary depending on various factors including type of disease, severity of disease, types and amounts of active ingredients and other ingredients contained in the pharmaceutical composition, type of formulation and the patient's age, weight, general health status, gender and diet, time of administration, route of administration, duration of treatment, and simultaneously used drugs.

In still yet another aspect of the present invention, there is provided a method for preventing or treating a retinal disease, comprising a step of administering, to an individual, a pharmaceutical composition for preventing or treating a retinal disease, according to the present invention, the pharmaceutical composition comprising, as an active ingredient, the CCN5 or a fragment thereof, the polynucleotide that encodes CCN5, or the recombinant virus containing a polynucleotide that encodes CCN5.

A dose of the pharmaceutical composition comprising, as an active ingredient, the CCN5 or a fragment thereof, the polynucleotide that encodes CCN5, or the recombinant virus containing a polynucleotide that encodes CCN5, according to the present invention, may vary depending on various factors including type of disease, severity of disease, types and amounts of active ingredients and other ingredients contained in the pharmaceutical composition, type of formulation and the patient's age, weight, general health status, gender, time of administration, route of administration, duration of treatment, and simultaneously used drugs.

However, in the pharmaceutical composition for preventing or treating a retinal disease, comprising CCN5 as an active ingredient, according to the present invention, CCN5 protein may be contained in an effective amount of 0.0001 to 100 mg/kg so that the pharmaceutical composition exhibits a desirable effect. Here, the administration may be performed once or several times a day.

In addition, the recombinant virus included in the pharmaceutical composition according to the present invention may be administered in an amount of $1.0 \times 10^5$ to $1.0 \times 10^{15}$ viral genomes per day on an adult basis. Specifically, in a dose of the pharmaceutical composition of the present invention, the virus may be administered in an amount of $1.0 \times 10^5$ to $1.0 \times 10^{15}$, $1.0 \times 10^7$ to $1.0 \times 10^{13}$, $1.0 \times 10^8$ to $1.0 \times 10^{12}$, or $1.0 \times 10^9$ to $1.0 \times 10^{10}$ per day on an adult basis.

In addition, the pharmaceutical composition of the present invention may be administered to an individual in need thereof by various methods known in the art. The individual may be a mammal, specifically a human. The route of administration may be appropriately selected by a person skilled in the art in consideration of administration method, body fluid volume, viscosity, and the like. Specifically, the administration may be performed via any one selected from the group consisting of intravenous, intraarterial, intraperitoneal, intramuscular, intrasternal, transdermal, intranasal, inhalation, topical, rectal, oral, intraocular, intravitreal, and intradermal routes. In an embodiment of the present invention, a virus encoding CCN5 was administered intravitreally.

In still yet another aspect of the present invention, there is provided a pharmaceutical composition for preventing or treating a retinal disease, comprising, as active ingredients, CCN5 or a fragment thereof; and an anti-VEGF drug.

As used herein, the term "anti-VEGF drug" refers to a drug used to inhibit vascular endothelial growth factor (VEGF), and may be used to treat specific cancers or age-related macular degeneration. Specifically, the anti-VEGF drug may be bevacizumab, ranibizumab, or aflibercept.

Bevacizumab, sold under the brand name Avastin, is a drug used to treat a number of types of cancers and a specific eye disease. For cancer, bevacizumab is administered by slow injection into a vein and used for colorectal cancer, lung cancer, glioblastoma, renal cell carcinoma, and the like. In addition, for macular degeneration, bevacizumab is administered by direct injection into the eye. In a case where bevacizumab is used for cancer, common side effects thereof include nose bleeds, headache, high blood pressure, rash, and the like. Other severe side effects thereof include gastrointestinal perforation, bleeding, allergic reactions, blood clots, and an increased risk of infection. In a case where bevacizumab is used for eye disease, side effects thereof include vision loss and retinal detachment. Bevacizumab is an angiogenesis inhibitor and belongs to monoclonal antibody-based drugs. Bevacizumab works by slowing the growth of new blood vessels.

Ranibizumab, sold under the brand name LUCENTIS®, is a monoclonal antibody fragment (Fab) created from the same parent mouse antibody as bevacizumab. Ranibizumab, which is an anti-angiogenic drug that has been approved to treat wet age-related macular degeneration, is similar to bevacizumab in terms of effectiveness and rates of side effects.

Aflibercept, sold under the brand name EYLEA®, is a drug that has been approved to treat wet macular degeneration in the United States and Europe.

In still yet another aspect of the present invention, there is provided a pharmaceutical composition for preventing or treating a retinal disease, comprising, as active ingredients, a polynucleotide that encodes CCN5 or a recombinant virus containing a polynucleotide that encodes CCN5; and an anti-VEGF drug.

In addition, according to the present invention, there is provided a kit for preventing or treating a retinal disease, comprising, as active ingredients, a polynucleotide that encodes CCN5 or a recombinant virus containing a polynucleotide that encodes CCN5; and an anti-VEGF drug.

Here, the polynucleotide that encodes CCN5, the recombinant virus containing a polynucleotide that encodes CCN5, and the anti-VEGF drug are as described above.

In still yet another aspect of the present invention, there is provided a composition for preventing or treating a retinal disease, comprising, as an active ingredient, a cell into which a polynucleotide that encodes CCN5 is introduced.

The cell may be a cell into which an exogenous polynucleotide that encodes CCN5 is introduced. Specifically, the CCN5 may be a human-derived CCN5.

In addition, the cell may be a stem cell or a retinal pigment epithelial cell. The stem cell may be an induced pluripotent stem cell (iPSC) or an adult stem cell. Specifically, the adult stem cell may be a mesenchymal stem cell (MSC), a multipotent stem cell, or an amniotic epithelial cell. In addition, the mesenchymal stem cell may be derived from any one selected from the group consisting of umbilical cord, cord blood, bone marrow, fat, muscle, nerve, skin, amniotic membrane, and placenta.

In an embodiment of the present invention, an experiment was performed which identified an effect of CCN5 in human induced pluripotent stem cell-derived RPE cells with fibrotic deformation having been induced by TGF-β. As a result of the above experiment, it was identified that fibrotic deformation of iPSC-derived RPE cells induced by TGF-β is prevented by CCN5.

Therefore, according to the present invention, there may be provided a composition for preventing or treating a retinal disease, comprising, as an active ingredient, a cell into which a polynucleotide that encodes CCN5, for preventing or treating fibrotic deformation of RPE cells, is introduced. In addition, according to the present invention, there may be provided a cell therapeutic agent containing a cell into which a polynucleotide that encodes CCN5 is introduced.

In the present invention, the "cell therapeutic agent" refers to a medical product used for the purpose of treatment, diagnosis, and prevention, which is obtained through a series of actions such as performing ex vivo proliferation and screening of living autologous, allogeneic or xenogeneic cells or otherwise altering biological properties of the cells, to restore the functions of cells and tissues.

The cell therapeutic agent may be classified into a somatic cell therapeutic agent and a stem cell therapeutic agent, depending on the type and degree of differentiation of cells used. The stem cell therapeutic agent may be classified into an embryonic stem cell therapeutic agent and an adult stem cell therapeutic agent.

Mode for the Invention

Hereinafter, the present invention will be described in detail by way of examples. However, the following examples are only to illustrate the present invention, and the present invention is not limited thereto.

I. Experimental Preparation and Experimental Method

EXAMPLE 1

Animal Model

Model mice were produced by backcrossing Ccl2−/− mice (Jackson Laboratories, USA) with C57BL/6 wild-type (WT) mice (Damul Science, Korea) ten times. AAV9-VLP or AAV9-CCN5 was injected into 18-month-old Ccl2−/− mice. All animal experimental methods and protocols were approved by the Institutional Animal Care and Use Committee of the School of Life Sciences, Gwangju Institute of Science and Technology, and carried out in the facility therein according to the approved guidelines (IACUC GIST-2015-24). Here, the VLP means virus-like particles.

Age-matched WT mice having received AAV9-VLP were used as a control. The mice were anesthetized by intraperitoneal injection of Zoletil 50 (Virbac, France) and Rompun (Bayer Korea, Korea) at a ratio of 3:1. After surgical procedure, the mice were monitored every other day to check whether any adverse events occurred. As a result of the monitoring, no harmful clinical symptoms were observed in other organs. After 12 weeks, the mice were euthanized with $CO_2$, and the eyes were enucleated.

EXAMPLE 2

Reagents

Recombinant TGF-β2 was purchased from PeproTech Korea (Korea). ARPE-19 cells were treated with the recombinant TGF-β2 at 10 ng/ml. Recombinant EGF and FGF-2 were purchased from Invitrogen (USA). ARPE-19 cells were treated with 1 mM of EGTA, 10 ng/ml of EGF, and 20 ng/ml of FGF-2. In addition, ARPE-19 cells were treated with the three anti-VEGF drugs, bevacizumab (0.25 mg/ml, Genetech/Roche, USA), ranibizumab (0.125 mg/ml, Novartis Pharma Stein AG, Switzerland), and aflibercept (0.5 mg/ml, Bayer Pharma AG, Germany).

EXAMPLE 3

Production of Adeno-Associated Virus (AAV) Vector and Adenovirus

AAVs (serotypes 2 and 9) that express human CCN5 gene using CMV promoter were acquired by requesting Virovek Inc., a U.S. company, to produce and purify the same. As such, AAV2-CCN5 and AAV9-CCN5 were obtained. In addition, a method for producing and purifying a recombinant adenovirus that expresses amino-terminal hemagglutinin (HA)-tagged mouse CCN5 has been described in a previous study (Yoon P O, et al. The opposing effects of CCN2 and CCN5 on the development of cardiac hypertrophy and fibrosis. J Mol Cell Cardiol. 2010; 49(2): 294-303). In this way, AdLacZ and AdCCN5, which are adenoviruses containing genes encoding LacZ and CCN5, respectively, were produced.

EXAMPLE 4

Production of Modified mRNA Encoding CCN5

Modified mRNA encoding CCN5 was acquired by requesting TriLink BioTechnologies, a U.S. company, to produce and purify the same. This modified mRNA is capped with CleanCap at the 5' end, and has a polyA tail linked to the 3' end. In addition, this modified mRNA contains 5-methylcytidine and 2-thiouridine.

EXAMPLE 5

Cell Culture

A retinal pigment epithelial cell line (ARPE-19; ATCC, USA) was cultured in a 5% $CO_2$ incubator at 37° C. using Dulbecco's modified Eagle's medium and Ham's F12 Nutrient Mixture medium (DMEM/F12; Welgene, Korea), containing 1% antibiotics (Gibco, USA) and 10% fetal bovine serum (FBS; HyClone, USA). The medium was replaced with fresh medium every other day. When the cells were cultured to a certain extent in a culture plate, these cells were subcultured using 0.25% trypsin/0.02% EDTA (Gibco, USA).

Human iPSC-derived retinal pigment epithelium (RPE) cells were obtained from Axol Bioscience (USA). The cells were cultured in a 5% $CO_2$ incubator at 37° C. using Dulbecco's modified Eagle's medium and Ham's F12 Nutrient Mixture medium (DMEM/F12; Gibco, USA), containing 2% B-27 supplement (Gibco, USA) and 1% antibiotic-antifungal agent (Gibco, USA) at a ratio of 7:3. The cells were seeded on 8-well chamber slides (Corning Life Science, USA) precoated with MATRIGEL® (Corning Life Science, USA) at 100,000 cells per well, and the medium was replaced with fresh medium on a daily basis.

The cultured cells were divided into the following two groups and subjected to drug treatment: one group in which induction of differentiation of retinal pigment epithelial cells into mesenchymal cells was suppressed; and the other group in which retinal pigment epithelial cells that had been induced to differentiate into mesenchymal cells were caused to return to normal retinal pigment epithelial cells. The ARPE-19 cells were grown in serum-free medium for 24 hours. Then, the cells were treated with AdCCN5 at 50 multiplicity of infection (MOI) followed by 10 ng/ml of TGF-β2 (PeproTech Korea, Korea), or treated with TGF-β2 followed by AdCCN5.

EXAMPLE 6

Western Blotting

For in vitro experiments, the cultured ARPE-19 cells were washed with phosphate buffered saline (PBS), and suspended with a mixed solution of cold RIPA buffer (1% NP-40, 50 mM Tris-HCl [pH 7.4], 150 mM NaCl, and 10 mM NaF) and a protease inhibitor cocktail (Roche, Germany). The cell suspension was subjected to treatment with an ultrasonic generator for 5 minutes at an amplitude of 5% with a cycle of 2 seconds on/1 second off.

For in vivo experiments, the eyes were enucleated from the $Cc2^{-/-}$ mice. Only the retina/choroid/sclera complex was removed from each eye and placed in cold RIPA buffer. The complex was subjected to treatment with an ultrasonic generator using a ⅛ inch microtip for 10 seconds at an amplitude of 5% with an on-off cycle of 2 seconds/2 seconds. The cell lysate was centrifuged at 13,000 rpm for 20 minutes. The supernatant in which proteins are dissolved was taken and the protein concentration therein was measured using a bicinchoninic acid protein assay kit (BCA, Thermo Fisher Scientific, USA). The equal amount of protein sample was mixed with 5×SDS buffer and subjected to SDS-PAGE electrophoresis. Then, the proteins were transferred to a polyvinylidene difluoride membrane (Millipore, USA). The membrane was blocked for 1 hour in a Tris-buffer containing 5% skim milk, and then incubated with primary antibodies overnight at 4° C. Then, the membrane was incubated with secondary antibodies conjugated with horseradish peroxidase (HRP, Jackson ImmunoResearch), treated with chemiluminescent substrate (Amersham), and developed through IMAGEQUANT® LAS 4,000 Mini imager (GE Healthcare). Protein quantitative analysis was performed using ImageJ software (NIH).

EXAMPLE 7

Immunofluorescence Staining

Cells that had been grown by being seeded in a 12-well culture plate, each well containing a coverslip, were fixed with 4% formaldehyde and treated with 0.2% Triton X-100 for 10 minutes. The cells were blocked with a diluted solution of 5% bovine serum albumin in PBS, and incubated with anti-ZO-1 and anti-α-SMA antibodies overnight at 4° C. For secondary antibodies, the cells were incubated for 1 hour at room temperature with FITC- or Alexa Fluor 594-conjugated secondary antibodies, TEXAS RED®-conjugated phalloidin (Invitrogen, USA) for f-actin staining, and Hoechst 33342 (Invitrogen, USA) for nuclear staining. The results were observed using an epifluorescence microscope (Zeiss, Germany). For retinal flat-mount experiments, the eyes were enucleated from the mice, and each eye was fixed in 4% formaldehyde for 24 hours. The RPE/choroid/sclera complex was treated with a solution, which contains a semi-permeable solution and a blocking solution, at room temperature for 2 hours and 1 hour, respectively, and then incubated with primary antibodies overnight at 4° C. The complex was washed with PBS and incubated for 2 hours at room temperature with secondary antibodies. Washing with PBS was performed and nuclear staining was performed with DAPI (4',6-diamidino-2-phenylindole, Sigma Aldrich, USA). The RPE/choroid/sclera complex was washed again with PBS and mounted with FLUOROMOUNT® (Sigma Aldrich, USA). Observation was performed under a fluorescence microscope.

Meanwhile, the information on primary antibodies used in the present invention is shown in Table 1 below.

TABLE 1

| Antibody | Manufacturer | Dilution ratio | Experiment performed | Origin |
| --- | --- | --- | --- | --- |
| ZO-1 | Invitrogen | 1:1000 | WB, ICC | Rabbit |
| ZO-1 | Invitrogen | 1:200 | IHC | Mouse |
| Occludin | Invitrogen | 1:1000 | WB | Rabbit |
| Fibronectin | Sigma-Aldrich | 1:1000 | WB | Rabbit |
| α-SMA | Sigma-Aldrich | 1:1000 | WB, ICC | Mouse |
| Vimentin | Santa Cruz | 1:1000 | WB | Mouse |
| HA | Roche | 1:1000 | WB | Mouse |
| Type I collagen | Abcam | 1:1000 | WB | Mouse |
| CCN5 | GenScript | 1:1000 | WB | Mouse |
| CCN5 | OriGene | 1:200 | IHC | Rabbit |
| MerTK | R&D Systems | 1:1000 | WB | Goat |
| RPE65 | Abcam | 1:1000 | WB | Mouse |
| GAPDH | Abcam | 1:1000 | WB | Rabbit |

EXAMPLE 8

RNA Extraction and Quantitative Real-Time Polymerase Chain Reaction

RNA was extracted using TRIZOL™ (Invitrogen, USA) reagent. cDNA was synthesized using a reverse transcription kit (Promega, USA), and real-time polymerase chain reaction was performed using SYBR® green (TAKARA, Japan). The level of RNA was analyzed by analyzing the amplification reaction curve, and this analysis was performed in triplicate or quadruplicate. The relative expression level of genes was quantified by normalization to 18s rRNA.

EXAMPLE 9

Collagen Gel Contraction Assay

Collagen gel contraction assays were performed as previously described (Liu Y, et al. Induction by latanoprost of collagen gel contraction mediated by human tenon fibroblasts: role of intracellular signaling molecules, Investigative ophthalmology & visual science, 2008; 49(4): 1429-36). Specifically, cultured ARPE-19 cells were mixed with 1.2 mg/ml of collagen solution (Invitrogen, USA), and 1 N NaOH was added to neutralize the pH of the collagen solution. The collagen gel suspension ($1 \times 10^5$ cells/well, 500 µL) was added to a 24-well culture plate and polymerized for 1 hour at 37° C. When the collagen gel was formed, the edges thereof were removed with a pipette tip so that the gel is suspended in the medium. Then, treatment with various reagents was performed, and the extent of collagen gel contraction was measured and analyzed using ImageJ software (imagej.net/ImageJ).

EXAMPLE 10

In Vitro Analysis of Cell Migration Ability

In order to measure the cell migration ability, ARPE-19 cells were placed on a 12-well culture plate, each well containing a coverslip, and cultured until the cultured cells cover the entire area of the coverslip. Treatment with reagents was performed according to the experimental design, and then the cells were scratched using a 200 µL tip. After 24 hours, the cells were stained with DAPI and observed under a fluorescence microscope. Thereafter, the cell migration distance was measured using ImageJ software.

EXAMPLE 11

Phagocytosis Assay

ARPE-19 cells were seeded into a 24-well culture plate at a density of $5 \times 10^4$ cells per well, and treated with AdLacZ or AdCCN5, and TGF-β. Treatment with TAMRA®-labeled apoptotic thymocytes or 1 mg/ml of PHRODO® Red BioParticles (Invitrogen, USA) was performed in a 5% $CO_2$ incubator at 37° C. for 6 and 4 hours, respectively, to observe an effect thereof on phagocytic activity.

In order to generate the TAMRA®-labeled apoptotic thymocytes, the thymus was obtained from 5- to 6-week-old C57BL/6 mice, and dissociated using a 5 ml syringe piston and a cell strainer to separate single thymocytes. The thymocytes were stained with 50 µM TAMRA®-SE (Invitrogen, USA) for 30 minutes in a cell incubator at 37° C. Thereafter, the thymocytes were de-stained by being incubated for 20 minutes under a condition of 37° C. in RPMI containing 10% fetal bovine serum and 1% penicillin/streptomycin/glutamine, and washed once with complete RPMI. Apoptosis of the thymocytes was induced by treatment with 50 µM dexamethasone (Calbiochem, Germany) in a $CO_2$ cell incubator at 37° C. for 4 hours. Thereafter, the cells were washed 3 times with complete RPMI, and $2 \times 10^5$ apoptotic thymocytes were resuspended in 300 µl of phagocyte culture medium.

The apoptotic thymocyte suspension was incubated with the ARPE-19 cells in a cell incubator. Thereafter, the phagocytes were washed 5 times with cold PBS, trypsinized, and suspended in complete culture medium. Then, analysis was performed using a FACSCanto™ II flow cytometer (BD, USA).

Such ARPE-19 cells were gated according to the forward scatter/side scatter plot to distinguish between the ARPE-19 cells having performed phagocytosis and the ARPE-19 cells having not. The marker M1 was used for the gating, and then the percentage of fluorescence-positive events from 20,000 live cells per sample was calculated. Data were analyzed using FlowJo software (flowjo.com/).

EXAMPLE 12

Intravitreal Injection of AAV9-CCN5 and AAV9-VLP

AAV9-CCN5 was intravitreally injected using a 33 G needle underneath an operating microscope (Leica Microsystems Ltd., Germany). The opposite eye served as an AAV9-VLP control.

EXAMPLE 13

Statistical Analysis

Quantitative gene expression analysis was repeated three or more times. The experimental results were expressed in the form of mean±standard deviation, and statistical analysis was performed using Student's t-test. Statistical significance is indicated by an asterisk (*, $p<0.05$ or **, $p<0.01$).

II. Identification of Effect of CCN5 in ARPE-19 Cells

EXPERIMENTAL EXAMPLE 1

Identification of Inhibitory Effect of CCN5 on Fibrotic Deformation of ARPE Cells ARPE-19 is a cell line spontaneously induced to differentiate from human RPE. The mature ARPE-19 cells form a cobblestone-like monolayer and express marker proteins specific for epithelial cells. The cultured ARPE-19 cells were treated with TGF-β at 5 ng/ml or 10 ng/ml for 2 days (FIG. 1a). The results are illustrated in FIGS. 1b to 1d.

Figure 1B:
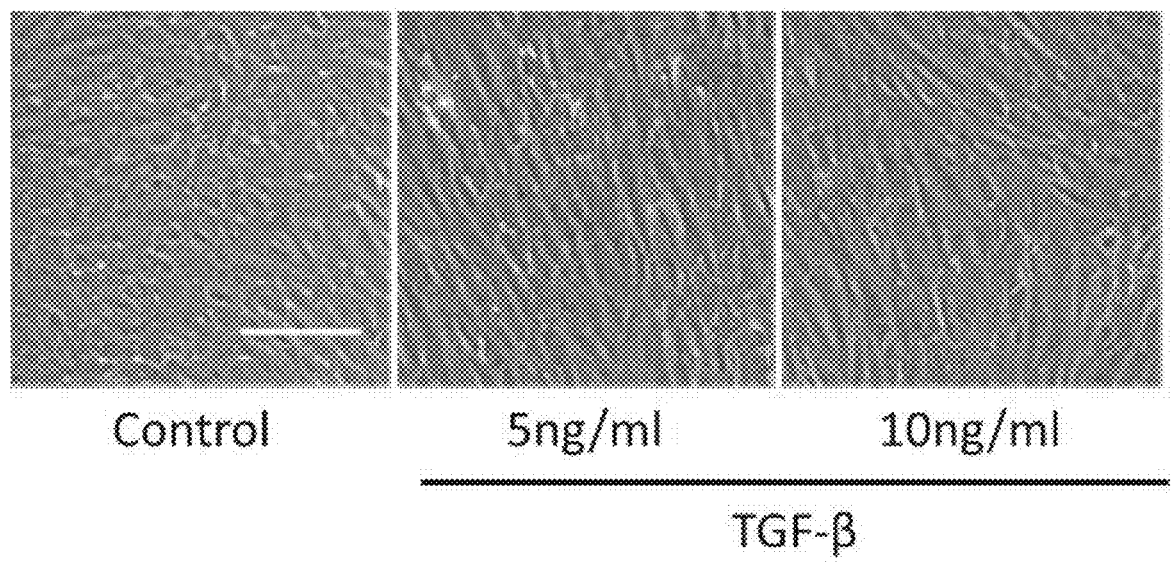
FIG. 1b illustrates results obtained by observing, under a microscope, fibrotic deformation of ARPE-19 cells when the ARPE-19 cells are treated with TGF-β at indicated concentrations.
Figure 1C:
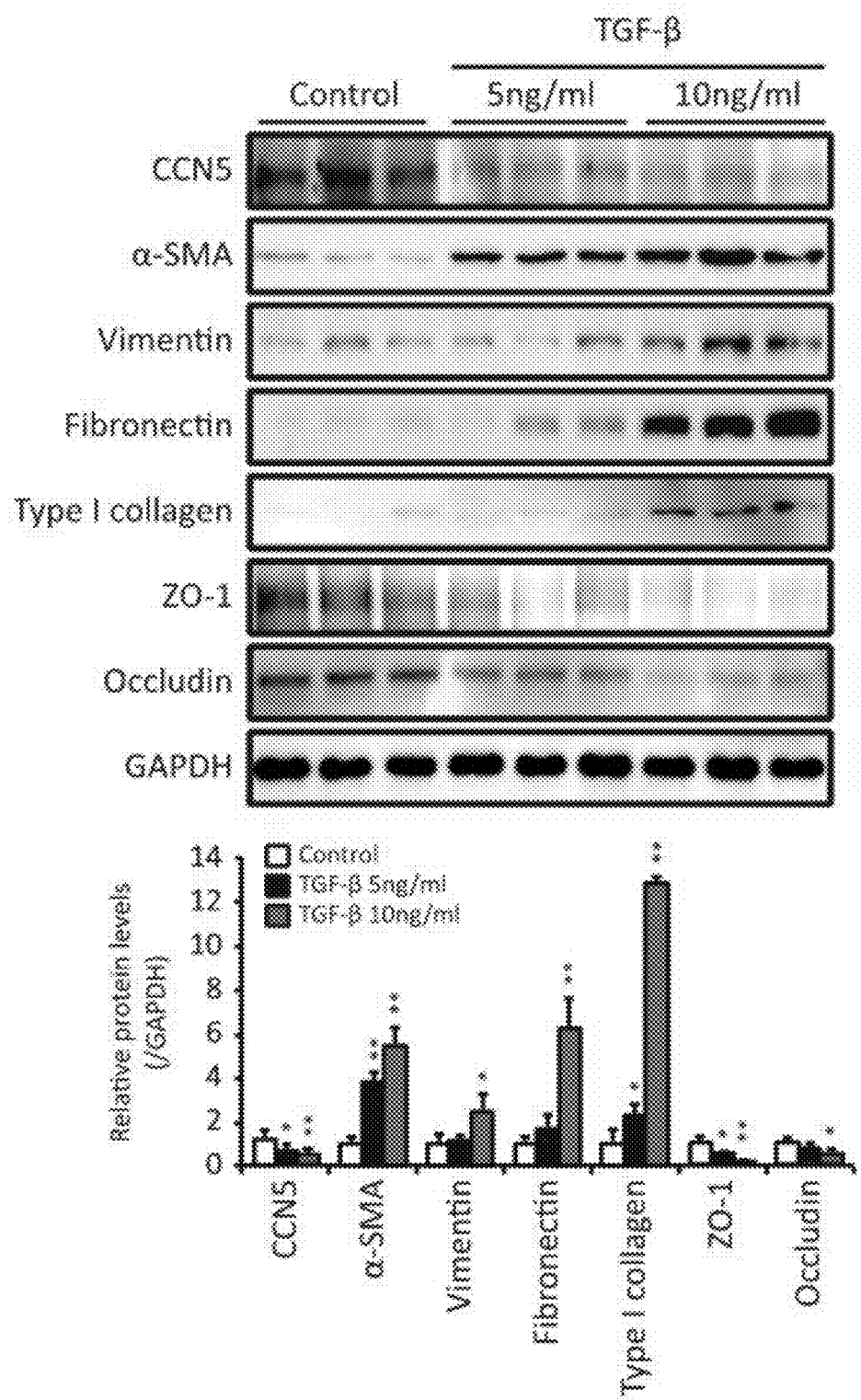
FIG. 1c illustrates results obtained by identifying changes in protein expression pattern which occur when the ARPE-19 cells are treated with TGF-β at indicated concentrations.
Figure 1D:
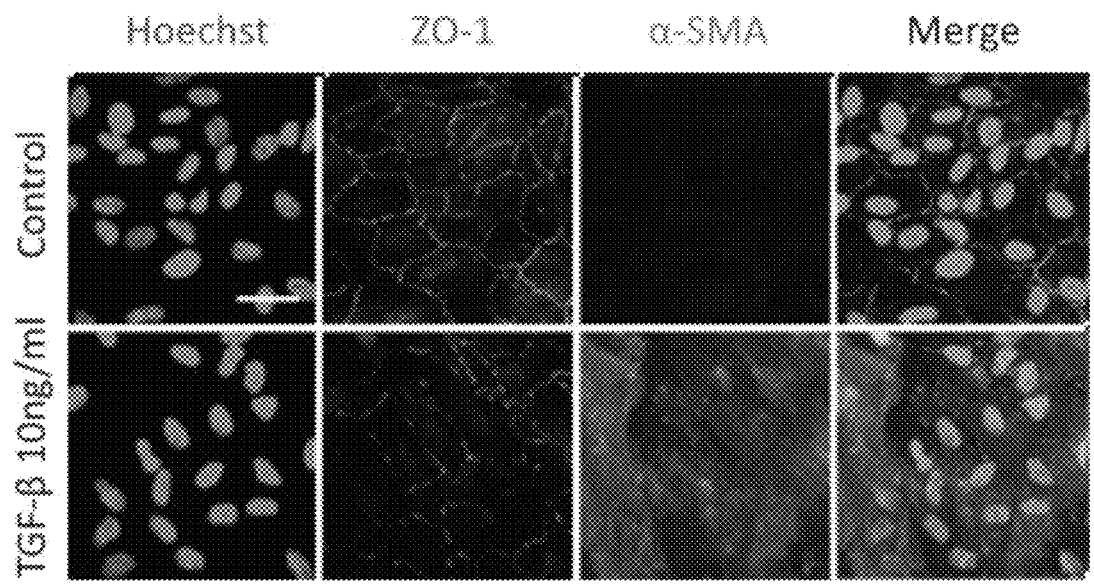
FIG. 1d illustrates results obtained by subjecting ARPE-19 cells to treatment with TGF-β, and then observing cellular tight junction using anti-ZO-1 antibody, anti-α-SMA (smooth muscle actin) antibody, and phalloidin.
Figure 1D:
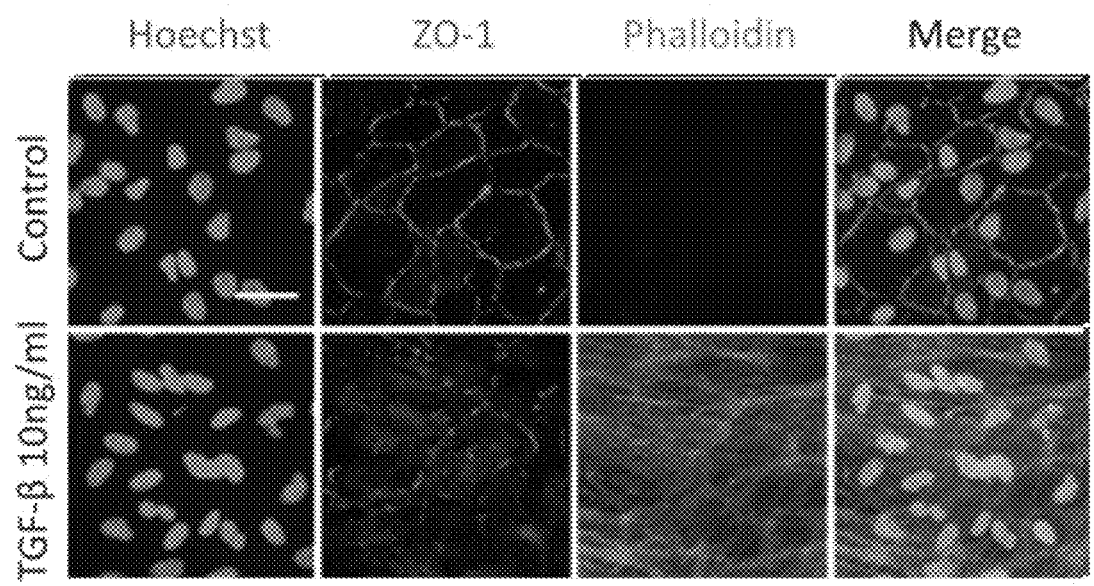

As illustrated in FIG. 1b, after treatment with TGF-β, the ARPE-19 cells acquired a fibroblastic morphology. In particular, as illustrated in FIG. 1c, it was identified that treatment with TGF-β significantly decreased the expression level of human-derived CCN5 protein. In parallel, the expression of the mesenchymal marker proteins, α-SMA, vimentin, fibronectin, and type I collagen, was increased, whereas the expression of the epithelial marker proteins, ZO-1 and occludin, was significantly decreased. In addition, it was identified through immunofluorescence staining that in a case of being treated with TGF-β, the expression of α-SMA and f-actin is increased and the formation of tight junction is inhibited (FIG. 1d). From these results, it was found that treatment with TGF-β induces fibrotic deformation of ARPE-19 cells. Therefore, in subsequent experiments, the ARPE-19 cells were treated with 10 ng/ml of TGF-β for 48 hours, to induce fibrotic deformation.

Figure 2A:
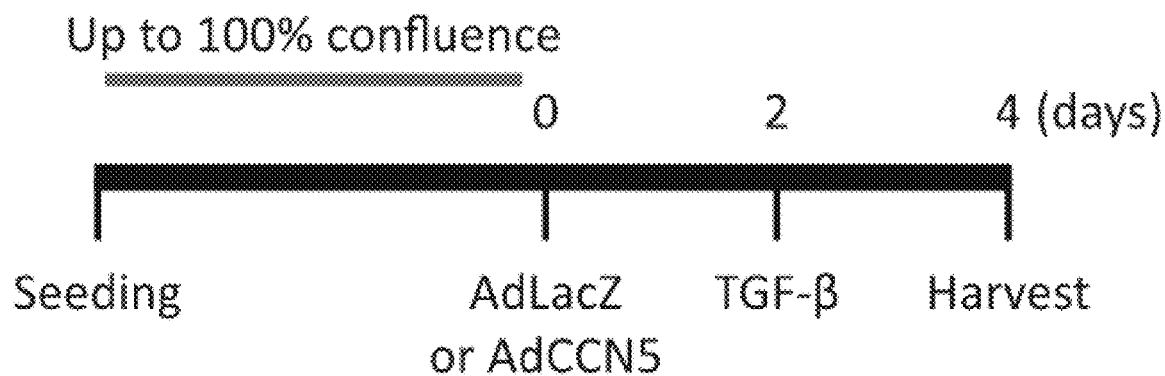
FIG. 2a schematically illustrates an experimental process for identifying an inhibitory effect of AdCCN5 on fibrotic deformation of ARPE-19 cells induced by TGF-β.

The ARPE-19 cells were infected with recombinant adenovirus (AdCCN5) expressing mouse-derived CCN5, or AdLacZ as a control. On day 2 after infection, the cells were treated with TGF-β (FIG. 2a). The results are illustrated in FIGS. 2b to 2d.

Figure 2B:
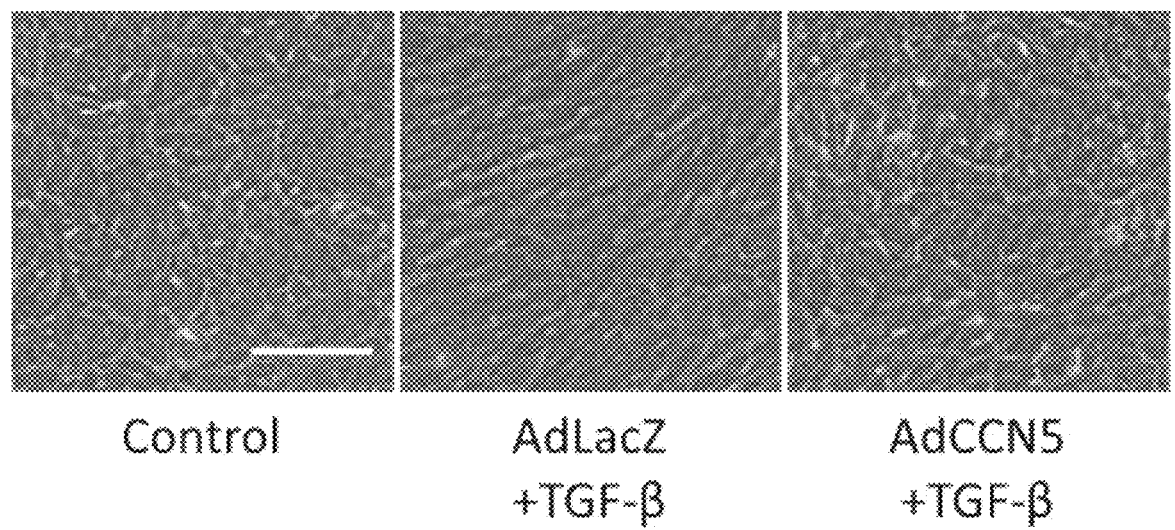
FIG. 2b illustrates results obtained by subjecting ARPE-19 cells to treatment with AdLacZ or AdCCN5, and then observing, under a microscope, morphological changes in the ARPE-19 cells which occur when treated with TGF-β.
Figure 2C:
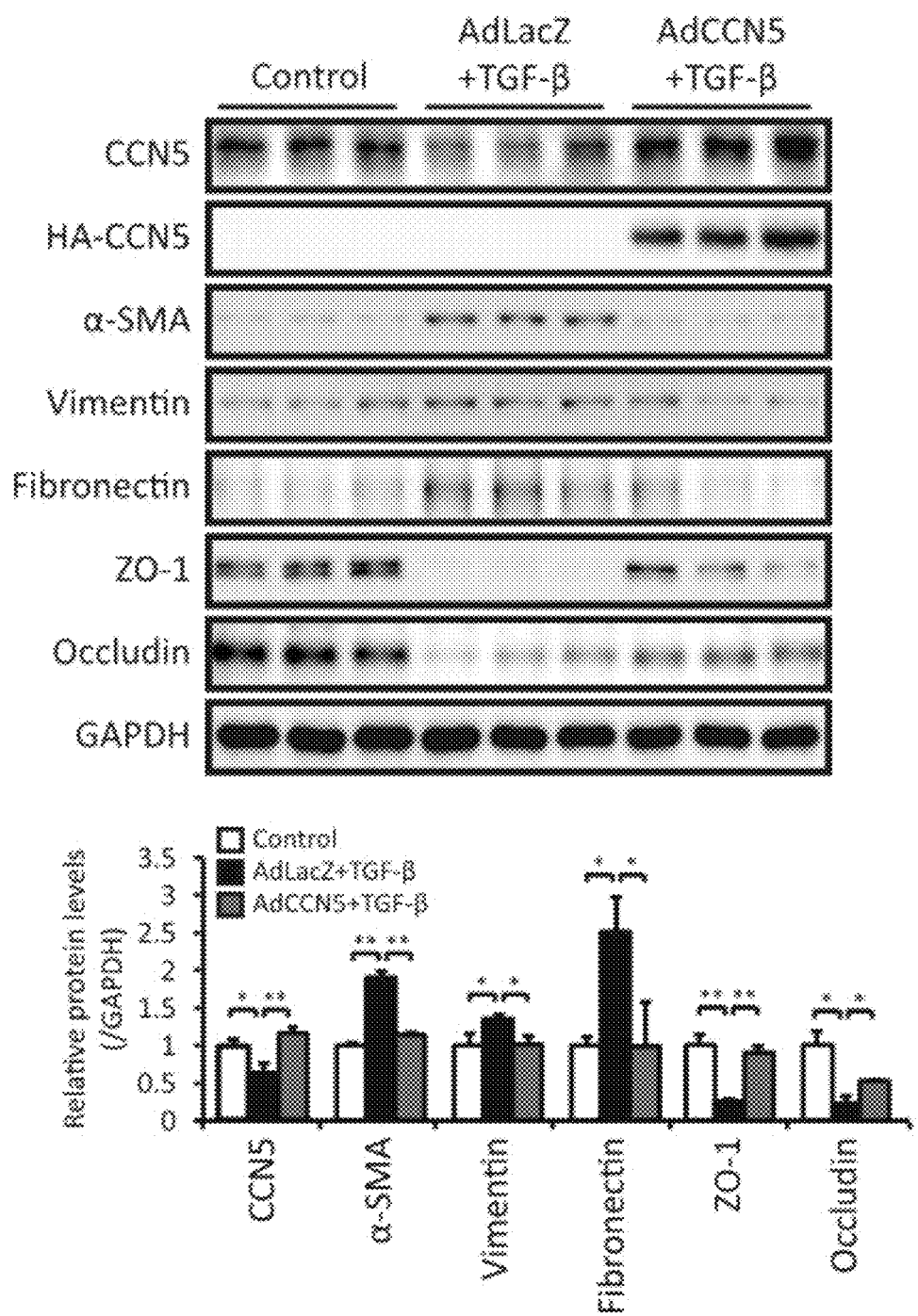
FIG. 2c illustrates results obtained by subjecting ARPE-19 cells to treatment with AdLacZ or AdCCN5, and then observing changes in expression of CCN5, mesenchymal marker proteins, and epithelial marker proteins in the ARPE-19 cells which occur when treated with TGF-β.
Figure 2D:
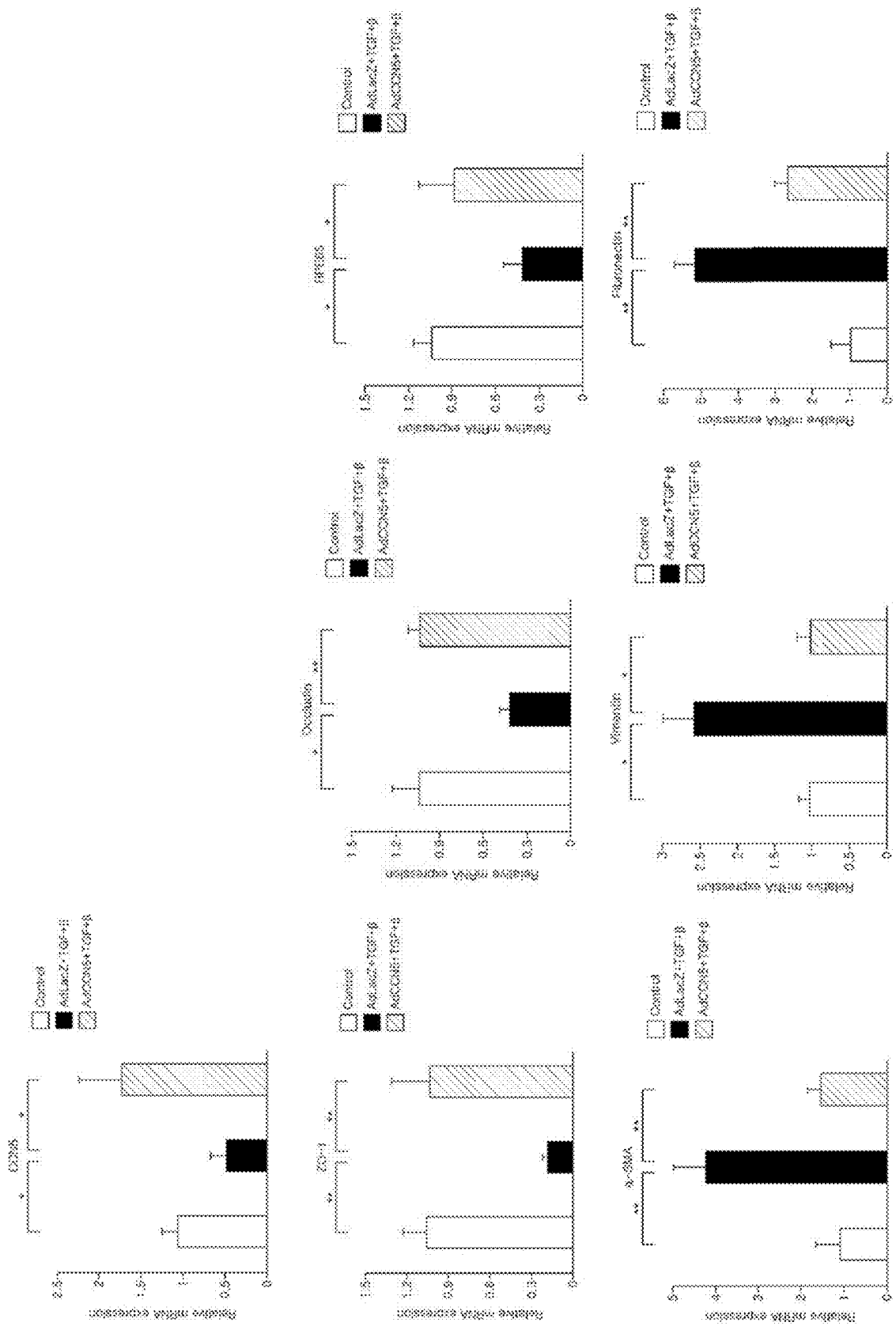
FIG. 2d illustrates results obtained by subjecting ARPE-19 cells to treatment with AdLacZ or AdCCN5, and then identifying, through a quantitative real-time polymerase chain reaction experiment, changes in expression of transcripts of mesenchymal marker proteins and epithelial marker proteins in the ARPE-19 cells which occur when treated with TGF-β.
Figure 2E:
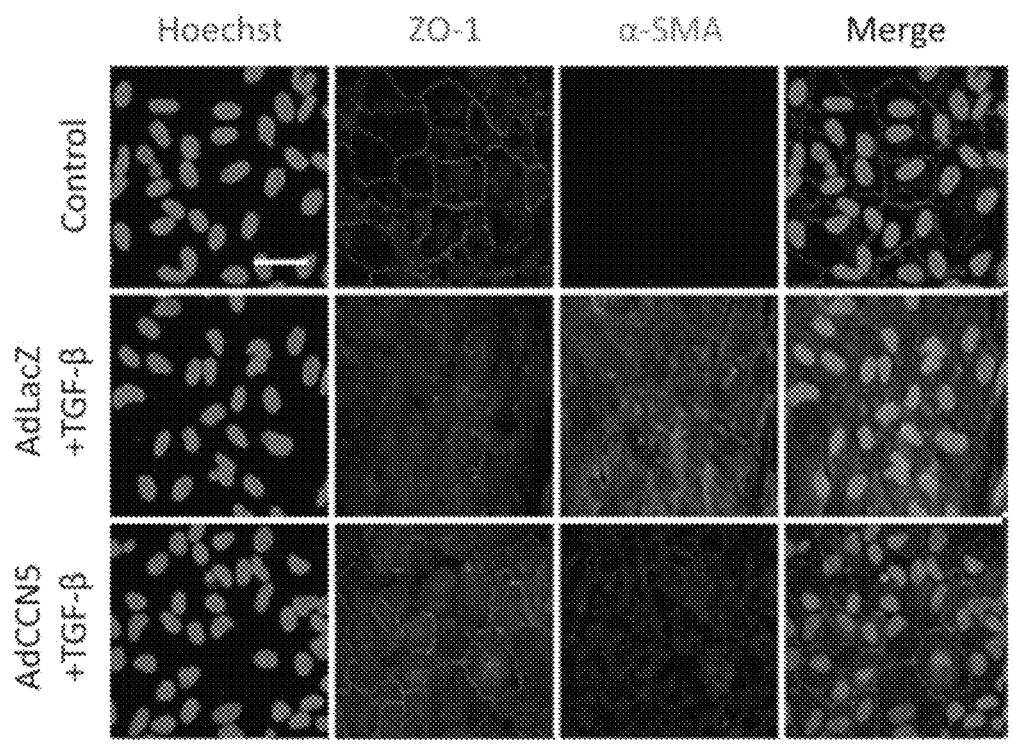
FIG. 2e illustrates results obtained by subjecting ARPE-19 cells to treatment with AdLacZ or AdCCN5, and then observing immunofluorescence images of the ARPE-19 cells, which occur when treated with TGF-β, using anti-ZO-1 antibody, anti-α-SMA antibody, and phalloidin.
Figure 2E:
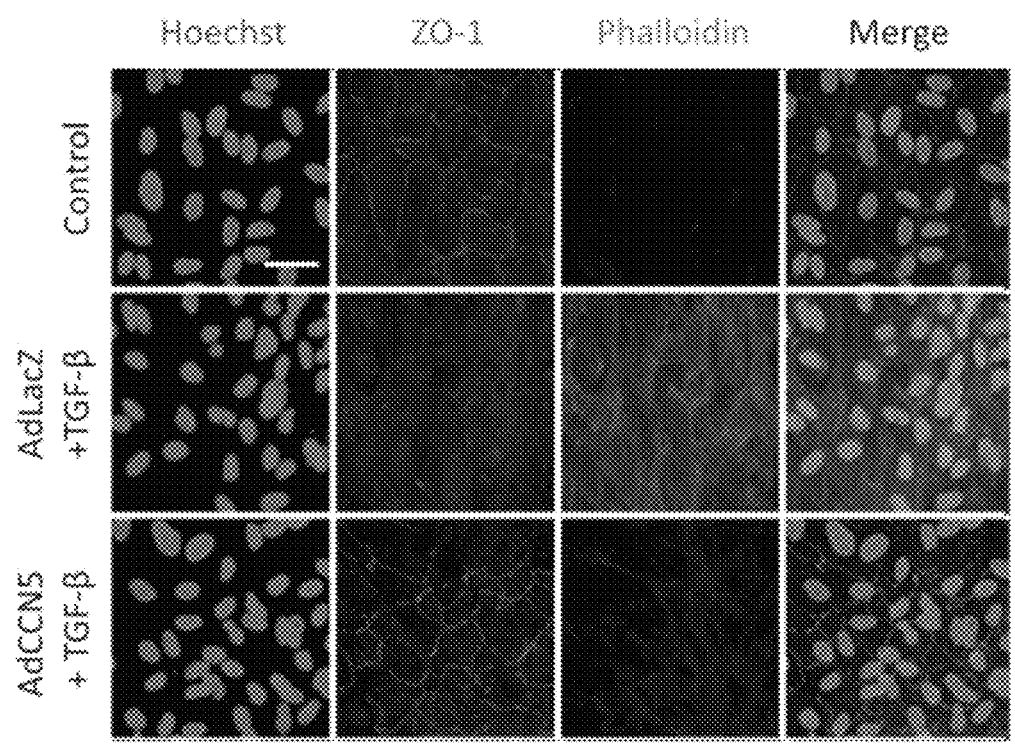

As illustrated in FIG. 2b, AdCCN5 significantly inhibited the morphological changes induced by TGF-β. In addition, as illustrated in FIG. 2c, Western blotting showed that AdCCN5 normalized the TGF-β-induced changes in expression of mesenchymal marker proteins and epithelial marker proteins. These changes were also identified through a quantitative real-time polymerase chain reaction experiment (FIG. 2d). In addition, it was found through immunofluorescence staining for ZO-1 that a phenomenon, in which tight junction was disrupted by TGF-β, was inhibited by AdCCN5; and it was identified that increased expression of α-SMA and formation of f-actin, induced by TGF-β, were inhibited by AdCCN5 (FIG. 2e).

Figure 2F:
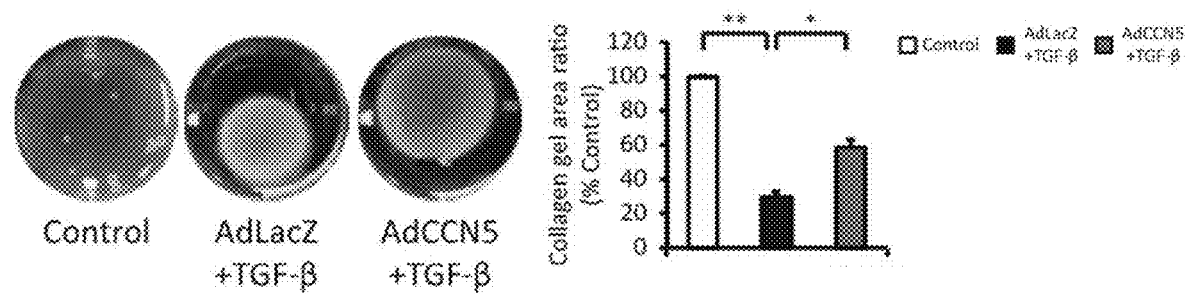
FIG. 2f illustrates results obtained by subjecting ARPE-19 cells to treatment with AdLacZ or AdCCN5, and then observing, through collagen gel contraction assay, changes in contractility of ARPE-19 cells which occur when treated with TGF-β.

On the other hand, increased contractile capacity due to increased expression of α-SMA was a hallmark of fibrotic deformation of epithelial cells. The collagen gel contraction assay showed that increased cellular contractility, caused by TGF-β, was significantly decreased by AdCCN5. These results are illustrated in FIG. 2f.

Figure 3:
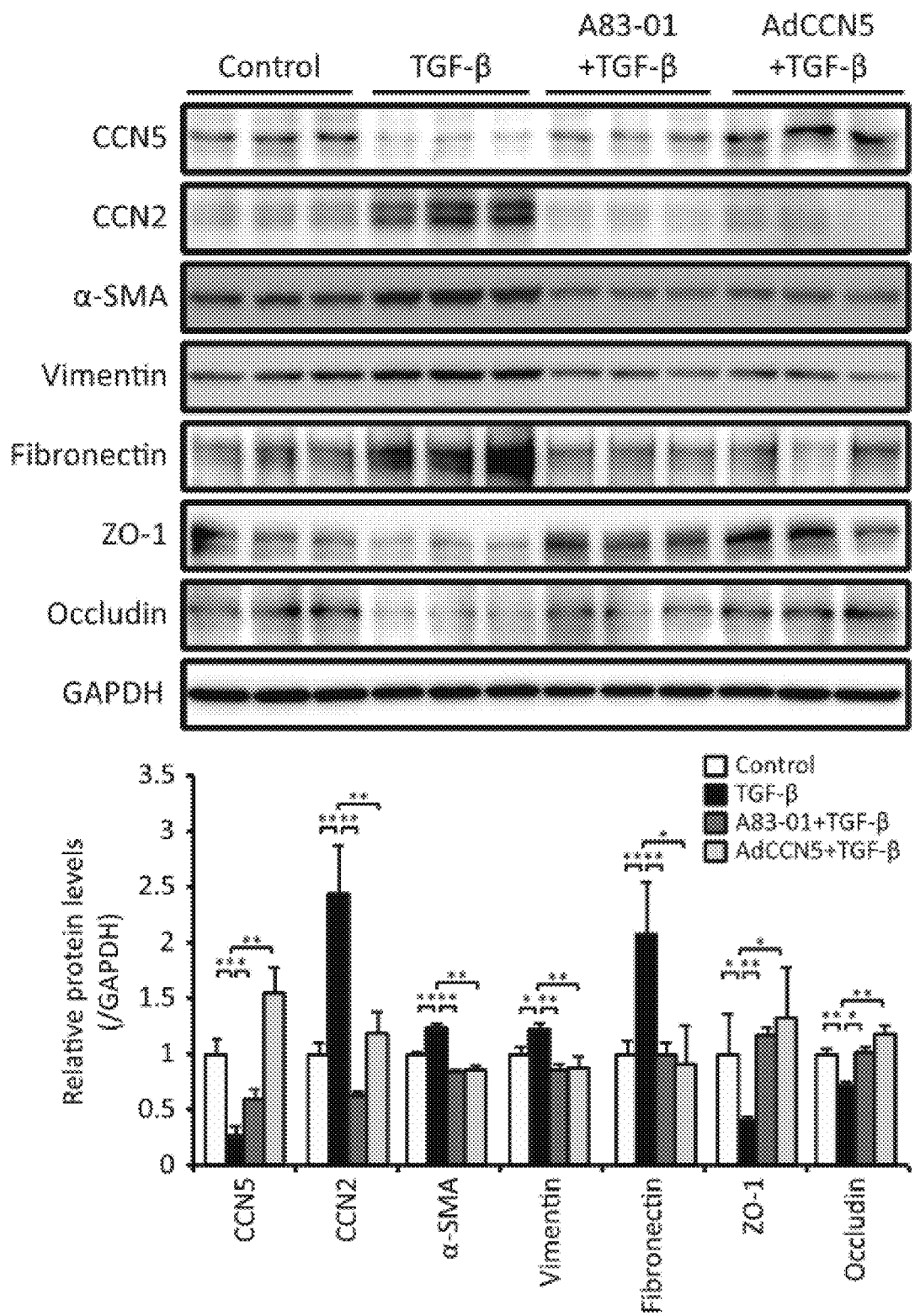
FIG. 3 illustrates results obtained by comparing an inhibitory effect of CCN5 on fibrotic deformation of ARPE-19 cells with that of A83-01, a TGF-β receptor inhibitor.

A83-01 is an inhibitor of TGF-β receptor with its structural similarity to ALK-5 (Activin receptor-like kinase 5) inhibitors. It was observed through Western blotting that human-derived CCN5 inhibited TGF-β-induced fibrotic deformation of ARPE-19 cells to the same level as A83-01 (FIG. 3).

From the above results, it was found that CCN5 prevented fibrotic deformation of ARPE-19 cells induced by TGF-β.

EXPERIMENTAL EXAMPLE 2

Figure 4A:
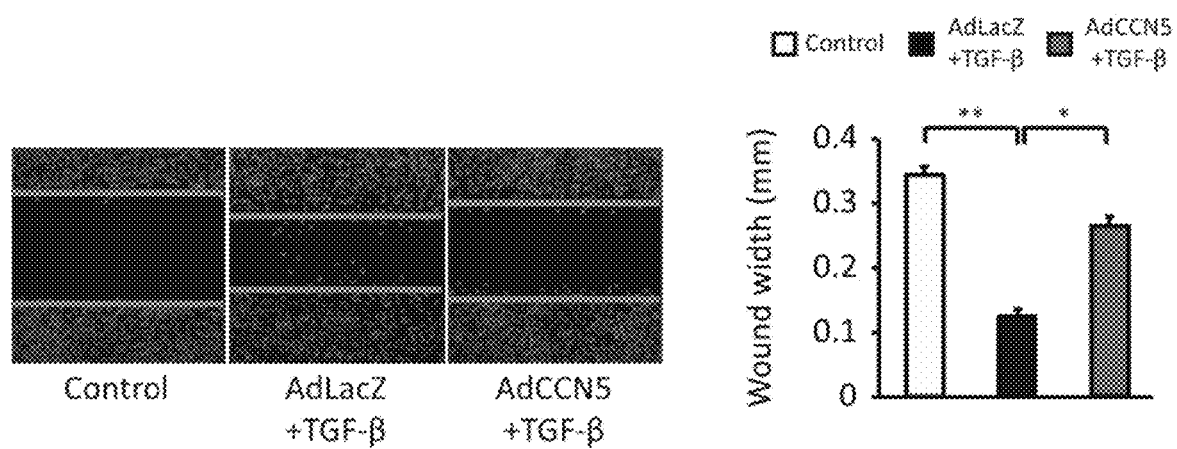
FIG. 4a illustrates results obtained by identifying an effect of AdCCN5 on migration ability of TGF-β-treated ARPE-19 cells.

Identification of Preventive Effect of CCN5 on Functional Deterioration of ARPE-19 Cells TGF-β causes morphological changes as well as functional deterioration of ARPE-19 cells. The ARPE-19 cells were infected with mouse-derived AdCCN5 or AdLacZ for 2 days, and then treated again with TGF-β for 2 days. The cell monolayer was scratched. After 24 hours, the cell monolayer was checked under a microscope. The results are illustrated in FIG. 4a. As illustrated in FIG. 4a, TGF-β increased the migration ability of the ARPE-19 cells, and the migration of the ARPE-19 cells was significantly inhibited by AdCCN5.

Figure 4B:
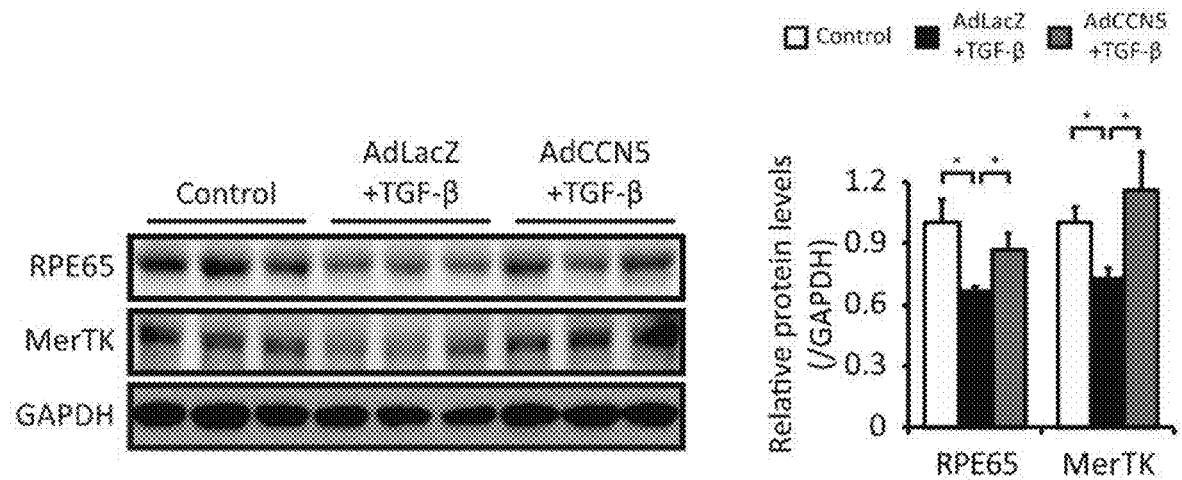
FIG. 4b illustrates results obtained by identifying an effect of AdCCN5 on expression of RPE65 and MerTK in TGF-β-treated ARPE-19 cells.

The enzyme RPE65 is essential for normal vision and serves to convert all-trans retinal into 11-cis retinal. In addition, the protein MerTK plays a critical role in phagocytic activity of RPE cells. Western blotting showed that the expression levels of the enzyme RPE65 and the protein MerTK were significantly decreased upon treatment with TGF-β and that such a decrease was inhibited by mouse-induced AdCCN5. These results are illustrated in FIG. 4b.

The phagocytic function of RPE cells was observed using the pH-sensitive fluorophore-labeled substances, PHRODO® Red-labeled BioParticles, and TAMRA-labeled apoptotic thymocytes. The fluorophore-labeled substances are activated in a case of being engulfed by acidic phagosomes. The RPE cells were incubated with these fluorophore-labeled substances and analyzed by flow cytometry. The results are illustrated in FIGS. 4c and 4d.

Figure 4C:
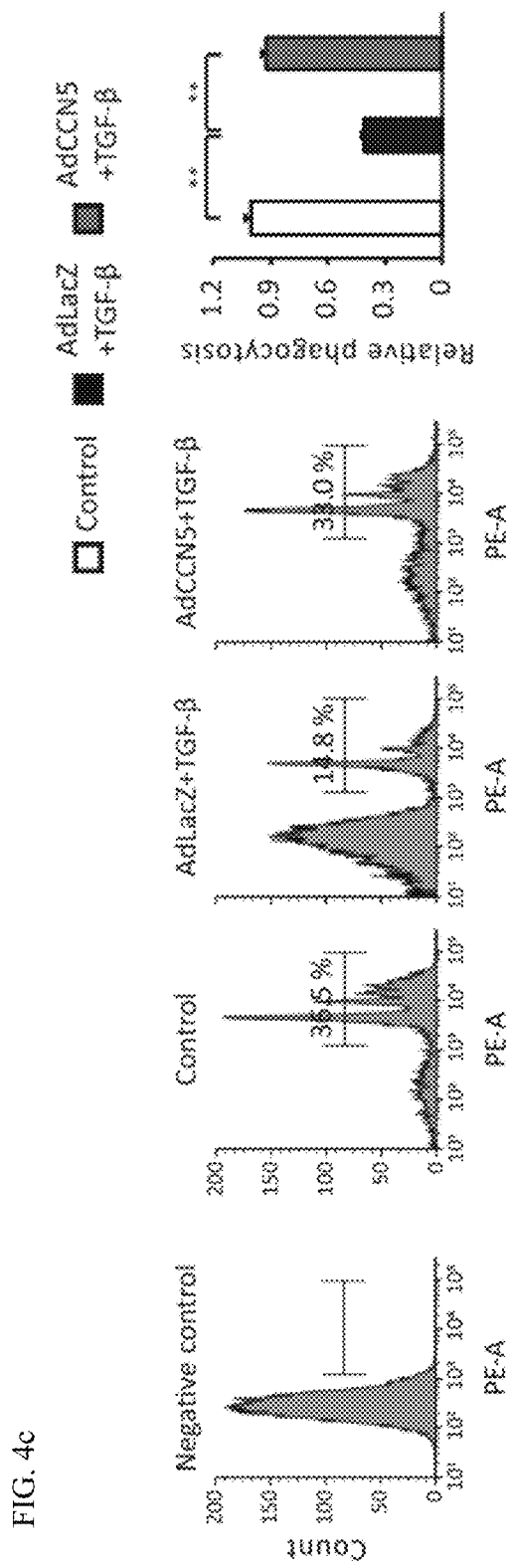
FIG. 4c illustrates results obtained by identifying, using pHrodo Red BioParticles, an effect of AdCCN5 on phagocytosis of TGF-β-treated ARPE-19 cells.
Figure 4D:
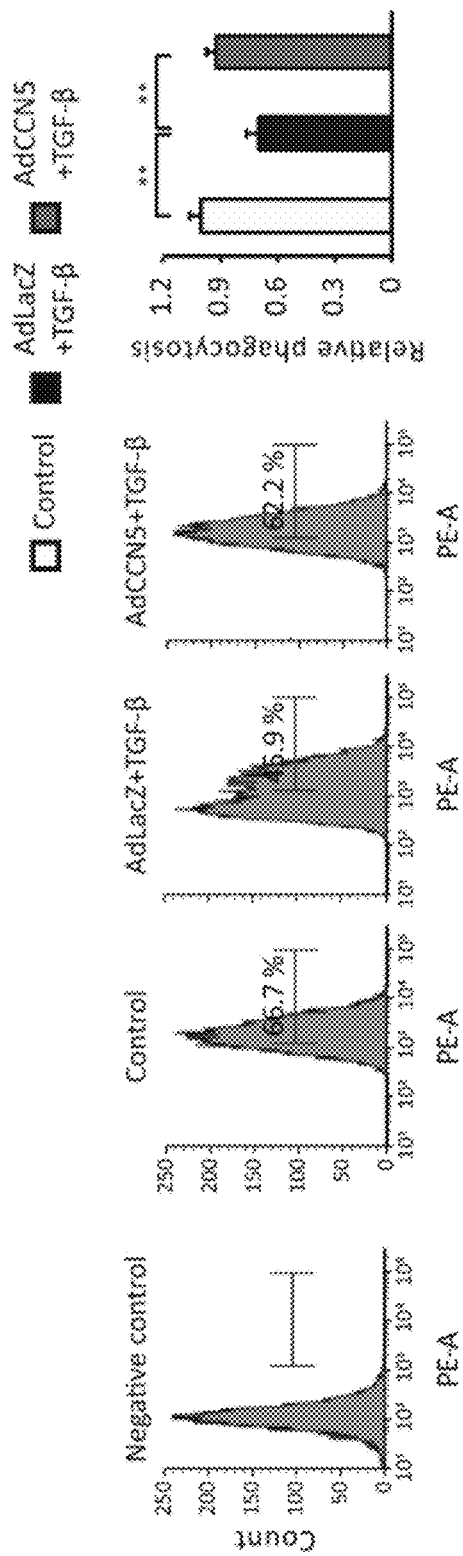
FIG. 4d illustrates results obtained by measuring, using TAMRA-labeled apoptotic thymocytes, an effect of AdCCN5 on phagocytosis of TGF-β-treated ARPE-19 cells.

As illustrated in FIGS. 4c and 4d, the phagocytic activity of the RPE cells was markedly decreased by TGF-β, and this phenomenon was greatly inhibited by mouse-derived AdCCN5. From the above results, it was found that AdCCN5 prevented functional deterioration of ARPE-19 cells induced by TGF-β.

EXPERIMENTAL EXAMPLE 3

Identification of Inhibitory Effect of CCN5 on TGF-β-SMAD Signaling Pathway

Western blotting was used to identify whether CCN5 had an effect on the TGF-β-SMAD signaling pathway. The results are illustrated in FIG. 5.

Figure 5:
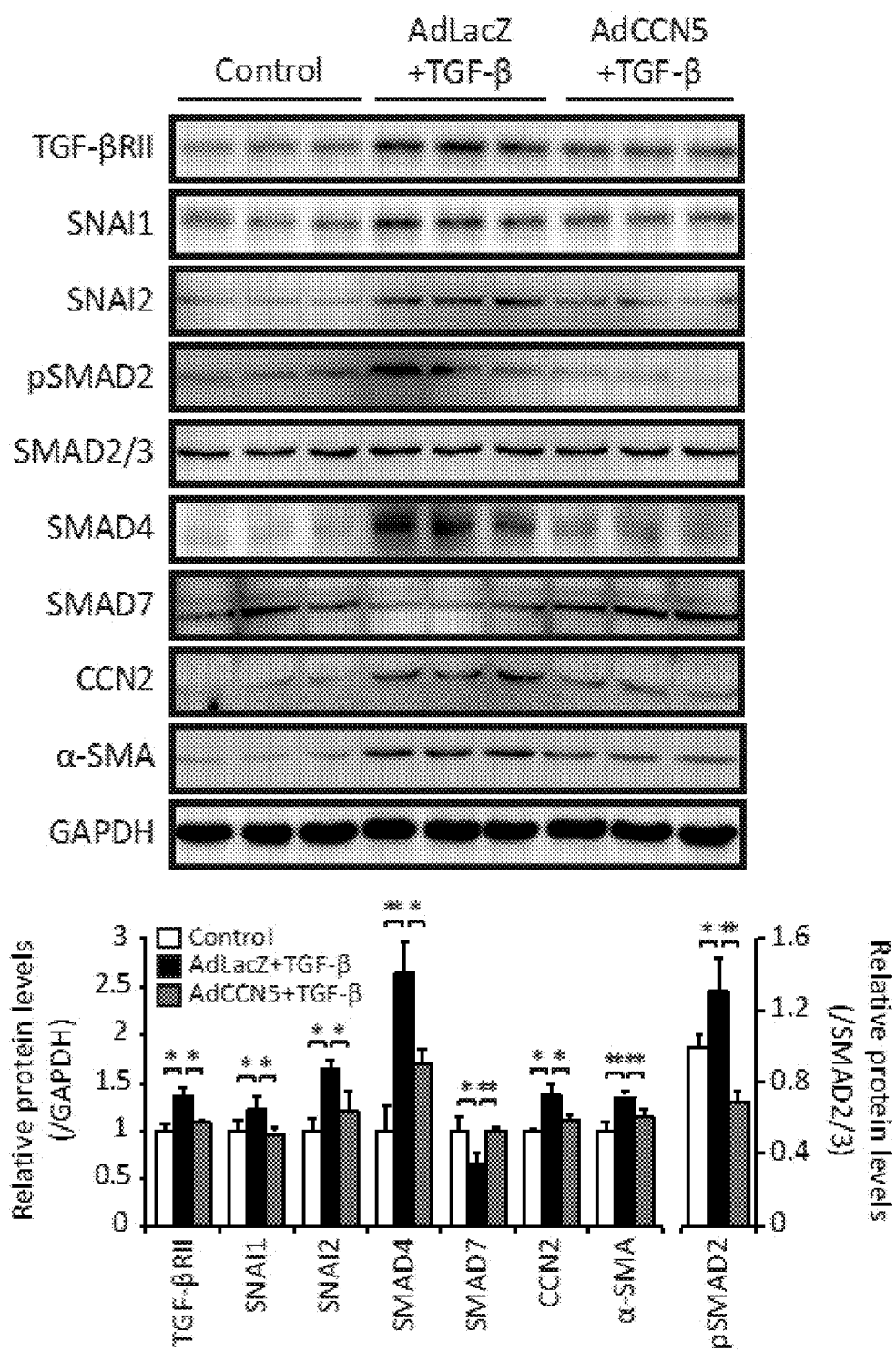
FIG. 5 illustrates results obtained by identifying an effect of AdCCN5 on the TGF-β-SMAD signaling pathway.

As illustrated in FIG. 5, TGF-β up-regulated the expression levels of TGF-βRII, which is a TGF-β receptor, and SNAI1 and SNAI2, which are transcription factors involved in epithelial-mesenchymal transition (EMT) induced by TGF-β. However, the expression of these transcription factors was greatly decreased by AdCCN5. In addition, treatment with AdCCN5 inhibited an increase in phosphorylation of SMAD2 caused by TGF-β, and inhibited an increase in expression of SMAD4 caused by TGF-β. In addition, treatment with AdCCN5 inhibited a decrease in expression of SMAD7 caused by TGF-β. CCN2 is a pro-fibrotic molecule involved in fibrotic deformation of RPE cells and is a downstream target of TGF-β signaling. The expression level of CCN2 was increased by TGF-β, and such an increase was inhibited by AdCCN5. From the above results, it was found that CCN5 inhibited the TGF-β-SMAD signaling pathway.

EXPERIMENTAL EXAMPLE 4

Figure 6A:
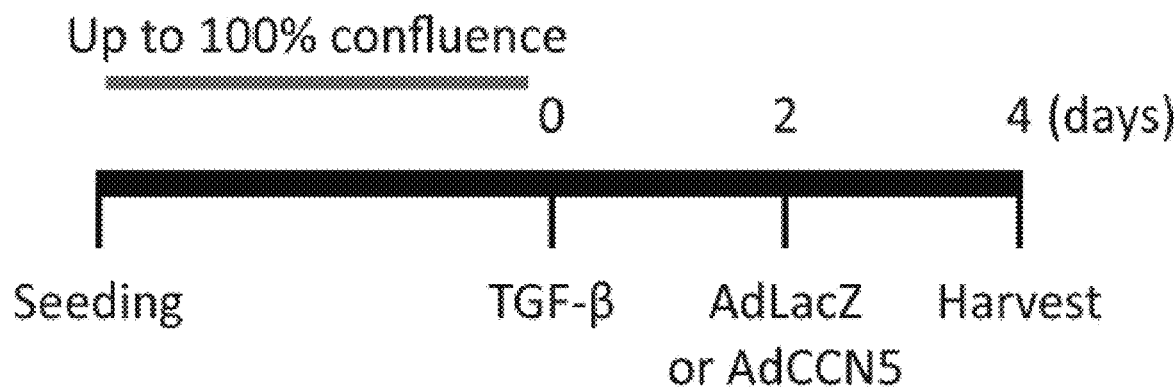
FIG. 6a schematically illustrates an experimental process for identifying whether CCN5 can restore fibrotic deformation of ARPE-19 cells induced by TGF-β.

Identification of Restorative Effect of CCN5 on Fibrotic Deformation of ARPE-19 Cells Experiments were conducted to see if CCN5 could restore the fibrotic deformation of ARPE-19 cells which had already been formed due to TGF-β. For this purpose, the ARPE-19 cells were treated with TGF-β for 2 days, followed by infection with AdCCN5 or AdLacZ (FIG. 6a). The results are illustrated in FIGS. 6b to 6e.

Figure 6B:
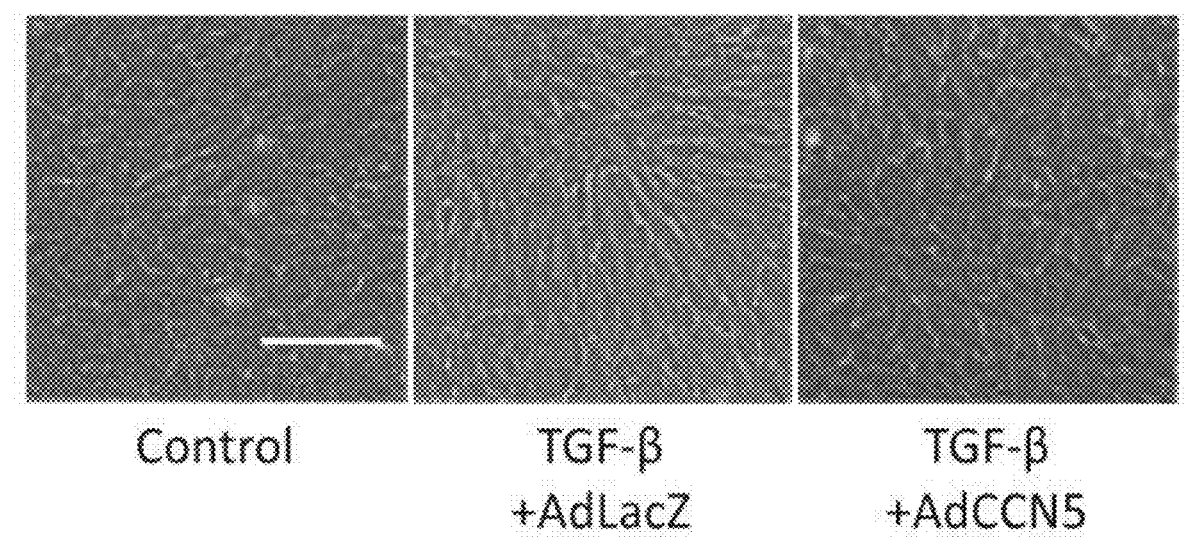
FIG. 6b illustrates results obtained by observing, under a microscope, that the deformation of ARPE-19 cells is restored by AdCCN5.
Figure 6C:
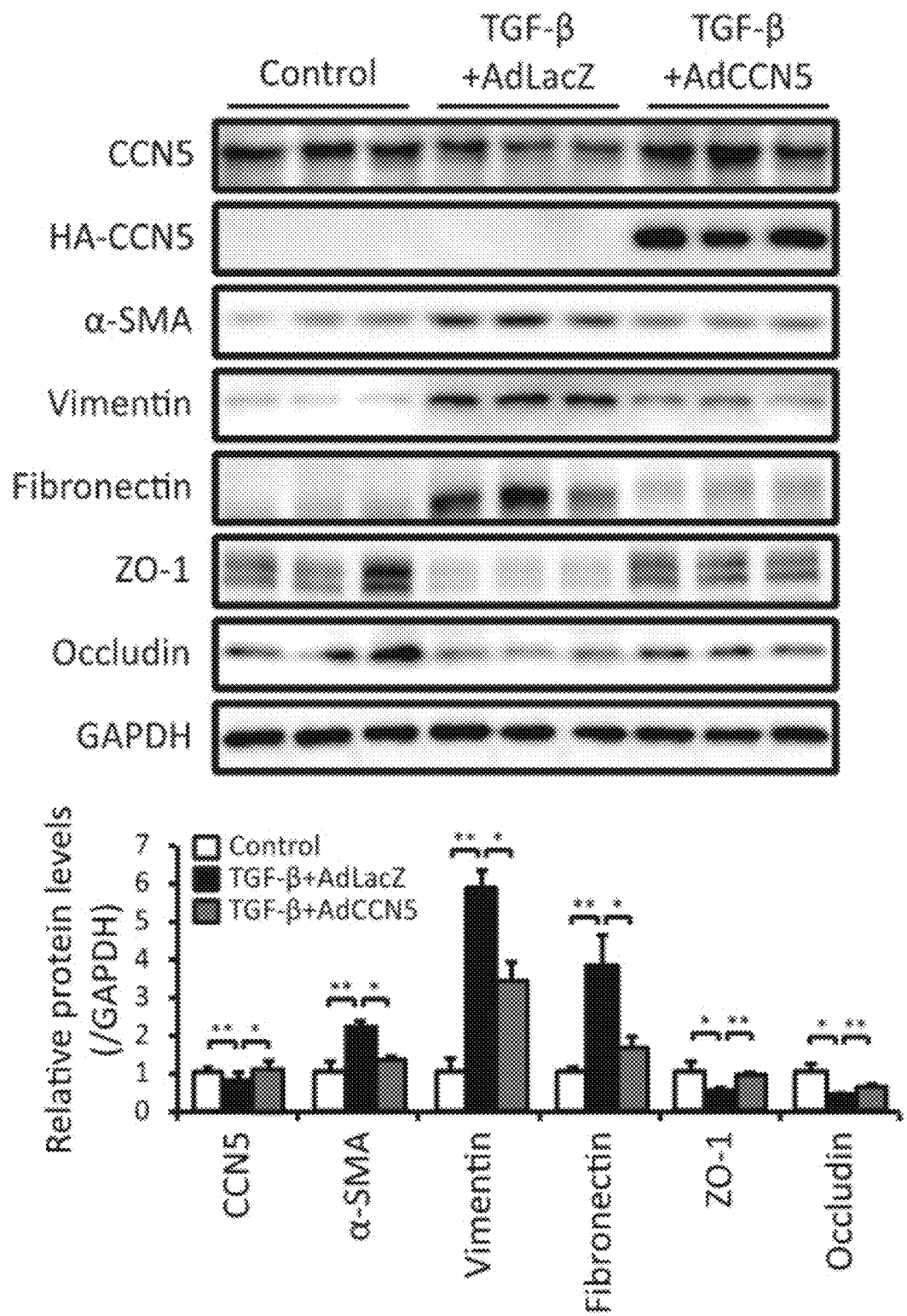
FIG. 6c illustrates results obtained by subjecting ARPE-19 cells to treatment with TGF-β followed by AdCCN5, and then observing changes in expression of CCN5, mesenchymal marker proteins, and epithelial marker proteins in the ARPE-19 cells.
Figure 6D:
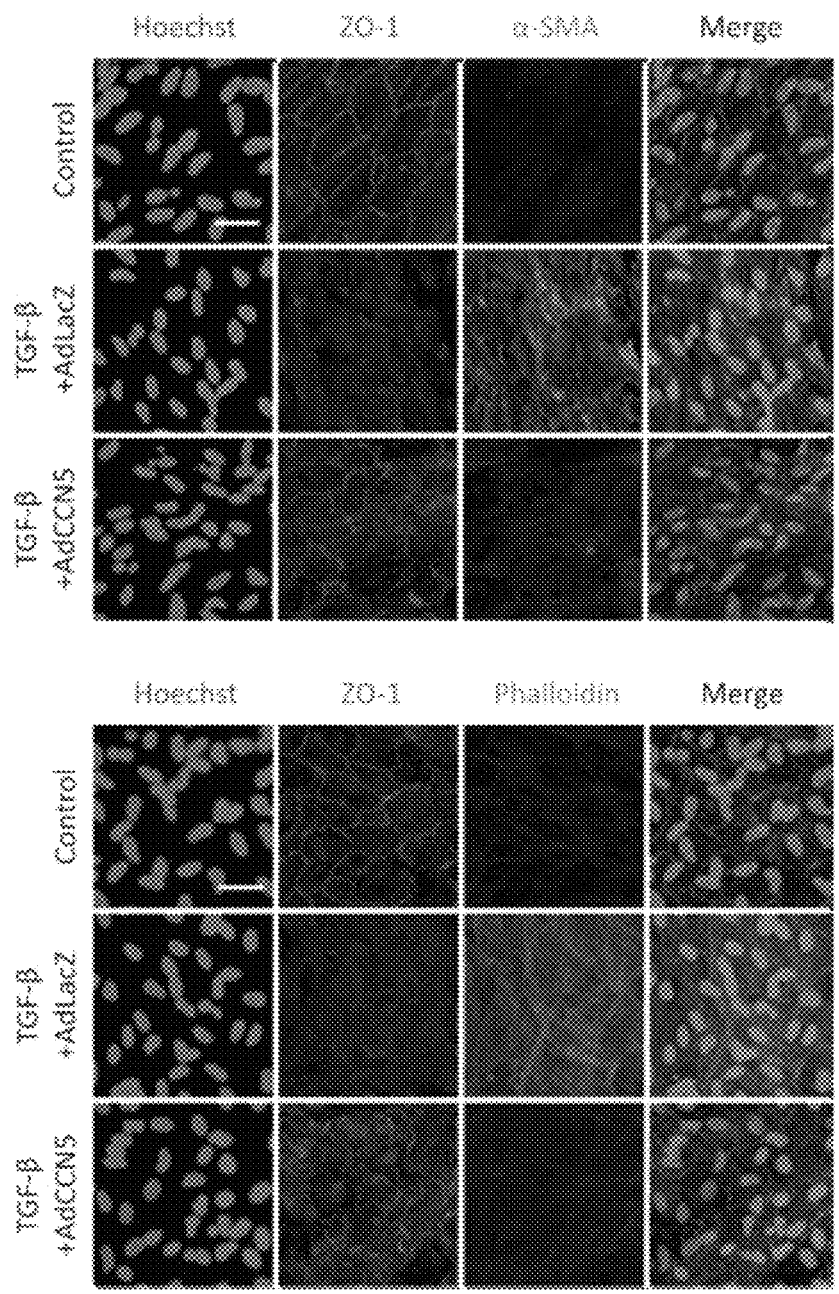
FIG. 6d illustrates results obtained by subjecting ARPE-19 cells to treatment with TGF-β followed by AdCCN5, and then observing the ARPE-19 cells, using anti-ZO-1 antibody, anti-α-SMA antibody, and phalloidin.
Figure 6E:
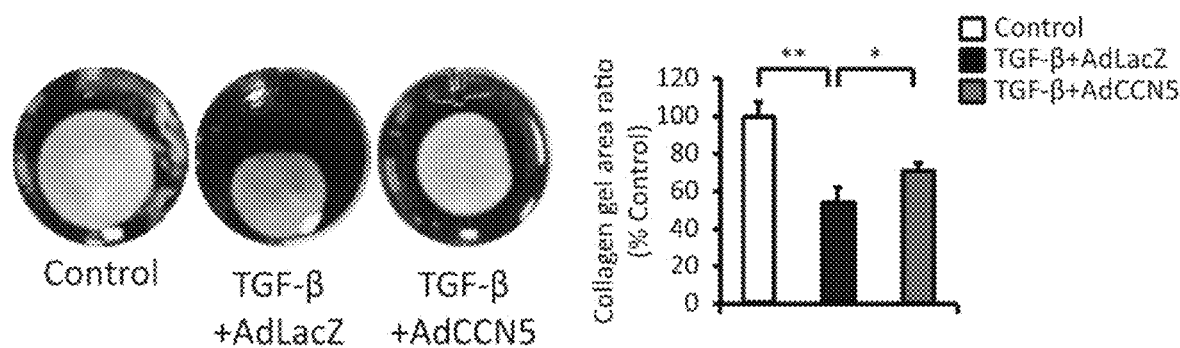
FIG. 6e illustrates results obtained by identifying, through collagen gel contraction assay, an effect of AdCCN5 on normalization of contractility of ARPE-19 cells.

As illustrated in FIG. 6b, the morphological changes in the ARPE-19 cells, induced by TGF-β, were restored to their original shape by AdCCN5. In addition, Western blotting showed that AdCCN5 significantly normalized increased expression of mesenchymal marker proteins (α-SMA, vimentin, and fibronectin) and decreased expression of epithelial marker proteins (ZO-1 and occludin), both increase and decrease being induced by TGF-β (FIG. 6c). In addition, immunofluorescence staining showed that tight junction disrupted by TGF-β was markedly restored by AdCCN5 and that AdCCN5 normalizes increased expression of α-SMA caused by TGF-β. In addition, phalloidin staining revealed that AdCCN5 normalizes an increased level of f-actin caused by TGF-β (FIG. 6d). In addition, collagen gel contraction assay showed that increased cellular contractility caused by TGF-β was significantly decreased by AdCCN5 (FIG. 6e). From the above results, it was found that CCN5 could restore fibrotic deformation of ARPE-19 cells induced by TGF-β.

EXPERIMENTAL EXAMPLE 5

Identification of Restorative Effect of CCN5 on Functional Deterioration of ARPE-19 Cells ARPE-19 cells were treated with TGF-β for 2 days and then infected with human-derived AdCCN5 or AdLacZ.

Then, the function of ARPE-19 cells was analyzed. The results are illustrated in FIGS. 7a to 7d.

Figure 7A:
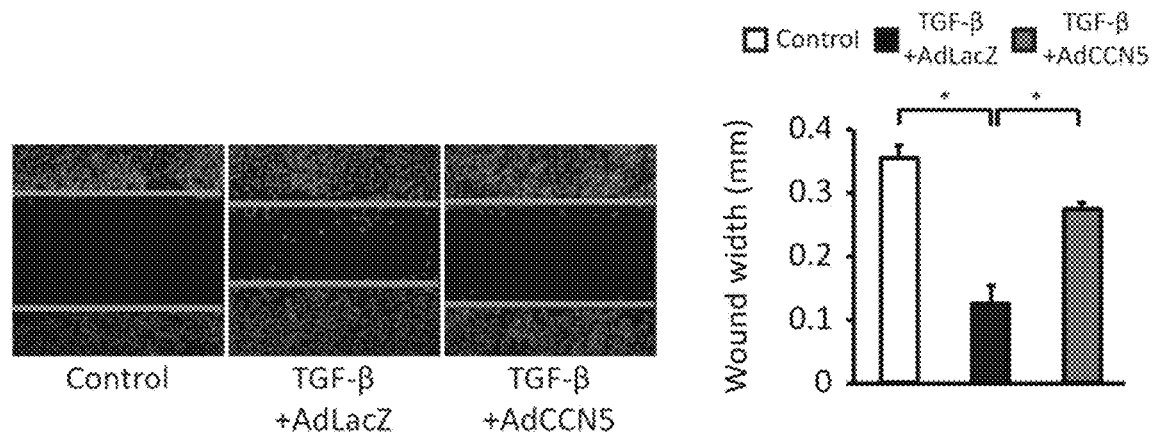
FIG. 7a illustrates results obtained by subjecting ARPE-19 cells to treatment with TGF-β followed by AdCCN5, and then observing that their migration ability is normalized.
Figure 7B:
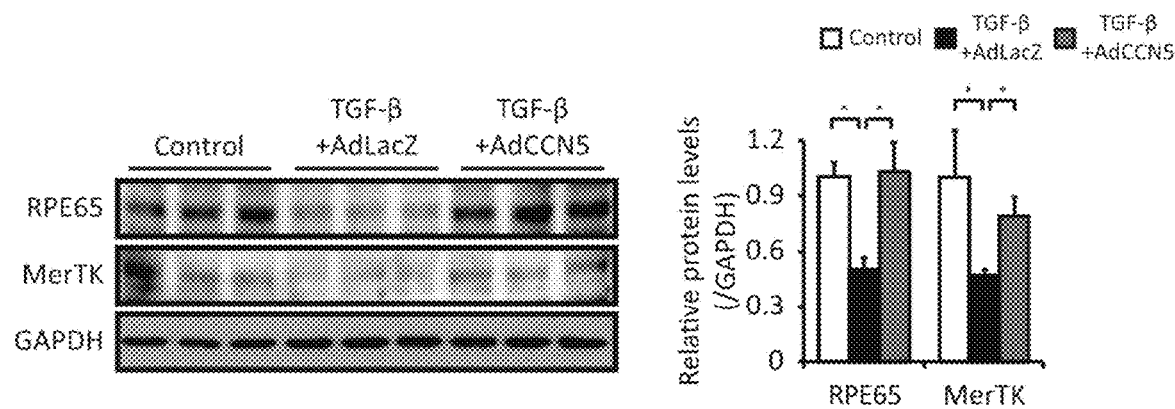
FIG. 7b illustrates results obtained by subjecting ARPE-19 cells to treatment with TGF-β followed by AdCCN5, and then observing that expression of RPE65 and MerTK in the ARPE-19 cells is restored.
Figure 7C:
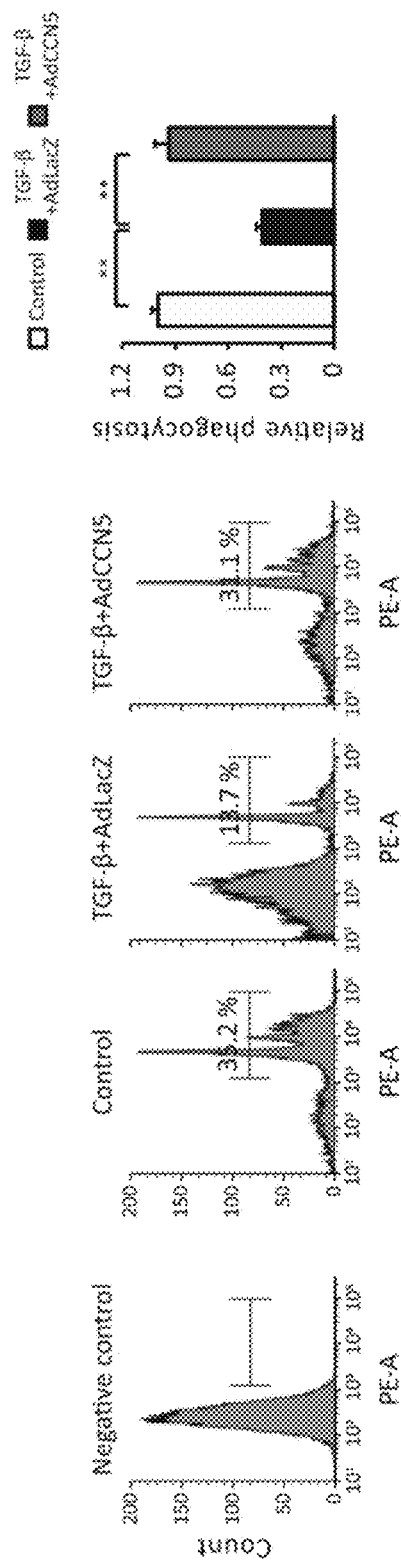
FIG. 7c illustrates results obtained by subjecting ARPE-19 cells to treatment with TGF-β, and then identifying an effect of AdCCN5 on phagocytosis of the ARPE-19 cells, using PHRODO® Red BioParticles.
Figure 7D:
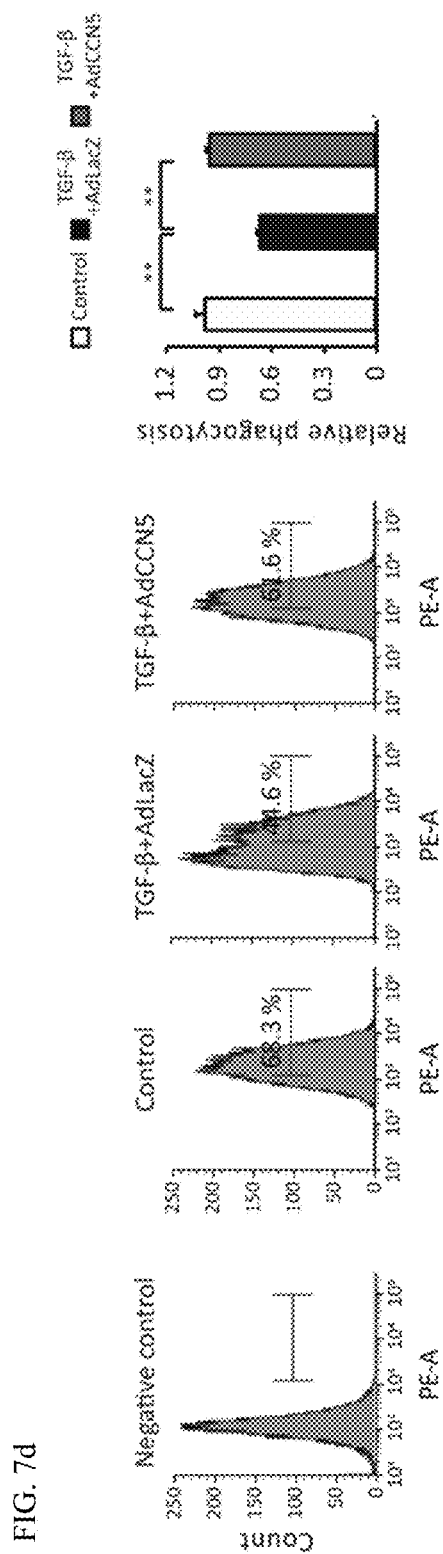
FIG. 7d illustrates results obtained by subjecting ARPE-19 cells to treatment with TGF-β, and then measuring an effect of AdCCN5 on phagocytosis of the ARPE-19 cells, using TAMRA (5(6)-carboxytetramethylrhodamine)-labeled apoptotic thymocytes.

As illustrated in FIG. 7a, improved migration ability of the ARPE-19 cells induced by TGF-β was significantly decreased by AdCCN5. As illustrated in FIG. 7b, AdCCN5 significantly normalized the expression of the proteins RPE65 and MerTK which had been decreased by TGF-β. In addition, flow cytometric analysis showed that the phagocytic activity decreased by TGF-β was markedly restored by AdCCN5 (FIGS. 7c and 7d). From the above results, it was found that CCN5 could restore TGF-β-induced functional defects of ARPE-19 cells to normal.

Figure 8A:
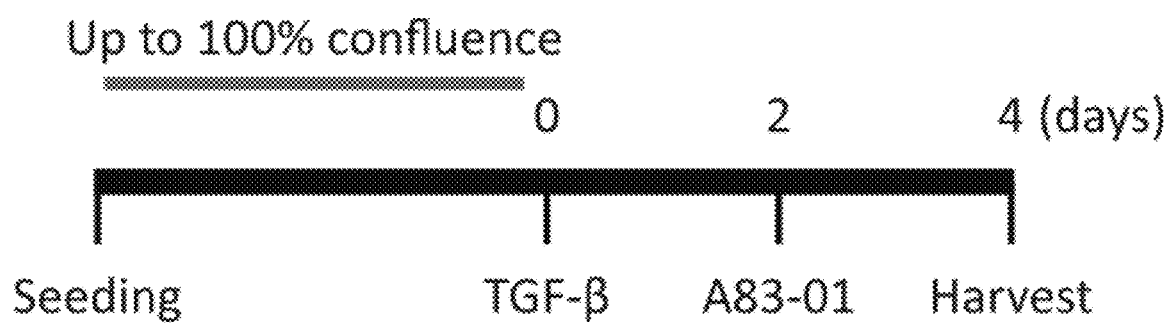
FIG. 8a schematically illustrates an experimental process for identifying an effect of A83-01 in TGF-β-treated ARPE-19 cells.

Two days after treatment of the ARPE-19 cells with TGF-β, treatment with A83-01 of Formula 1 (Sigma-Aldrich, USA), which is a TGF-β inhibitor, was performed (FIG. 8a):

[Formula 1]

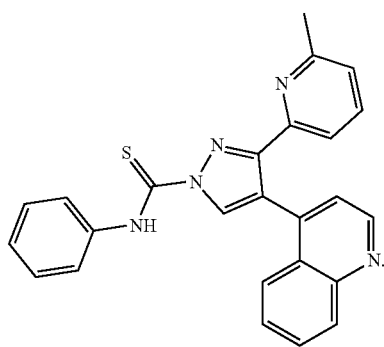

Figure 8B:
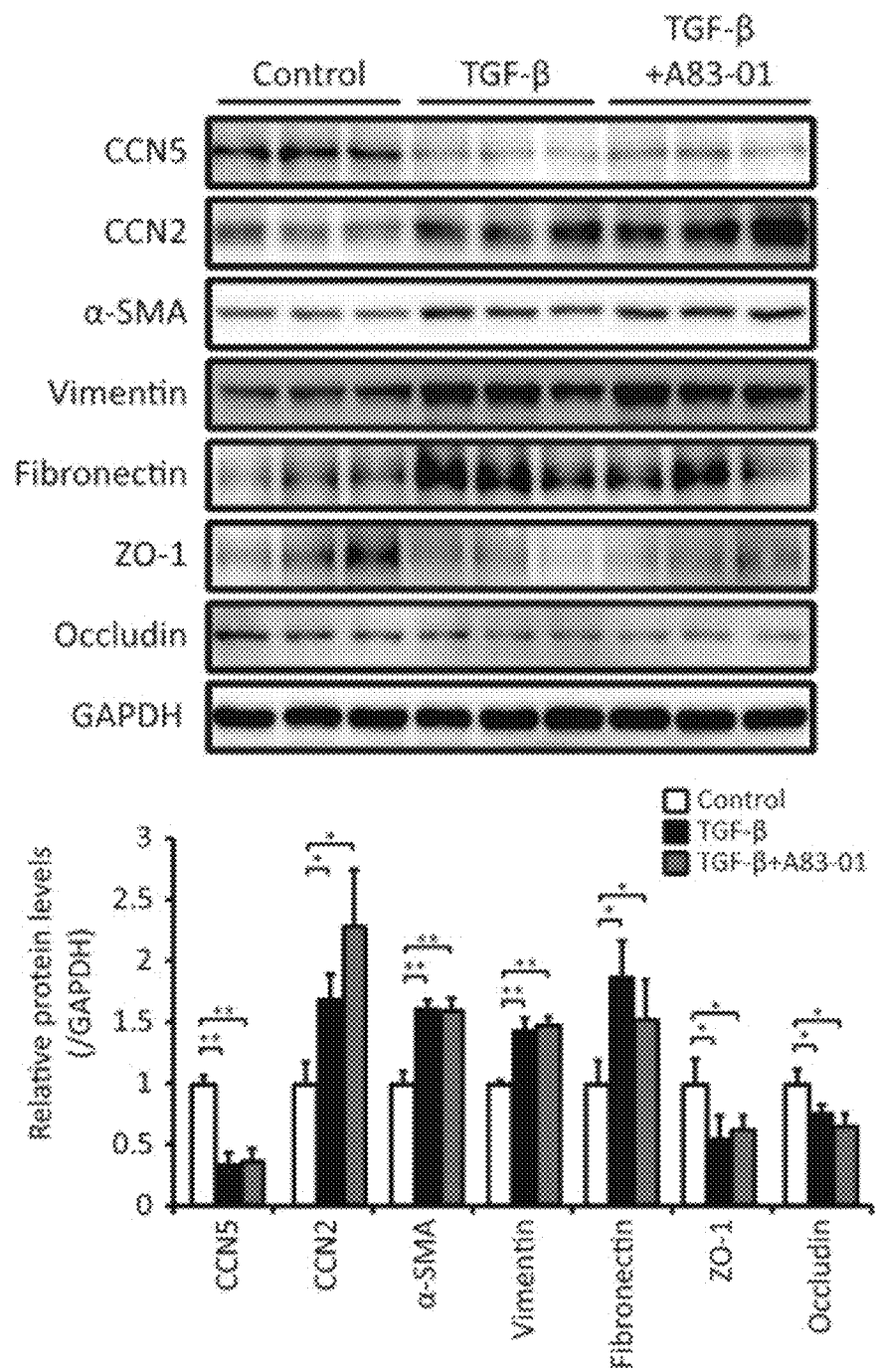
FIG. 8b illustrates results obtained by observing that A83-01 does not normalize changes in expression of CCN5, CCN2, mesenchymal marker proteins, and epithelial marker proteins, which have been caused by TGF-β, in ARPE-19 cells.

The results are illustrated in FIG. 8b. As illustrated in FIG. 8b, unlike CCN5, A83-01 failed to normalize abnormal changes in expression of mesenchymal marker proteins (α-SMA, vimentin, and fibronectin) and epithelial marker proteins (ZO-1 and occludin) (FIG. 8b). From the above results, it was found that inhibition of TGF-β signal transduction could prevent TGF-β-induced fibrotic deformation in ARPE-19 cells and could not restore already-formed fibrotic deformation.

EXPERIMENTAL EXAMPLE 6

Figure 9A:
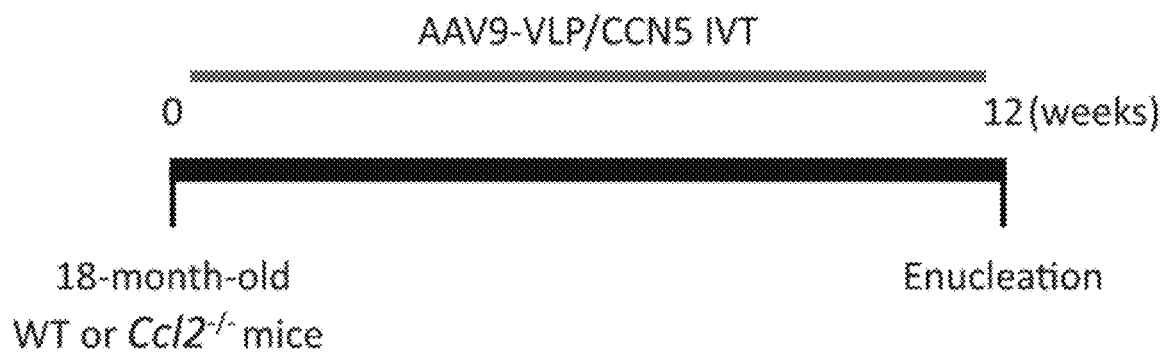
FIG. 9a schematically illustrates a process for measuring a restorative effect of CCN5 on RPE (retinal pigmented epithelium) deformation in $Ccl2^{-/-}$ mice.

Identification of in Vivo Restorative Effect of CCN5 on Fibrotic Deformation of RPE Aged $Ccl2^{-/-}$ mice have characteristics of dry age-related macular degeneration, including fibrotic deformation of RPE. Using intravitreal injection, 18-month-old $Ccl2^{-/-}$ mice were injected with a recombinant adeno-associated virus (AAV9-CCN5) expressing human-derived CCN5 into the right eye and with a control virus (AAV9-VLP) into the left eye. 12 Weeks after injection, the eyes were enucleated to obtain RPE layers and analysis was performed (FIG. 9a). The results are illustrated in FIGS. 9b and 9c.

Figure 9B:
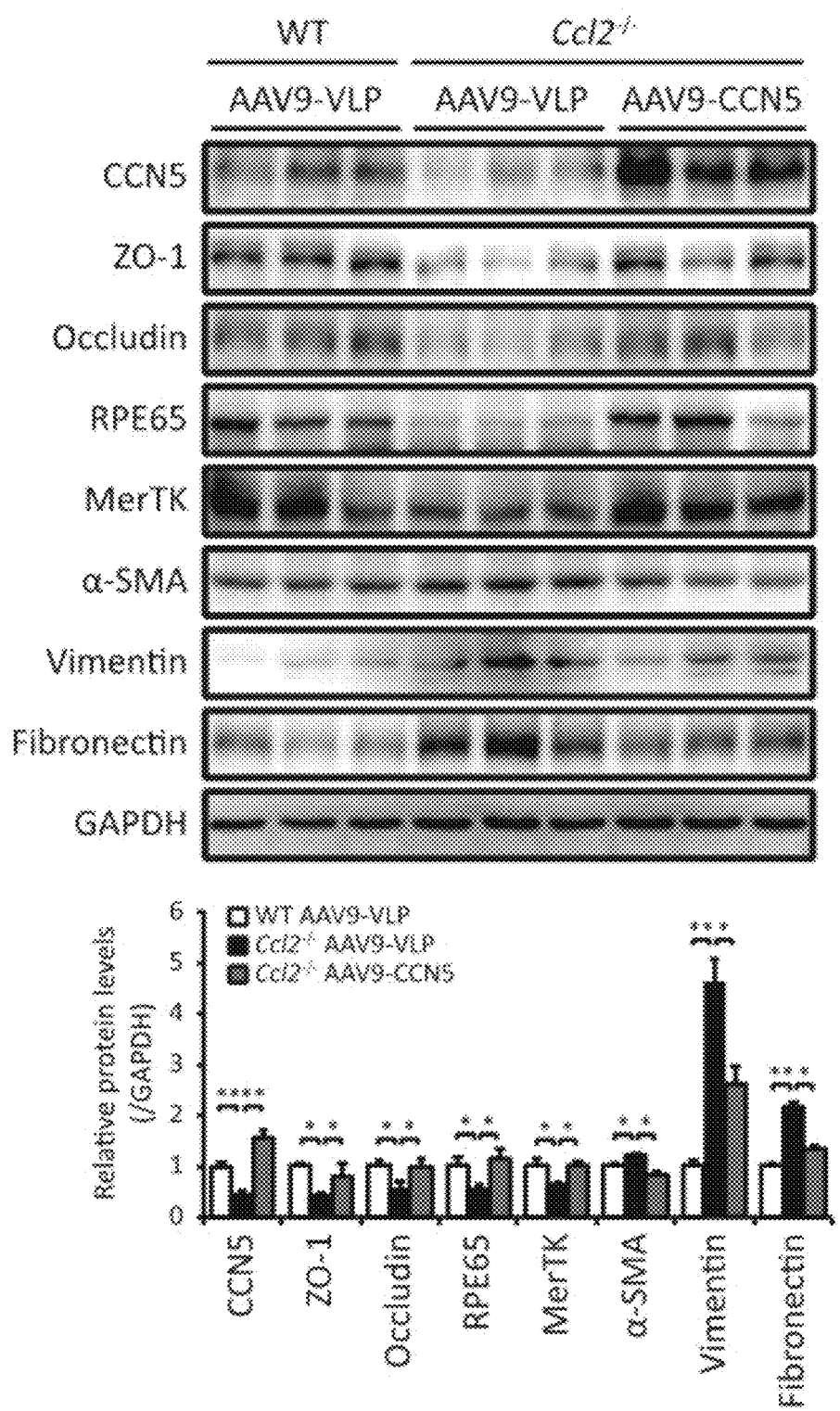
FIG. 9b illustrates results obtained by identifying an effect of AAV9-CCN5 on RPE cells of $Ccl2^{-/-}$ mice, through changes in expression of CCN5, RPE65, MerTK, mesenchymal marker proteins, and epithelial marker proteins.

As illustrated in FIG. 9b, the expression of CCN5 was markedly decreased in the RPE layer of the eye of the $Ccl2^{-/-}$ mice as compared with the RPE layer of the eye of normal (WT) mice, and such a decrease was restored by AAV9-CCN5. The expression of mesenchymal marker proteins (α-SMA, vimentin, and fibronectin) was markedly increased in the RPE of the $Ccl2^{-/-}$ mice, whereas the expression of epithelial marker proteins (ZO-1 and occludin) and RPE function-related marker proteins (RPE65 and MerTK) was greatly decreased. Such changes were restored by AAV9-CCN5 to normal.

In addition, the RPE/choroid/sclera complex was examined to identify unique characteristics of tight junction of the RPE cells. The results are illustrated in FIG. 9c.

Figure 9C:
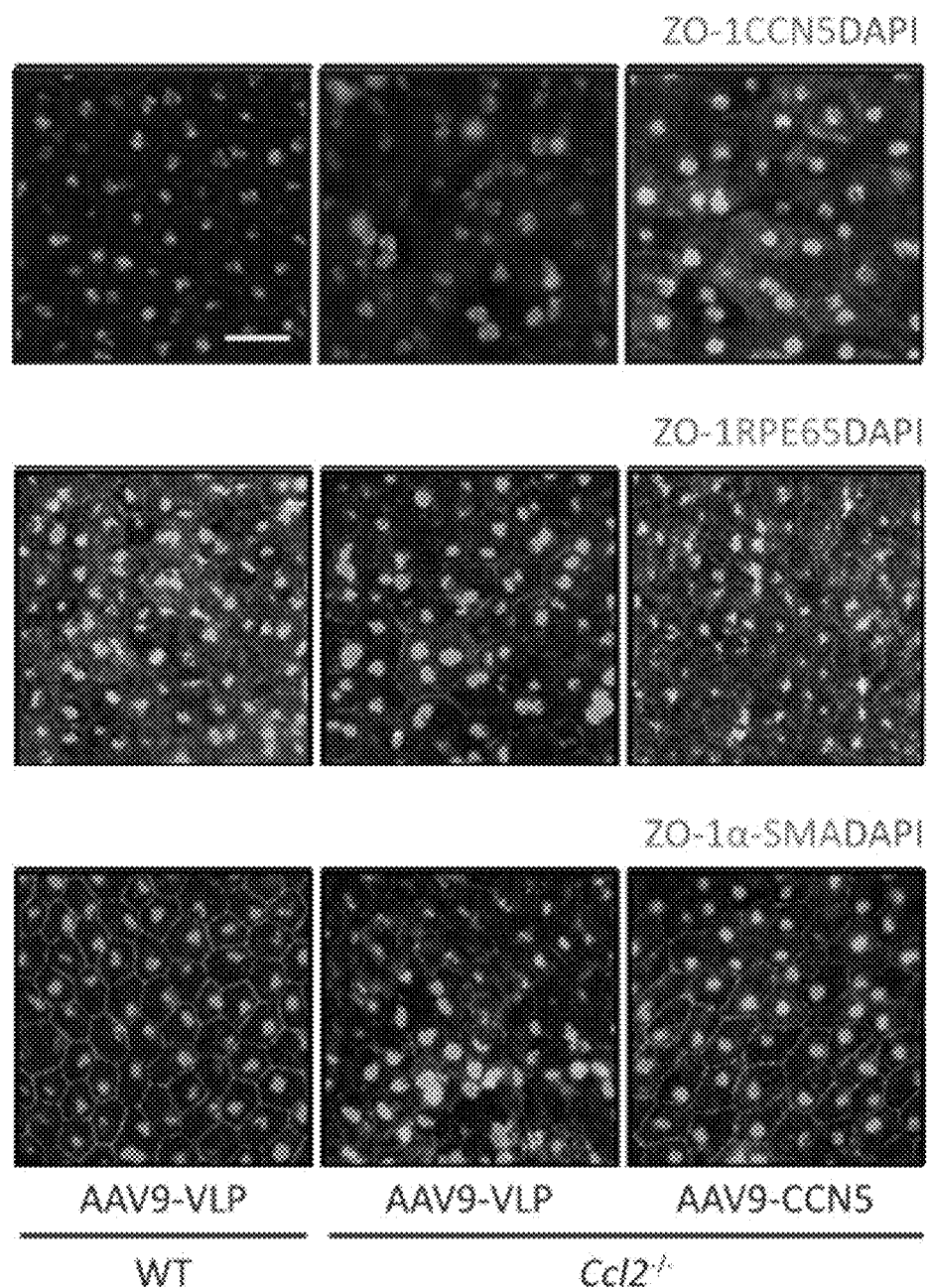
FIG. 9c illustrates results obtained by identifying an effect of AAV9-CCN5 on formation of tight junction in RPE cells of Ccl2$^{-/-}$ mice, through staining with anti-ZO-1 antibody, anti-CCN5 antibody, anti-RPE65 antibody, or anti-α-SMA antibody.

As illustrated in FIG. 9c, it was observed that the tight junction's structure of a well-ordered hexagonal shape as shown in the RPE of 18-month-old normal mice injected with AAV9-VLP had been deformed into an irregular shape in the RPE of age-matched $Ccl2^{-/-}$ mice injected with the control virus. On the contrary, it was identified that in the RPE cells of age-matched $Ccl2^{-/-}$ mice intravitreally injected with AAV9-CCN5, tight junction had been restored to its normal shape. In addition, at the same time, decreased expression of the protein RPE65 was normalized, and the expression of α-SMA was also decreased (FIG. 9c). From the above results, it was found that fibrotic deformation shown in the RPE of aged $Ccl2^{-/-}$ mice was restored by CCN5.

EXPERIMENTAL EXAMPLE 7

Preventive Effect of CCN5 on Fibrotic Deformation of ARPE-19 Cells Caused by Disruption of Tight Junction Cellular tight junction is important for RPE function, and disruption of tight junction is closely correlated with various eye diseases. In a case where RPE cells are treated with a combination of EGTA, EGF, and FGF-2 (hereinafter EEF), tight junction of the RPE cells is disrupted, resulting in loss of normal morphology and function of the RPE.

Figure 10A:
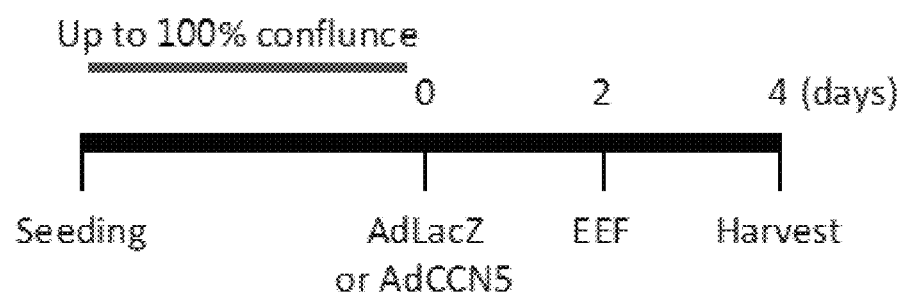
FIG. 10a schematically illustrates a process for identifying whether EEF-induced fibrotic deformation of ARPE-19 cells can be prevented by AdCCN5.
Figure 10B:
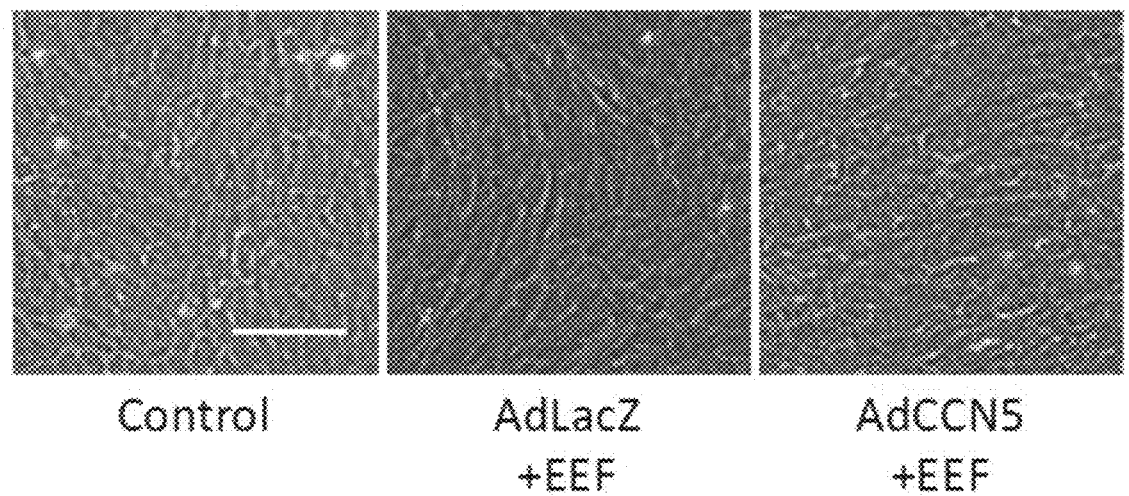
FIG. 10b illustrates results obtained by observing, under a microscope, morphological changes in EEF-treated ARPE-19 cells.
Figure 10C:
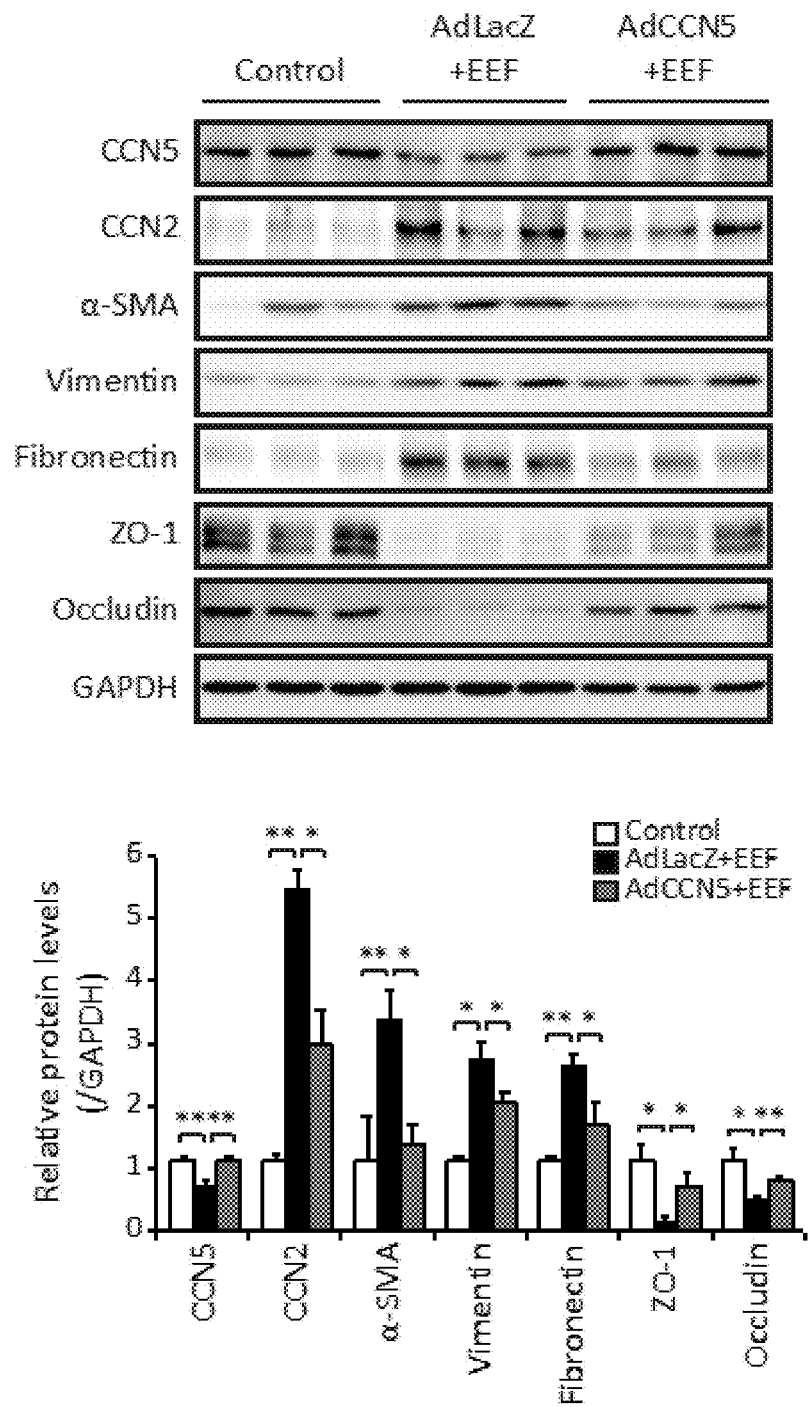
FIG. 10c illustrates results obtained by subjecting AdCCN5-treated ARPE-19 cells to treatment with EEF, and then observing changes in expression of CCN5, CCN2, mesenchymal marker proteins, and epithelial marker proteins in the ARPE-19 cells.
Figure 10D:
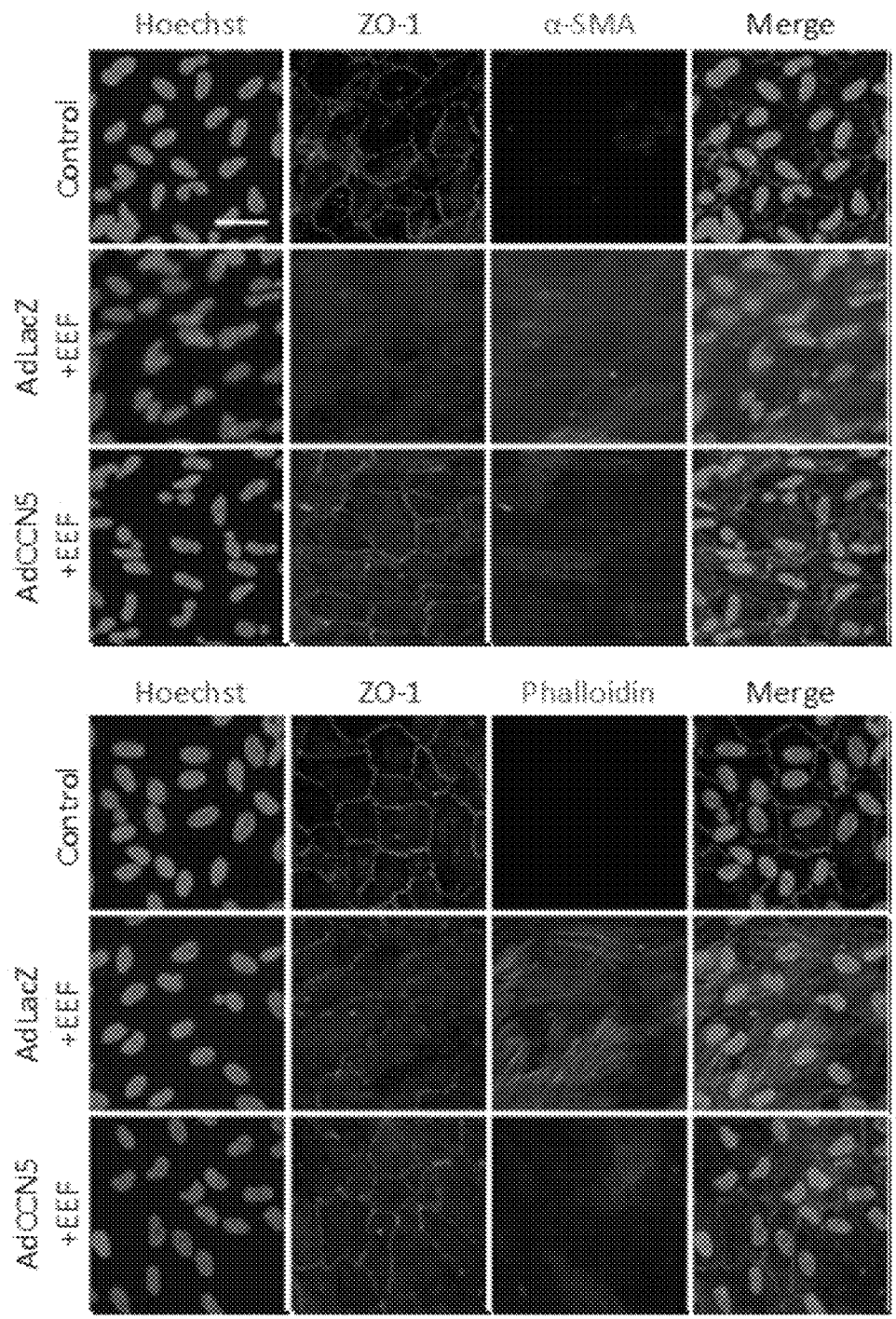
FIG. 10d illustrates results obtained by subjecting AdCCN5-treated ARPE-19 cells to treatment with EEF, and then observing the ARPE-19 cells using anti-ZO-1 antibody, anti-α-SMA antibody, and phalloidin.

ARPE-19 cells were infected with human-derived AdCCN5 or AdLacZ for 2 days, and then treated again with EEF for 2 days (FIG. 10a). The results are illustrated in FIGS. 10b to 10d. As illustrated in FIG. 10b, AdCCN5 significantly inhibited morphological changes induced by the EEF treatment. Western blotting showed that AdCCN5 inhibited increased expression of CCN2 and mesenchymal marker proteins (α-SMA, vimentin, and fibronectin) and inhibited decreased expression of epithelial marker proteins (ZO-1 and occludin), both increase and decrease being induced by the combination of EEF (FIG. 10c). It is a noteworthy result that the expression of CCN5 is decreased by EEF. In addition, immunofluorescence staining showed that AdCCN5 inhibits disruption of tight junction induced by EEF and inhibited increased expression of α-SMA induced by EEF. Phalloidin staining showed that AdCCN5 inhibited f-actin formed by EEF (FIG. 10d). From the above results, it was found that CCN5 prevented fibrotic deformation of ARPE-19 cells which was caused by disruption of tight junction induced by EEF.

EXPERIMENTAL EXAMPLE 8

Figure 11A:
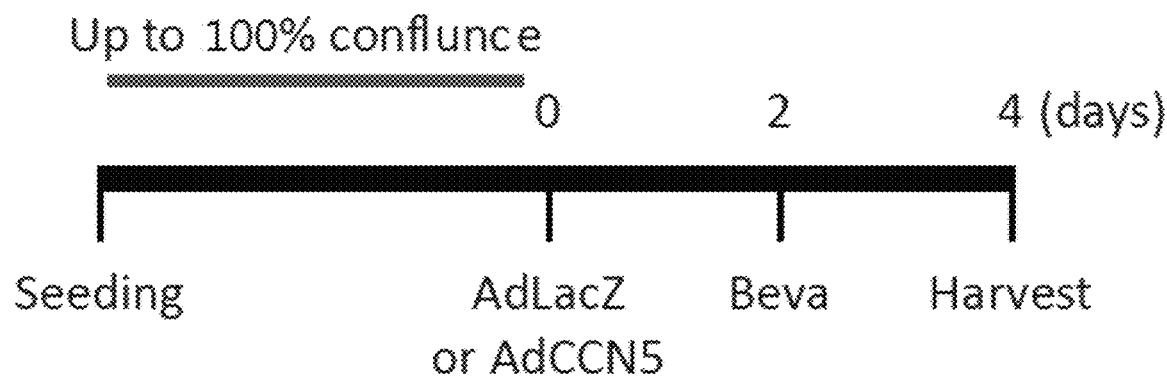
FIG. 11a schematically illustrates a process for identifying whether bevacizumab-induced fibrotic deformation of ARPE-19 cells is prevented by AdCCN5.

Preventive Effect of CCN5 on Fibrotic Deformation of ARPE-19 Cells Induced by Bevacizumab Use of an anti-VEGF drug that inhibits neovascularization is a widely used method for treating wet age-related macular degeneration. However, this method has a side effect of causing morphological and functional changes in RPE cells. Bevacizumab is a first-generation anti-VEGF drug commonly used to treat various cancers or wet age-related macular degeneration. In this experimental example, it was examined whether bevacizumab induced fibrotic deformation in ARPE-19 cells and whether such an adverse result was prevented by human-derived CCN5. The specific experimental process is shown in Example 2, and this experimental process is schematically illustrated in FIG. 11a. The experimental results are illustrated in FIGS. 11b to 11d.

Figure 11B:
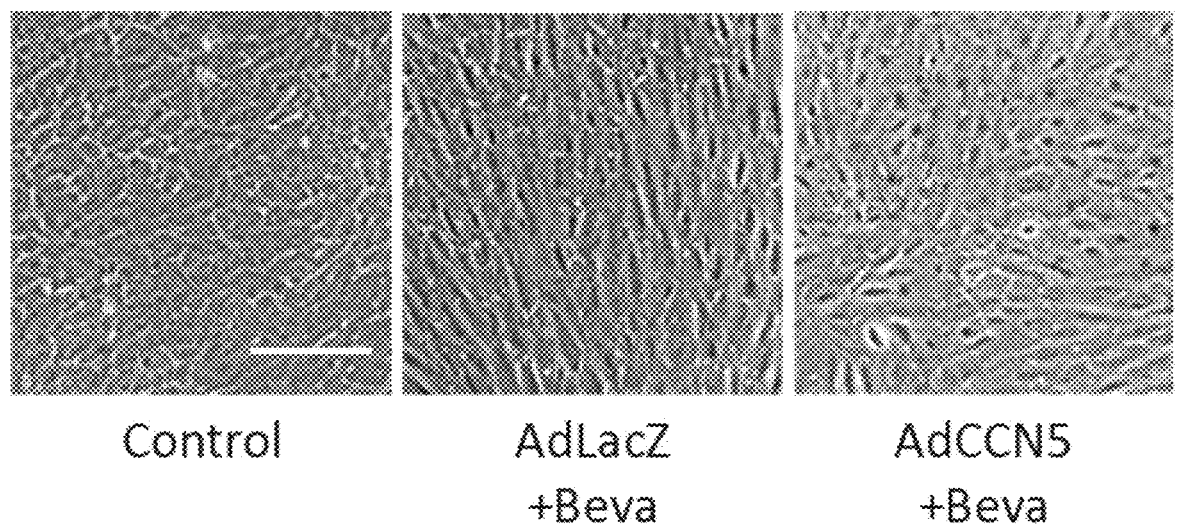
FIG. 11b illustrates results obtained by observing, under a microscope, morphological changes in bevacizumab-treated ARPE-19 cells.
Figure 11C:
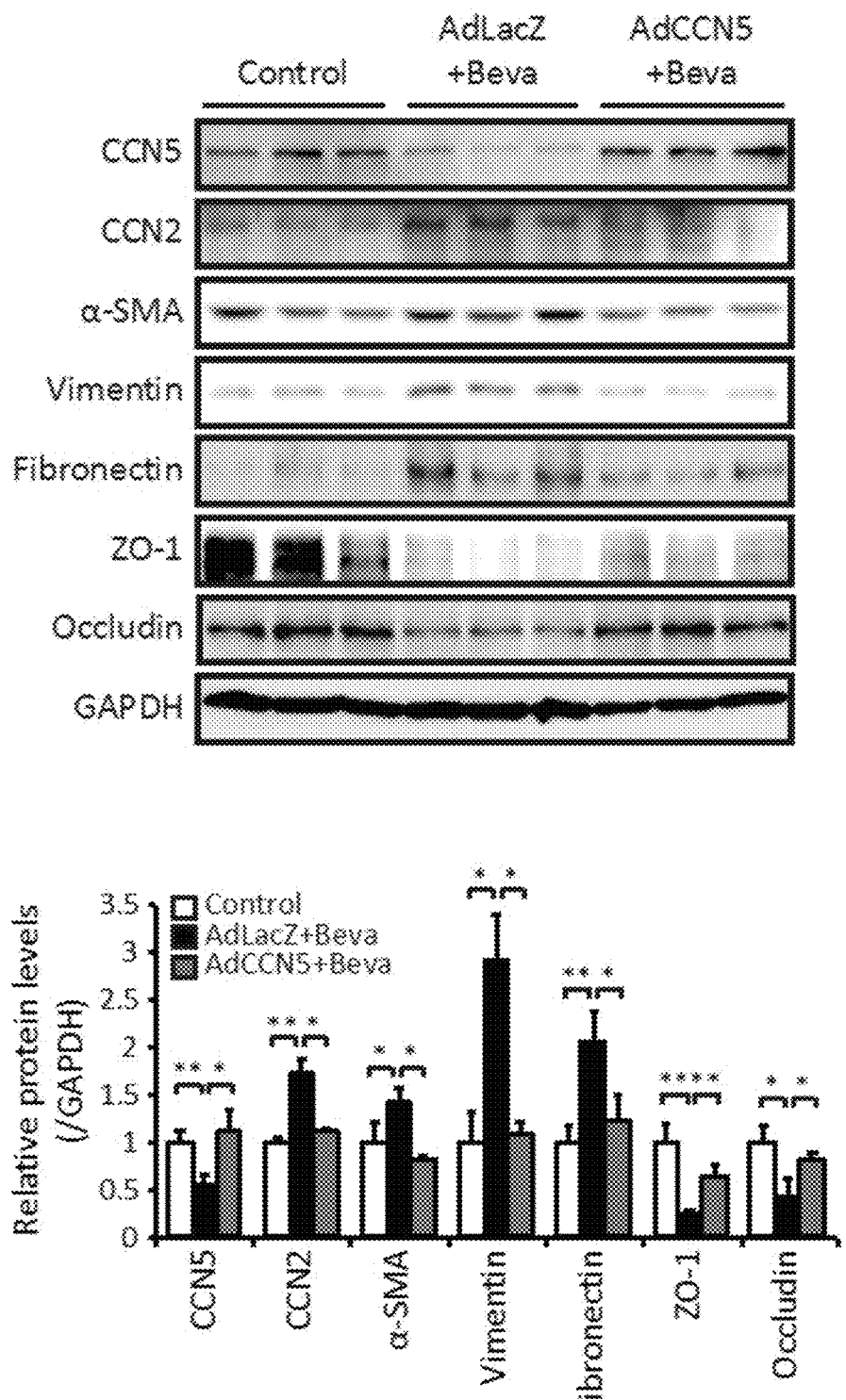
FIG. 11c illustrates results obtained by subjecting AdCCN5-treated ARPE-19 cells to treatment with bevacizumab, and then observing changes in expression of CCN5, CCN2, mesenchymal marker proteins, and epithelial marker proteins in the ARPE-19 cells.
Figure 11D:
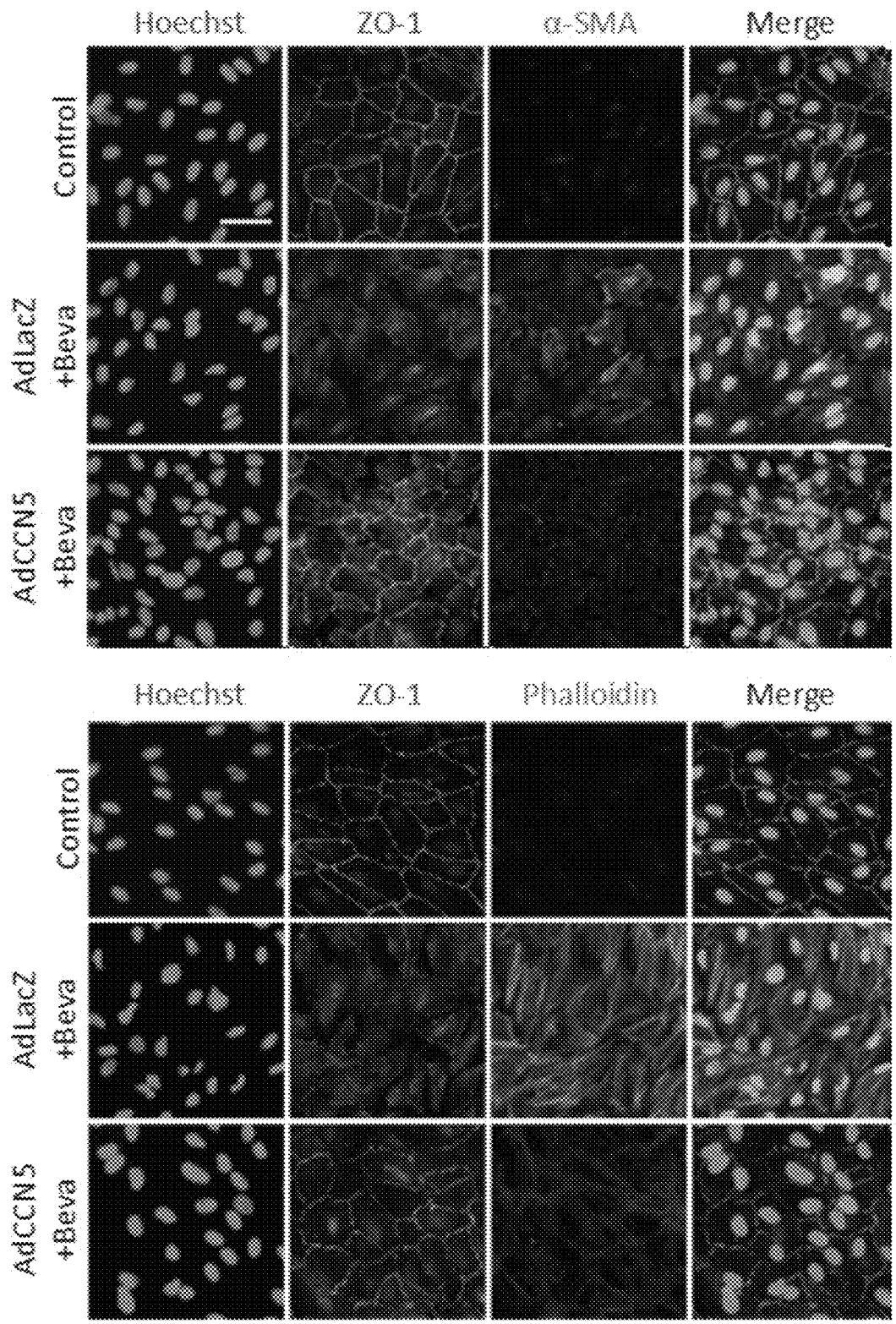
FIG. 11d illustrates results obtained by subjecting AdCCN5-treated ARPE-19 cells to treatment with bevacizumab, and then observing the ARPE-19 cells using anti-ZO-1 antibody, anti-α-SMA antibody, and phalloidin.

As illustrated in FIG. 11b, in a case where the ARPE-19 cells are treated with bevacizumab, the morphology of the cells changed, and this phenomenon was inhibited by AdCCN5. Western blotting showed that AdCCN5 inhibited increased expression of mesenchymal marker proteins (α-SMA, vimentin and fibronectin) and inhibited decreased expression of epithelial marker proteins (ZO-1 and occludin), both increase and decrease being induced by bevacizumab (FIG. 11c). It is a noteworthy result that the expression of CCN5 is decreased by bevacizumab. In addition, immunofluorescence staining showed that AdCCN5 inhibited disruption of tight junction induced by bevacizumab (FIG. 11d). From the above results, it was found that CCN5 prevented fibrotic deformation of ARPE-19 cells induced by bevacizumab.

EXPERIMENTAL EXAMPLE 9

Effect of Modified mRNA Encoding CCN5 and CCN5 Protein

Figure 12A:
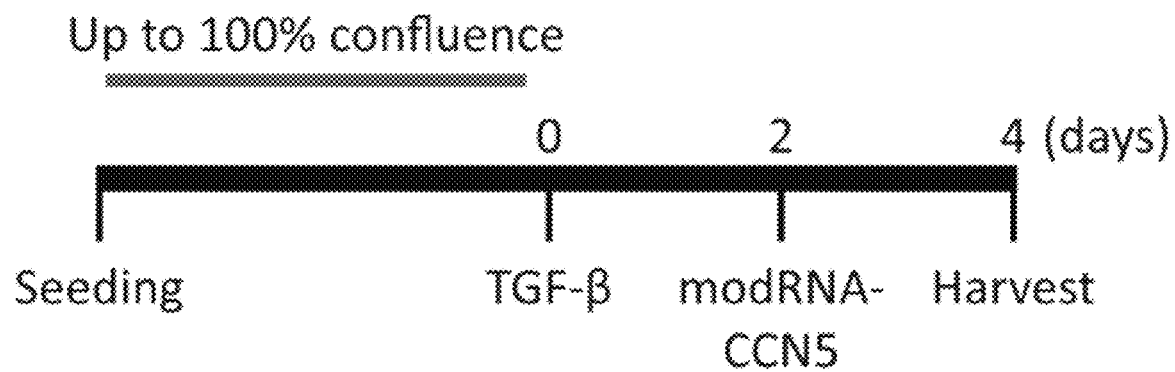
FIG. 12a schematically illustrates a process for identifying whether in a case where ARPE-19 cells are treated with TGF-β and then with modified mRNA encoding CCN5, TGF-β-induced fibrotic deformation of the ARPE-19 cells is restored by CCN5.

Experiments were performed according to the experimental processes schematically illustrated in FIGS. 12a and 13a using modified mRNA encoding human-derived CCN5 (hereinafter referred to as modRNA-CCN5) or purified human-derived CCN5 protein. The results are illustrated in FIGS. 12b to 12c and FIGS. 13b to 13c.

Figure 12B:
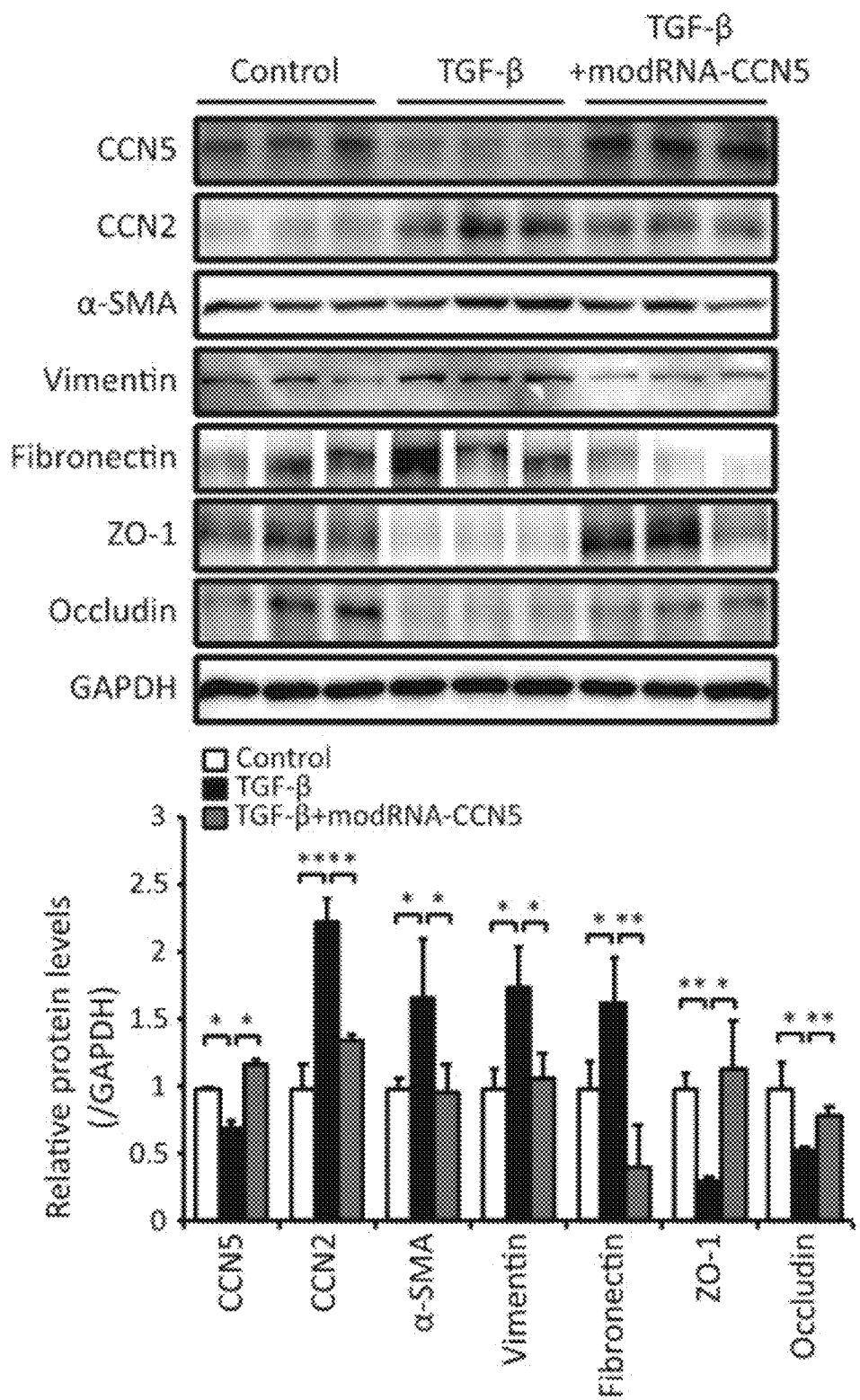
FIG. 12b illustrates results obtained by subjecting TGF-β-treated ARPE-19 cells to treatment with modified mRNA encoding CCN5, and then observing changes in expression of CCN5, CCN2, mesenchymal marker proteins, and epithelial marker proteins in the ARPE-19 cells.
Figure 12C:
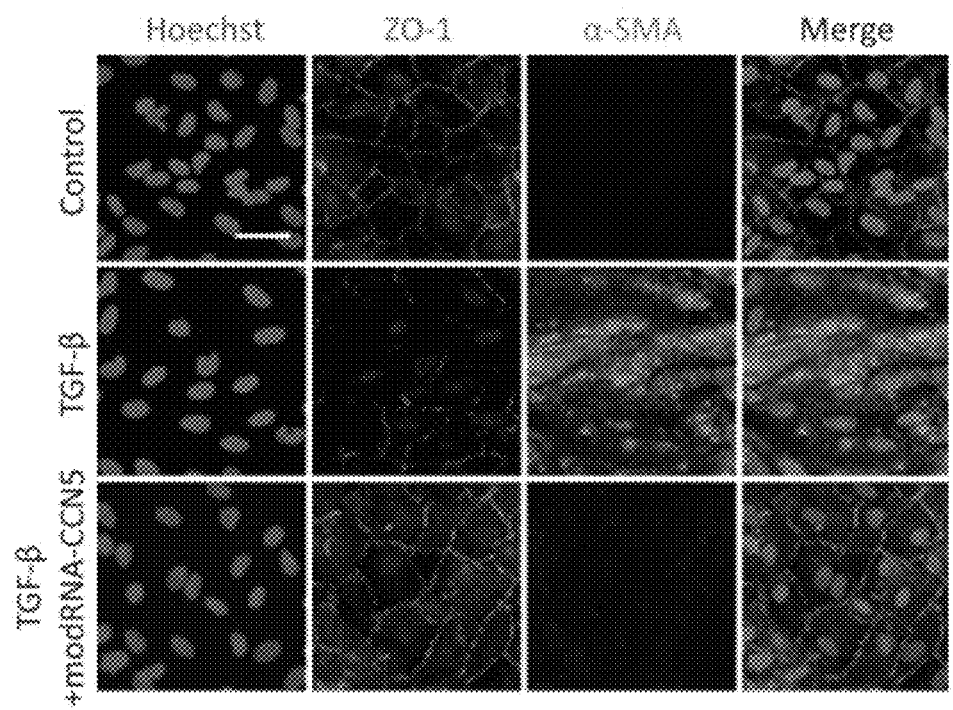
FIG. 12c illustrates results obtained by subjecting TGF-β-treated ARPE-19 cells to treatment with modified mRNA encoding CCN5, and then observing the ARPE-19 cells using anti-ZO-1 antibody, anti-α-SMA antibody, and phalloidin.
Figure 12C:
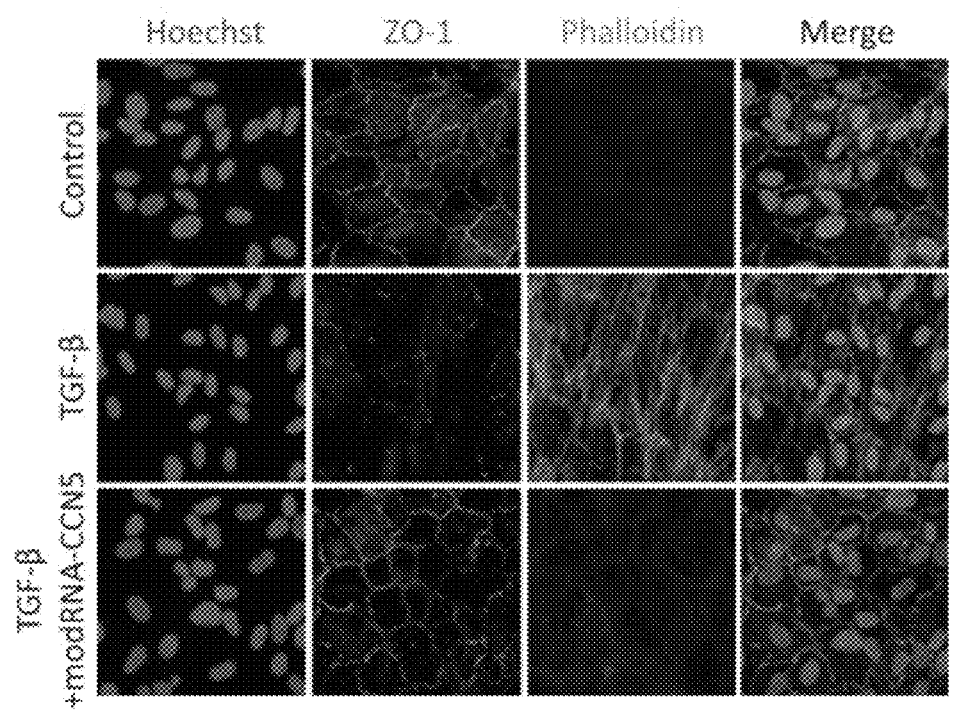
Figure 13A:
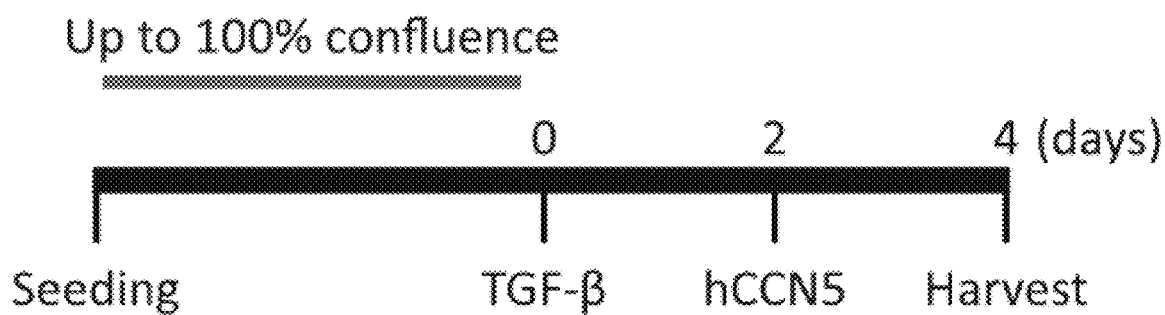
FIG. 13a schematically illustrates a process for identifying whether TGF-β-induced fibrotic deformation of ARPE-19 cells is restored by CCN5 protein.
Figure 13B:
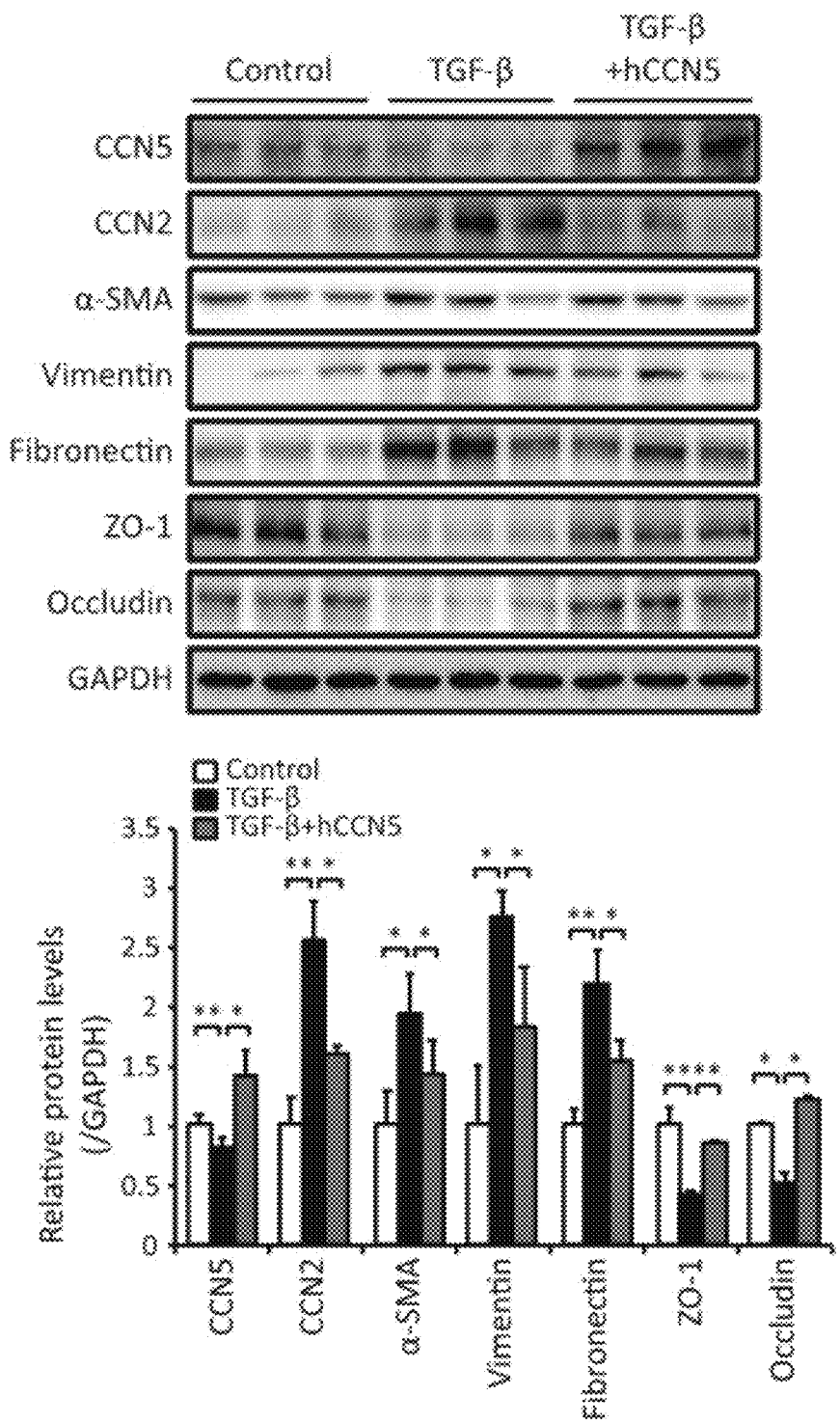
FIG. 13b illustrates results obtained by subjecting TGF-β-treated ARPE-19 cells to treatment with CCN5 protein, and then observing expression of CCN5, CCN2, mesenchymal marker proteins, and epithelial marker proteins in the ARPE-19 cells.
Figure 13C:
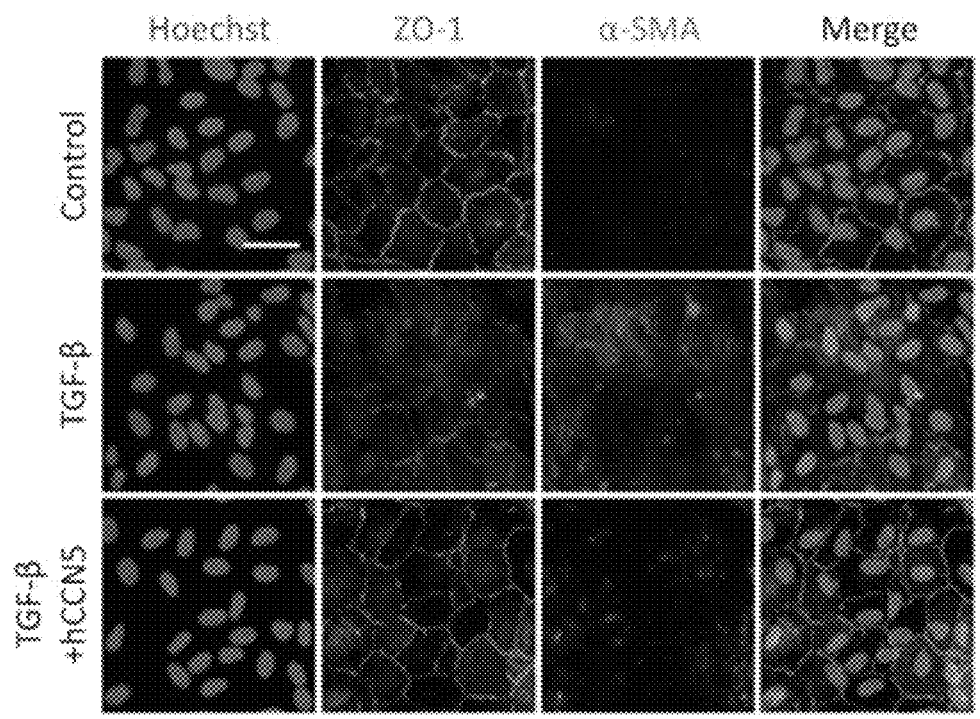
FIG. 13c illustrates results obtained by subjecting TGF-β-treated ARPE-19 cells to treatment with CCN5 protein, and then observing the ARPE-19 cells using anti-ZO-1 antibody, anti-α-SMA antibody, and phalloidin.
Figure 13C:
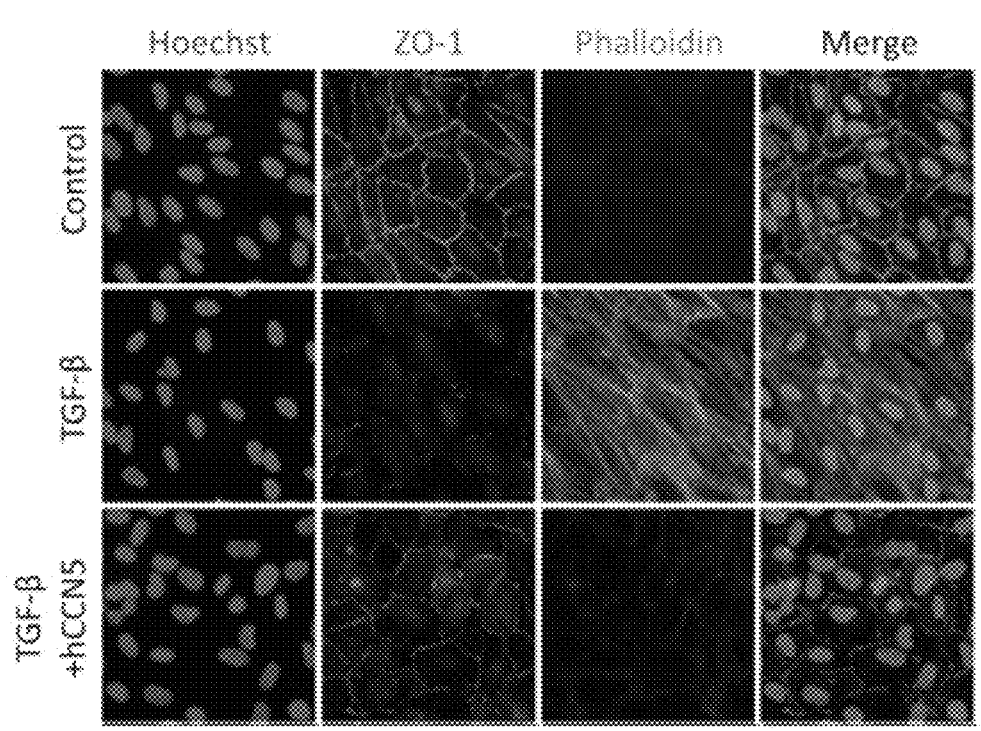

Western blotting showed that in ARPE-19 cells, modRNA-CCN5 and purified CCN5 protein inhibited increased expression of mesenchymal marker proteins (α-SMA, vimentin, and fibronectin) and restored decreased expression of epithelial marker proteins (ZO-1 and occludin) to a normal level, both increase and decrease being induced by TGF-β (FIGS. 12b and 13b). In addition, immunofluorescence staining showed that the modRNA-CCN5 and purified CCN5 protein restore the tight junction, disrupted by TGF-β, to normal (FIG. 12c and FIG. 13c). The results show that even in a case where CCN5 is delivered in the form of modified mRNA and purified protein, it has an excellent effect in restoring fibrotic deformation of ARPE-19 cells induced by TGF-β.

EXPERIMENTAL EXAMPLE 10

Preventive Effect of CCN5 on Fibrotic Deformation of ARPE-19 Cells Induced by Anti-VEGF Drugs (Bevacizumab, Ranibizumab, and Aflibercept)

Figure 14A:
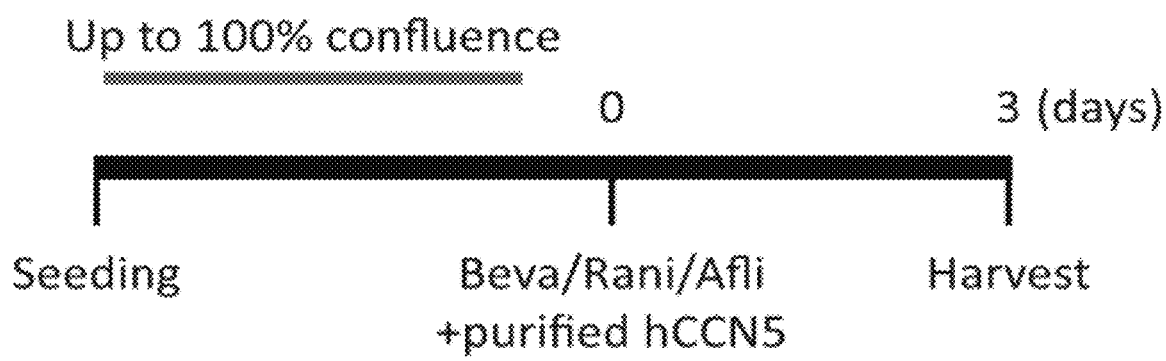
FIG. 14a schematically illustrates a process for measuring whether in a case where ARPE-19 cells are subjected to simultaneous treatment with anti-VEGF drugs (bevacizumab, ranibizumab, and aflibercept) and CCN5 protein, anti-VEGF drug-induced fibrotic deformation of the ARPE-19 cells is inhibited by the CCN5 protein.

It was examined whether bevacizumab, ranibizumab, and aflibercept, which were anti-VEGF drugs, equally induced fibrotic deformation in ARPE-19 cells and whether this deformation was prevented by CCN5 (FIG. 14a). The experimental process is schematically illustrated in FIG. 14a, and the experimental results are illustrated in FIGS. 14b and 14c.

Figure 14B:
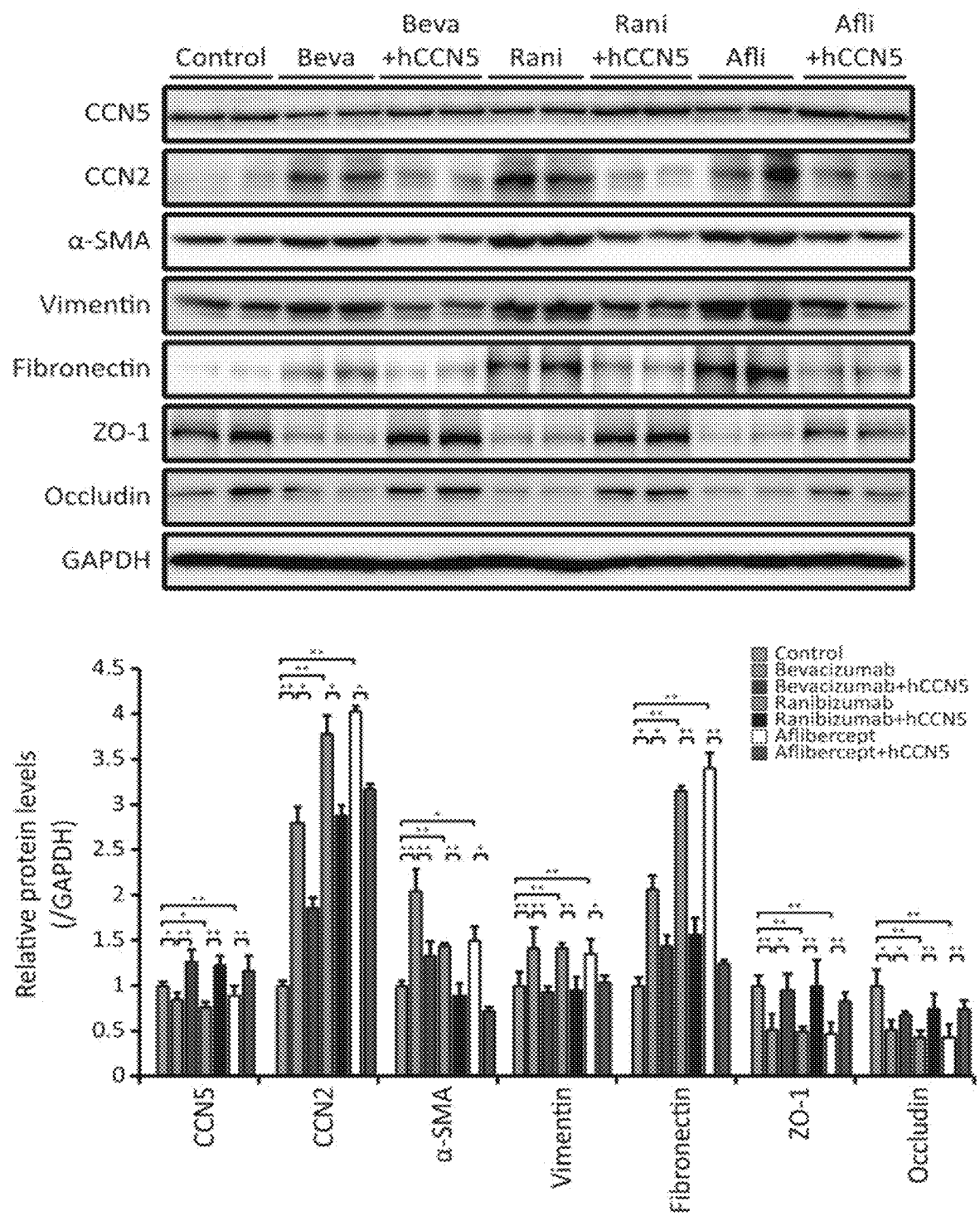
FIG. 14b illustrates results obtained by subjecting ARPE-19 cells to simultaneous treatment with anti-VEGF drugs (bevacizumab, ranibizumab, and aflibercept) and CCN5 protein, and then observing expression of CCN5, CCN2, mesenchymal marker proteins, and epithelial marker proteins in the ARPE-19 cells.
Figure 14C:
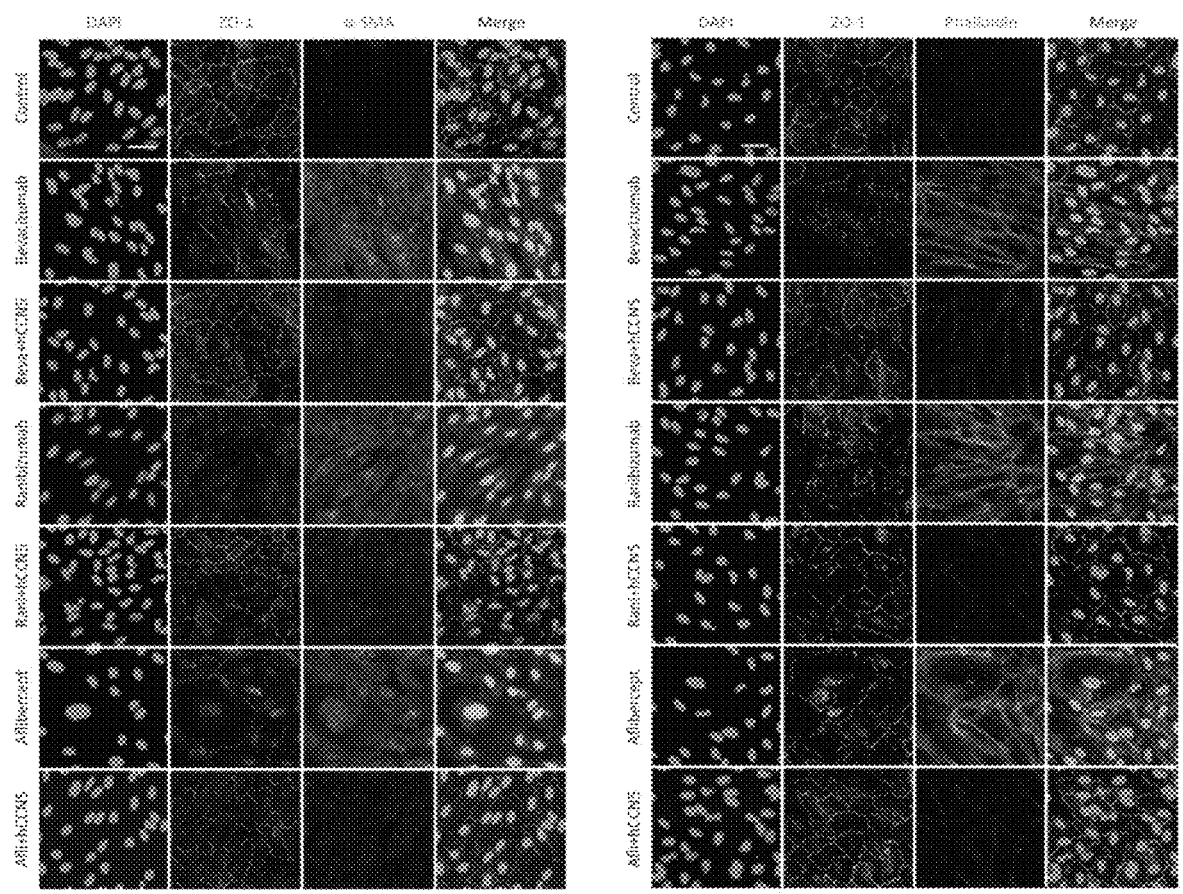
FIG. 14c illustrates results obtained by subjecting ARPE-19 cells to simultaneous treatment with anti-VEGF drugs (bevacizumab, ranibizumab, and aflibercept) and CCN5 protein, and then observing the ARPE-19 cells using anti-ZO-1 antibody, anti-α-SMA antibody, and phalloidin.

As illustrated in FIG. 14b, bevacizumab, ranibizumab, and aflibercept, which are anti-VEGF drugs, equally resulted in decreased expression of CCN5 and increased expression of CCN2, and this phenomenon was inhibited by CCN5 protein. Western blotting showed that CCN5 inhibited increased expression of mesenchymal marker proteins (α-SMA, vimentin, and fibronectin) and decreased expression of epithelial marker proteins (ZO-1 and occludin), both increase and decrease being induced by anti-VEGF drugs (FIG. 14c). In addition, immunofluorescence staining showed that CCN5 inhibited disruption of tight junction, increased expression of α-SMA, and formation of f-actin, all of which were induced by anti-VEGF drugs (FIG. 14c). These results show that fibrotic deformation of ARPE-19 cells induced by anti-VEGF drugs is prevented by CCN5.

EXPERIMENTAL EXAMPLE 11

Preventive Effect of CCN5 on Fibrotic Deformation of iPSC-Derived RPE Cells Induced by TGF-β

Figure 15A:
FIG. 15a schematically illustrates an experimental process for identifying whether in a case where iPSC-derived RPE cells are treated with AAV2-CCN5 and then with TGF-β, TGF-β-induced fibrotic deformation of the RPE cells is inhibited by CCN5.

Experiments for identifying a preventive effect of human-derived CCN5 on fibrotic deformation of RPE cells induced by TGF-β were performed in human iPSC-derived RPE cells. The iPSC-derived RPE cells were seeded, and 2 weeks later, the cells were infected with AAV2-CCN5. Then, culture was performed for 25 days, and then treatment with TGF-β was performed for 3 days (FIG. 15a). Within 2 weeks of cell seeding, the iPSC-derived RPE cells show a tightly packed cobblestone shape. One month later, the cells began to show RPE cell-specific pigmentation while forming a dome shape. The results are illustrated in FIG. 15b.

Figure 15B:
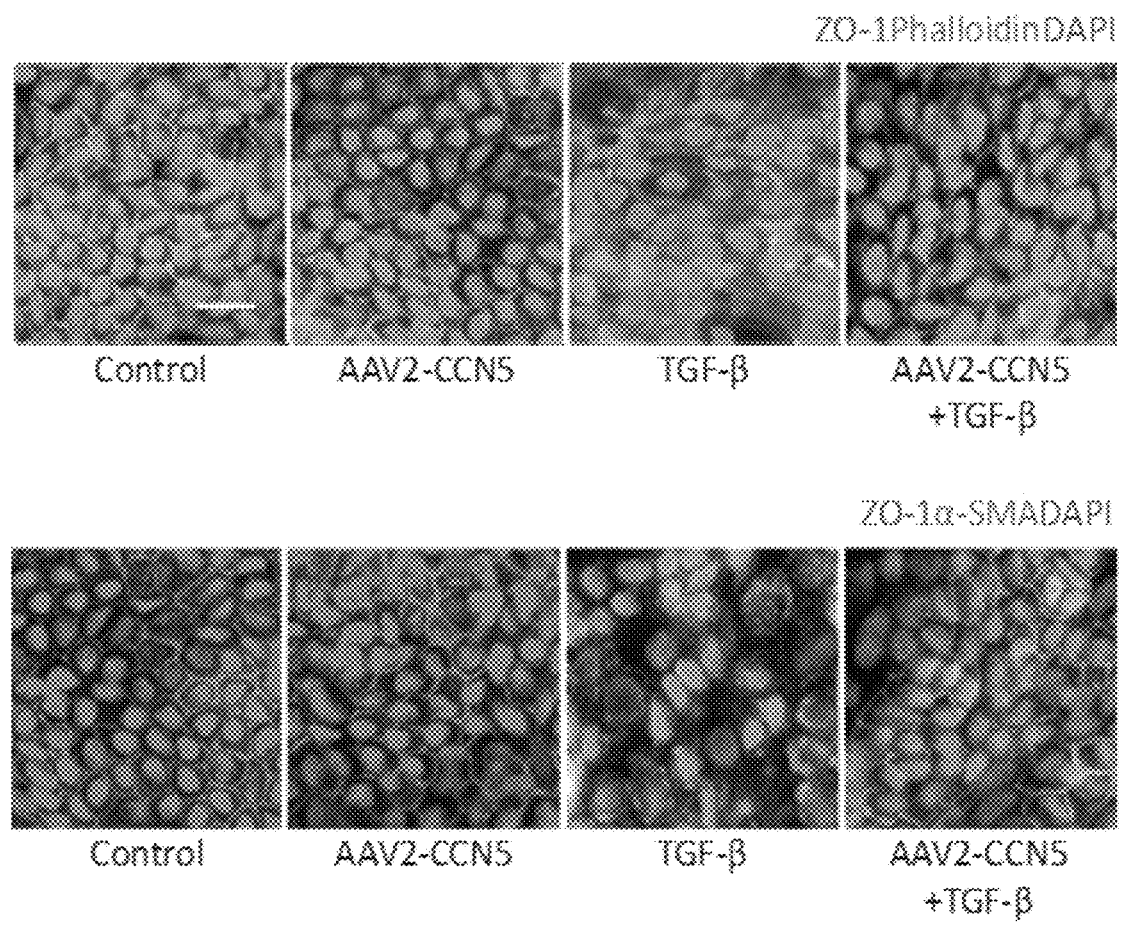
FIG. 15b illustrates results obtained by subjecting iPSC-derived RPE cells to treatment with AAV2-CCN5 followed by TGF-β, and then observing images of the RPE cells using anti-ZO-1 antibody, anti-α-SMA antibody, and phalloidin.

Immunofluorescence staining showed that AAV2-CCN5 inhibits disruption of tight junction, increased expression of α-SMA, and formation of f-actin, all of which were induced by TGF-β (FIG. 15b). The above results show that fibrotic deformation of iPSC-derived RPE cells, induced by TGF-β, is prevented by CCN5.

The invention claimed is:

1. A method for treating a retinal disease of a subject in need thereof, comprising:
a step of administering, to the subject, an effective amount of a pharmaceutical composition comprising an active ingredient selected from the group consisting of:
(a) a CCN5 protein; and
(b) a recombinant viral vector comprising a nucleic acid encoding the CCN5 protein;
wherein the retinal disease is proliferative vitreoretinopathy, diabetic retinopathy, or macular degeneration;
wherein the pharmaceutical composition is administered intravitreally or intraocularly.

2. The method of claim 1, further comprising administering an anti-VEGF (vascular endothelial growth factor) drug.

3. The method of claim 2, wherein the anti-VEGF drug is bevacizumab, ranibizumab, or aflibercept.

4. The method of claim 1, wherein the CCN5 protein is human CCN5 protein.

5. The method of claim 1, wherein the nucleic acid (b) encoding the CCN5 protein is an mRNA.

6. The method of claim 1, wherein the CCN5 protein is a polypeptide comprising the amino acid sequence of SEQ ID NO: 3 or SEQ ID NO: 6.

7. The method of claim 1, wherein the nucleic acid encoding the CCN5 protein comprises the nucleotide sequence of SEQ ID NO: 2 or SEQ ID NO: 5.

8. The method of claim 1, wherein the virus is any one selected from the group consisting of adenovirus, adeno-associated virus (AAV), retrovirus, lentivirus, herpes simplex virus, and vaccinia virus.

* * * * *